US007994293B2

(12) United States Patent
An et al.

(10) Patent No.: US 7,994,293 B2
(45) Date of Patent: Aug. 9, 2011

(54) ANTIBODIES SPECIFIC FOR DKK-1

(75) Inventors: Zhiqiang An, Ambler, PA (US); Fang Chen, North Wales, PA (US); John E. Fisher, Jenkintown, PA (US); Helmut Glantschnig, Schwenksville, PA (US); Donald B. Kimmel, Doylestown, PA (US); Alfred A. Reszka, New Hope, PA (US); Fubao Wang, Dresher, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 248 days.

(21) Appl. No.: 12/012,885

(22) Filed: Feb. 6, 2008

(65) Prior Publication Data

US 2008/0193449 A1  Aug. 14, 2008

Related U.S. Application Data

(60) Provisional application No. 60/900,226, filed on Feb. 8, 2007.

(51) Int. Cl.
*C07K 16/24* (2006.01)
*C07K 16/00* (2006.01)

(52) U.S. Cl. ............. 530/388.23; 530/387.1; 530/387.9; 530/388.1

(58) Field of Classification Search ........................ None
See application file for complete search history.

(56) References Cited

U.S. PATENT DOCUMENTS

| 6,344,541 | B1 | 2/2002 | Bass et al. |
| 6,844,422 | B1 | 1/2005 | Niehrs et al. |
| 7,057,017 | B2 | 6/2006 | McCarthy |
| 7,138,508 | B2 | 11/2006 | Niehrs et al. |
| 2003/0165501 | A1 | 9/2003 | DeAlmeida et al. |
| 2004/0038860 | A1 | 2/2004 | Allen et al. |
| 2005/0069915 | A1 | 3/2005 | McCarthy |
| 2005/0079173 | A1 | 4/2005 | Niehrs et al. |
| 2006/0127393 | A1 | 6/2006 | Li et al. |
| 2007/0128187 | A1 | 6/2007 | Allen et al. |

FOREIGN PATENT DOCUMENTS

| JP | 2006-217844 A | 8/2006 |
| WO | WO02/092015 A2 | 11/2002 |
| WO | WO2005/049640 A2 | 6/2005 |
| WO | WO2006/015373 A2 | 2/2006 |
| WO | WO2007/034344 A2 | 3/2007 |
| WO | WO2008/097510 A1 | 8/2008 |

OTHER PUBLICATIONS

Rudikoff et al. PNAS 1982 79:1979.*
Padlan et al. PNAS 1989, 86:5938-5942.*
Bendig Methods: A Companion to Methods in Enzymology 1995; 8:83-93.*
MacCallum et al. J. Mol. Biol. (1996) 262, 732-745.*
Pascalis et al. (The Journal of Immunology (2002) 169, 3076-3084.*
Casset et al. (BBRC 2003, 307:198-205.*
Vajdos et al. (J. Mol. Biol. (2002) 320, 415-428.*
Chen et al. (J. Mol. Bio. (1999) 293, 865-881.*
Wu et al. (J. Mol. Biol. (1999) 294, 151-162.*
Lamminmaki et al. (JBC 2001, 276:36687-36694.*
Patel, et al., "Regulation of Bone Formation and Vision by LRP5", New England Journal of Medicine, vol. 346, No. 20, pp. 1572-1573, May 16, 2002.
Boyden, et al, "High Bone Density Due to a Mutation in LDL-Receptor-Related Protein 5", New England Journal of Medicine, vol. 346, No. 20, pp. 1513-1521, May 16, 2002.
Glinka, et al., "Dickkopf-1 is a member of a new family secreted proteins and functions in head induction", Nature, vol. 391: pp. 357-362, Jan. 22, 1998.
Lipfert, et al., "Identificiation of DKK1 Residues Necessary for Interaction with LRP5/6", J. of Bone and Mineral Research, 21:S99, 2006.
Grisanti M, et al., "Dkk-1 Inhibition Increases Bone Mineral Density in Rodents", J. of Bone and Mineral Research, 21:S25, 2006.
Krupnik, et al., "Functional and structural diversity of the human Dickkopf gene family", Elsevier, Gene, vol. 238, pp. 301-313, 1999.
Harada & Rodan, "Control of osteoblast function and regulation of bone mass", Nature, vol. 423, pp. 349-355, May 15, 2003.
Yaccoby et al., "Antibody-based inhibition of DKK1 suppresses tumor-induced bone resorption and multiple myeloma growth in vivo", Blood, vol. 109, No. 5, pp. 2106-2011, Mar. 1, 2007.
Fedi, et al., "Isolation and Biochemical Characterization of the Human Dkk-1 Homologue, a Novel Inhibitor of Mammalian Wnt Signaling", J. of Biological Chemistry,vol. 274, No. 27, pp. 19465-19472, 1999.
Diarra, et al., "Dickkopf-1 is a master regulator of joint remodeling", Nature Medicine, vol. 13, No. 2, pp. 156-163, Feb. 2007.
Terpose, et al., "Antibodies to dickkopf-1 protein", Informa Healthcare, Expert Opinion on Therapeutic Patents, vol. 16, No. 10, pp. 1453-1458, 2006.

* cited by examiner

*Primary Examiner* — Sharon Wen
(74) *Attorney, Agent, or Firm* — Patricia L. Chisholm; Immac J. Thampoe

(57) ABSTRACT

Antibodies specific for Dkk-1, an inhibitor of the osteoanabolic Wnt/LRP5 signaling pathway, are described. The antibodies, which inhibit binding of Dkk-1 to LRP5, are useful in compositions for stimulating bone growth, in particular, compositions for treating bone disorders which result in a loss in bone, for example, osteoporosis.

13 Claims, 21 Drawing Sheets

Amino Acid Sequences of Rh2-18

*Rh2-18 Antibody Light Chain Amino Acid Sequence*

```
  1  QSVLTQPPSV  SGAPGQRVTI  SCTGSSSNIG  AGYDVHWYQQ  LPGTAPKLLI
 51  YGYSNRPSGV  PDRFSGSKSG  ASASLAITGL  RPDDEADYYC  QSYDNSLSSY
101  VFGGGTQLTV  LSQPKANPTV  TLFPPSSEEL  QANKATLVCL  ISDFYPGAVT
151  VAWKADGSPV  KAGVETTKPS  KQSNNKYAAS  SYLSLTPEQW  KSHRSYSCQV
201  THEGSTVEKT  VAPTECS
```

*Rh2-18 Antibody Heavy Chain Amino Acid Sequence*

```
  1  EVQLVQSGAE  VKKPGASVKV  SCKASGYTFT  DYYIHWVRQA  PGQGLEWMGW
 51  IHSNSGATTY  AQKFQARVTM  SRDTSSSTAY  MELSRLESDD  TAMYFCSRED
101  YWGQGTLVTV  SSASTKGPSV  FPLAPCSRST  SESTAALGCL  VKDYFPEPVT
151  VSWNSGALTS  GVHTFPAVLQ  SSGLYSLSSV  VTVTSSNFGT  QTYTCNVDHK
201  PSNTKVDKTV  ERKCCVECPP  CPAPPVAGPS  VFLFPPKPKD  TLMISRTPEV
251  TCVVVDVSQE  DPEVQFNWYV  DGVEVHNAKT  KPREEQFNST  FRVVSVLTVL
301  HQDWLNGKEY  KCKVSNKGLP  SSIEKTISKT  KGQPREPQVY  TLPPSREEMT
351  KNQVSLTCLV  KGFYPSDIAV  EWESNGQPEN  NYKTTPPMLD  SDGSFFLYSK
401  LTVDKSRWQQ  GNVFSCSVMH  EALHNHYTQK  SLSLSPGK
```

FIGURE 1C

Light chain variable region sequence

```
L-001874698    QSVLTQPPSV SGAPGQRVTI SCTGSSSNIG AGYDVHWYQQ LPGTAPKLLI
VL1 14-7A      QSVLTQPPSV SGAPGQRVTI SCTGSSSNIG AGYDVHWYQQ LPGTAPKLLI
                                     LCDR1

L-001874698    YGYSNRPSGV PDRFSGSKSG ASASLAITGL RPDDEADYYC QSYDNSLSSY
VL1 14-7A      YGNSNRPSGV PDRFSGSKSG TSASLAITGL QAEDEADYYC QSYDSSLSG
                   LCDR2                                      LCDR3

L-001874698    - VFGGGTQLTV LS
(JL7)        A VFGGGTQLTV L
```

FIGURE 1D

Heavy chain variable region sequence

```
L-0018746989        EVQLVQSGAE VKKPGASVKV SCKASGYTFT DYYIHWVRQA PGQGLEWMGW
VH1 1-3 1-02        QVQLVQSGAE VKKPGASVKV SCKASGYTFT GYYMHWVRQA PGQGLEWMGW
                                                   HCDR1

L-0018746989        IHSNSGATTY AQKFQARVTM SRDTSSSTAY MELSRLESDD TAMYFCSR
VH1 1-3 1-02        INPNSGGTNY AQKFQGRVTM TRDTSISTAY MELSRLRSDD TAVYYCAR
                                 HCDR2

L-0018746989        -ED YWGQGTLVTV SS
(JH4)               YFD YWGQGTLVTV SS
                    HCDR3
```

FIGURE 1E

FIGURE 6A

SEQUENCE LISTING

```
<160> NUMBER OF SEQ ID NOS: 71

<210> SEQ ID NO 1
<211> LENGTH: 714
<212> TYPE: DNA
<213> ORGANISM: Artificial Sequence
<220> FEATURE:
<223> OTHER INFORMATION: RH2-18 Antibody Light Chain DNA Sequence

<400> SEQUENCE: 1
atgagtgtgc ccactcaggt cctggggttg ctgctgctgt ggcttacaga tgccagatgc      60
cagtctgtgt tgacgcagcc gccctcagtg tctggggccc cagggcagag ggtcaccatc     120
tcctgcactg ggagcagctc caacatcggg gcaggttatg atgtacactg gtaccagcag     180
cttccaggaa cagcccccaa actcctcatc tatggttaca gcaatcggcc ctcagggg      240 cctgaccgat tctctggctc caagtctggc gcctcagcct ccctggccat cactgggctc     300
cggcctgacg atgaggctga ttactattgc cagtcctatg acaacagcct gagttcttat     360
gtcttcggag gtgggaccca gctcaccgtt ttaagtcagc ccaaggccaa ccccaccgtg     420
accctgttcc ccccatcttc tgaggagctg caagccaaca ggccacccct ggtgtgcctg     480
atctctgact tctaccctgg cgctgtgaca gtggcctgga aggctgatgg ctctcctgtg     540
aaggctggcg tggagaccac caagccatct aagcagtcta acaacaagta tgctgcctct     600
tcttacctgt ctctgacccc tgagcagtgg aagagccacc ggtcttactc ttgccaggtg     660
acccatgagg gctctacagt ggagaagaca gtggccccca cagagtgctc ttga          714

<210> SEQ ID NO 2
<211> LENGTH: 237
<212> TYPE: PRT
<213> ORGANISM: Artificial Sequence
<220> FEATURE:
<223> OTHER INFORMATION: RH2-18 Antibody Light Chain Amino Acid Sequence

<400> SEQUENCE: 2

Met Ser Val Pro Thr Gln Val Leu Gly Leu Leu Leu Leu Trp Leu Thr
 1               5                  10                  15

Asp Ala Arg Cys Gln Ser Val Leu Thr Gln Pro Pro Ser Val Ser Gly
            20                  25                  30
```

```
Ala Pro Gly Gln Arg Val Thr Ile Ser Cys Thr Gly Ser Ser Ser Asn
            35                  40                  45

Ile Gly Ala Gly Tyr Asp Val His Trp Tyr Gln Gln Leu Pro Gly Thr
 50                  55                  60

Ala Pro Lys Leu Leu Ile Tyr Gly Tyr Ser Asn Arg Pro Ser Gly Val
 65                  70                  75                  80

Pro Asp Arg Phe Ser Gly Ser Lys Ser Gly Ala Ser Ala Ser Leu Ala
                85                  90                  95

Ile Thr Gly Leu Arg Pro Asp Asp Glu Ala Asp Tyr Tyr Cys Gln Ser
            100                 105                 110

Tyr Asp Asn Ser Leu Ser Ser Tyr Val Phe Gly Gly Gly Thr Gln Leu
        115                 120                 125

Thr Val Leu Ser Gln Pro Lys Ala Asn Pro Thr Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Gly Ser Pro Val Lys Ala Gly Val Glu Thr Thr Lys Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 3
<211> LENGTH: 217
<212> TYPE: PRT
<213> ORGANISM: Artificial Sequence
<220> FEATURE:
<223> OTHER INFORMATION: RH2-18 Antibody Light Chain Amino Acid Sequence
      without leader

<400> SEQUENCE: 3

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Tyr Ser Asn Arg Pro Ser Gly Val Pro Asp Arg Phe
 50                  55                  60

Ser Gly Ser Lys Ser Gly Ala Ser Ala Ser Leu Ala Ile Thr Gly Leu
65                  70                  75                  80

Arg Pro Asp Asp Glu Ala Asp Tyr Tyr Cys Gln Ser Tyr Asp Asn Ser
                85                  90                  95

Leu Ser Ser Tyr Val Phe Gly Gly Gly Thr Gln Leu Thr Val Leu Ser
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160
```

```
Lys Ala Gly Val Glu Thr Thr Lys Pro Ser Lys Gln Ser Asn Asn Lys
            165                 170                 175

Tyr Ala Ala Ser Ser Tyr Leu Ser Leu Thr Pro Glu Gln Trp Lys Ser
        180                 185                 190

His Arg Ser Tyr Ser Cys Gln Val Thr His Glu Gly Ser Thr Val Glu
    195                 200                 205

Lys Thr Val Ala Pro Thr Glu Cys Ser
    210                 215

<210> SEQ ID NO 4
<211> LENGTH: 112
<212> TYPE: PRT
<213> ORGANISM: Artificial Sequence
<220> FEATURE:
<223> OTHER INFORMATION: RH2-18 Antibody light chain variable region
      sequence

<400> SEQUENCE: 4

Gln Ser Val Leu Thr Gln Pro Pro Ser Val Ser Gly Ala Pro Gly Gln
1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Tyr Ser Asn Arg Pro Ser Gly Val Pro Asp Arg Phe
50                  55                  60

Ser Gly Ser Lys Ser Gly Ala Ser Ala Ser Leu Ala Ile Thr Gly Leu
65                  70                  75                  80

Arg Pro Asp Asp Glu Ala Asp Tyr Tyr Cys Gln Ser Tyr Asp Asn Ser
                85                  90                  95

Leu Ser Ser Tyr Val Phe Gly Gly Gly Thr Gln Leu Thr Val Leu Ser
            100                 105                 110

<210> SEQ ID NO 5
<211> LENGTH: 1374
<212> TYPE: DNA
<213> ORGANISM: Artificial Sequence
<220> FEATURE:
<223> OTHER INFORMATION: RH2-18 Antibody Heavy Chain DNA Sequence

<400> SEQUENCE: 5
atggaatgga gctgggtctt tctcttcttc ctgtcagtaa ctacaggtgt ccactcggag     60
gtgcagctgg tgcagtctgg ggctgaggtg aagaagcctg ggcctcagt gaaggtctcc    120 tgcaaggctt ctggatacac cttcaccgac tactatatac actgggtgcg acaggcccct   180
ggacaagggc ttgagtggat gggatggatc cactctaaca gtggcgccac aacctatgca   240
cagaagtttc aggccagggt caccatgagc agggacacgt ccagcagcac agcctacatg   300
gagttgagca gctgaatc tgacgacacg gccatgtatt ttgttcgag agaggactac    360 tggggccaag gaaccctggt caccgtctcg agtgcatcca ccaagggccc atccgtcttc   420
cccctggcgc cctgctccag gagcacctcc gagagcacag ccgccctggg ctgcctggtc   480
aaggactact cccccgaacc ggtgacggtg tcgtggaact caggcgccct gaccagcggc   540
gtgcacacct tcccggctgt cctacagtcc tcaggactct actccctcag cagcgtggtg   600
accgtgacct cccagcaact tggcacgcag acctacacct gcaacgtaga tcacaagccc   660
agcaacacca aggtggacaa gacagttgag cggaaatgct gcgtggagtg cccaccatgc   720
ccagcacctc cagtggccgg accatcagtc ttcctgttcc ccccaaaacc caaggacact   780
```

-continued

```
ctcatgatct cccggacccc tgaggtcacg tgcgtggtgg tggacgtgag ccaggaagac    840
cccgaggtcc agttcaactg gtacgtggat ggcgtggagg tgcataatgc caagacaaag    900
ccgcgggagg agcagttcaa cagcacgttc cgtgtggtca gcgtcctcac cgtcctgcac    960
caggactggc tgaacggcaa ggagtacaag tgcaaggtct ccaacaaagg cctcccgtcc   1020
tccatcgaga aaaccatctc caaaaccaaa gggcagcccc gagagccaca ggtgtacacc   1080
ctgcccccat cccgggagga gatgaccaag aaccaggtca gcctgacctg cctggtcaaa   1140
ggcttctacc ccagcgacat cgccgtggag tgggagagca atgggcagcc ggagaacaac   1200
tacaagacca cgcctcccat gctggactcc gacggctcct tcttcctcta cagcaagcta   1260
accgtggaca agagcaggtg gcagcagggg aatgtcttct catgctccgt gatgcatgag   1320
gctctgcaca accactacac acagaagagc ctctccctgt cctggtaa atga           1374
```

<210> SEQ ID NO 6
<211> LENGTH: 457
<212> TYPE: PRT
<213> ORGANISM: Artificial Sequence
<220> FEATURE:
<223> OTHER INFORMATION: RH2-18 Antibody Heavy Chain Amino Acid Sequence

<400> SEQUENCE: 6

```
Met Glu Trp Ser Trp Val Phe Leu Phe Phe Leu Ser Val Thr Thr Gly
  1               5                  10                  15

Val His Ser Glu Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Asp Tyr Tyr Ile His Trp Val Arg Gln Ala Pro Gly Gln Gly Leu
     50                  55                  60

Glu Trp Met Gly Trp Ile His Ser Asn Ser Gly Ala Thr Thr Tyr Ala
 65                  70                  75                  80

Gln Lys Phe Gln Ala Arg Val Thr Met Ser Arg Asp Thr Ser Ser Ser
                 85                  90                  95

Thr Ala Tyr Met Glu Leu Ser Arg Leu Glu Ser Asp Asp Thr Ala Met
            100                 105                 110

Tyr Phe Cys Ser Arg Glu Asp Tyr Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Thr Ser Ser Asn Phe Gly
        195                 200                 205

Thr Gln Thr Tyr Thr Cys Asn Val Asp His Lys Pro Ser Asn Thr Lys
    210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Phe Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 7
<211> LENGTH: 438
<212> TYPE: PRT
<213> ORGANISM: Artificial Sequence
<220> FEATURE:
<223> OTHER INFORMATION: Rh2-18 Antibody Heavy Chain Amino Acid Sequence
      without leader

<400> SEQUENCE: 7

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile His Ser Asn Ser Gly Ala Thr Thr Tyr Ala Gln Lys Phe
    50                  55                  60

Gln Ala Arg Val Thr Met Ser Arg Asp Thr Ser Ser Ser Thr Ala Tyr
65                  70                  75                  80

Met Glu Leu Ser Arg Leu Glu Ser Asp Asp Thr Ala Met Tyr Phe Cys
                85                  90                  95

Ser Arg Glu Asp Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Thr Ser Ser Asn Phe Gly Thr Gln Thr
            180                 185                 190

Tyr Thr Cys Asn Val Asp His Lys Pro Ser Asn Thr Lys Val Asp Lys
            195                 200                 205

Thr Val Glu Arg Lys Cys Cys Val Glu Cys Pro Pro Cys Pro Ala Pro
210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
            245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
            275                 280                 285

Ser Thr Phe Arg Val Val Ser Val Leu Thr Val Leu His Gln Asp Trp
            290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Thr Lys Gly Gln Pro Arg Glu
            325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
            370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
            405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 8
<211> LENGTH: 110
<212> TYPE: PRT
<213> ORGANISM: Artificial Sequence
<220> FEATURE:
<223> OTHER INFORMATION: Rh2-18 heavy chain variable region

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile His Ser Asn Ser Gly Ala Thr Tyr Ala Gln Lys Phe
    50                  55                  60

Gln Ala Arg Val Thr Met Ser Arg Asp Thr Ser Ser Thr Ala Tyr
65                  70                  75                  80

Met Glu Leu Ser Arg Leu Glu Ser Asp Asp Thr Ala Met Tyr Phe Cys
                85                  90                  95

Ser Arg Glu Asp Tyr Trp Gly Gln Gly Thr Leu Val Thr Val
            100                 105                 110

<210> SEQ ID NO 9
<211> LENGTH: 5
<212> TYPE: PRT
<213> ORGANISM: Artificial Sequence
<220> FEATURE:
<223> OTHER INFORMATION: RH2-18 HC CDR1

<400> SEQUENCE: 9

Asp Tyr Tyr Ile His
1               5

<210> SEQ ID NO 10
<211> LENGTH: 17
<212> TYPE: PRT
<213> ORGANISM: Artificial Sequence
<220> FEATURE:
<223> OTHER INFORMATION: RH2-18 HC CDR2

<400> SEQUENCE: 10

Trp Ile His Ser Asn Ser Gly Ala Thr Thr Tyr Ala Gln Lys Phe Gln
1               5                   10                  15
Ala

<210> SEQ ID NO 11
<211> LENGTH: 3
<212> TYPE: PRT
<213> ORGANISM: Artificial Sequence
<220> FEATURE:
<223> OTHER INFORMATION: RH2-18 HC CDR3

<400> SEQUENCE: 11

Glu Asp Tyr
1

<210> SEQ ID NO 12
<211> LENGTH: 14
<212> TYPE: PRT
<213> ORGANISM: Artificial Sequence
<220> FEATURE:
<223> OTHER INFORMATION: RH2-18 LC CDR1

<400> SEQUENCE: 12

Thr Gly Ser Ser Ser Asn Ile Gly Ala Gly Tyr Asp Val His
1               5                   10

<210> SEQ ID NO 13
<211> LENGTH: 7
<212> TYPE: PRT
<213> ORGANISM: Artificial Sequence
<220> FEATURE:
<223> OTHER INFORMATION: RH2-18 LC CDR2

<400> SEQUENCE: 13

Gly Tyr Ser Asn Arg Pro Ser
1               5

<210> SEQ ID NO 14
<211> LENGTH: 11
<212> TYPE: PRT
<213> ORGANISM: Artificial Sequence
<220> FEATURE:
<223> OTHER INFORMATION: RH2-18 LC CDR3

<400> SEQUENCE: 14

Gln Ser Tyr Asp Asn Ser Leu Ser Ser Tyr Val
1               5                   10

<210> SEQ ID NO 15
<211> LENGTH: 113
<212> TYPE: PRT
<213> ORGANISM: Artificial Sequence
<220> FEATURE:
<223> OTHER INFORMATION: VH1 1-3 1-02 heavy chain variable region

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 16
<211> LENGTH: 111
<212> TYPE: PRT
<213> ORGANISM: Artificial Sequence
<220> FEATURE:
<223> OTHER INFORMATION: VL1 14-7A light chain variable region sequence

<400> SEQUENCE: 16

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Tyr Asp Ser Ser
                85                  90                  95

Leu Ser Gly Ala Val Phe Gly Gly Gly Thr Gln Leu Thr Val Leu
            100                 105                 110

<210> SEQ ID NO 17
<211> LENGTH: 714
<212> TYPE: DNA
<213> ORGANISM: Artificial Sequence
<220> FEATURE:
<223> OTHER INFORMATION: RH1-10 Antibody Light Chain DNA Sequence

<400> SEQUENCE: 17
atgagtgtgc ccactcaggt cctggggttg ctgctgctgt ggcttacaga tgccagatgc    60
cagtctgtgc tgactcagcc accctcagcg tctggggccc cagggcagag ggtcaccatc   120

```
tcctgcactg ggagcagctc caacatcggg gctggttatg atgtacactg gtaccagcag    180
cttccaggag cagcccccaa actcctcatc tatggtaaca gcaatcggcc ctcaggggtc    240
cctgaccgat tctctggctc caagtctggc acctcagcct ccctggccat cactgggctc    300
caggctgagg atgaggctga ttattattgc cagtcctatg acagcagcct gagtggttat    360
gtcttcggaa ctgggaccaa ggtcaccgtc ctaggtcagc ccaaggccaa ccccaccgtg    420
accctgttcc ccccatcttc tgaggagctg caagccaaca aggccaccct ggtgtgcctg    480
atctctgact ctacccctgg cgctgtgaca gtggcctgga aggctgatgg ctctcctgtg    540
aaggctggcg tggagaccac caagccatct aagcagtcta acaacaagta tgctgcctct    600
tcttacctgt ctctgacccc tgagcagtgg aagagccacc ggtcttactc ttgccaggtg    660
acccatgagg gctctacagt ggagaagaca gtggccccca cagagtgctc ttga          714
```

<210> SEQ ID NO 18
<211> LENGTH: 237
<212> TYPE: PRT
<213> ORGANISM: Artificial Sequence
<220> FEATURE:
<223> OTHER INFORMATION: RH1-10 Antibody Light Chain Amino Acid Sequence

<400> SEQUENCE: 18

```
Met Ser Val Pro Thr Gln Val Leu Gly Leu Leu Leu Leu Trp Leu Thr
  1               5                  10                  15

Asp Ala Arg Cys Gln Ser Val Leu Thr Gln Pro Pro Ser Ala Ser Gly
                 20                  25                  30

Ala Pro Gly Gln Arg Val Thr Ile Ser Cys Thr Gly Ser Ser Ser Asn
             35                  40                  45

Ile Gly Ala Gly Tyr Asp Val His Trp Tyr Gln Gln Leu Pro Gly Ala
 50                  55                  60

Ala Pro Lys Leu Leu Ile Tyr Gly Asn Ser Asn Arg Pro Ser Gly Val
 65                  70                  75                  80

Pro Asp Arg Phe Ser Gly Ser Lys Ser Gly Thr Ser Ala Ser Leu Ala
                 85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Tyr Val Phe Gly Thr Gly Thr Lys Val
            115                 120                 125

Thr Val Leu Gly Gln Pro Lys Ala Asn Pro Thr Val Thr Leu Phe Pro
        130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Gly Ser Pro Val Lys Ala Gly Val Glu Thr Thr Lys Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
        210                 215                 220

Ser Thr Val Glu Lys Thr Val Ala Pro Thr Glu Cys Ser
225                 230                 235
```

<210> SEQ ID NO 19
<211> LENGTH: 1374
<212> TYPE: DNA

```
<213> ORGANISM: Artificial Sequence
<220> FEATURE:
<223> OTHER INFORMATION: RH1-10 Antibody Heavy Chain DNA Sequence

<400> SEQUENCE: 19
atggaatgga gctgggtctt tctcttcttc ctgtcagtaa ctacaggtgt ccactcgcag      60
gtgcagctgt tgcagtctgc agcagaggtg aaaaagcccg ggagtctct gaagatctcc     120
tgtaagggtt ctggatacga ctttcccggc tactatctgc actgggtgcg acaggccct     180
ggacaaggcc ttgagtggat gggctggatc aacgctaaca gtggtgccac aaattatgca    240
cagaactttc agggcaggt caccatgacc agggacacgt ccatcagcgc agcttacatg     300
gagctgagca gcctgagatc tgacgacacg gccgtctatt attgtacgag agaggaccac    360
tggggccgag ggaccacggt caccgtctcc tcagcatcca ccaagggccc atccgtcttc    420
cccctggcgc cctgctccag gagcacctcc gagagcacag ccgccctggg ctgcctggtc    480
aaggactact cccccgaacc ggtgacggtg tcgtggaact caggcgccct gaccagcggc    540
gtgcacacct tcccggctgt cctacagtcc tcaggactct actccctcag cagcgtggtg    600
accgtgacct ccagcaactt tggcacgcag acctacacct gcaacgtaga tcacaagccc    660
agcaacacca aggtggacaa gacagttgag cggaaatgct gcgtggagtg cccaccatgc    720
ccagcacctc cagtggccgg accatcagtc ttcctgttcc ccccaaaacc caaggacact    780
ctcatgatct cccggacccc tgaggtcacg tgcgtggtgg tggacgtgag ccaggaagac    840
cccgaggtcc agttcaactg gtacgtggat ggcgtggagg tgcataatgc caagacaaag    900
ccgcgggagg agcagttcaa cagcacgttc cgtgtggtca gcgtcctcac cgtcctgcac    960
caggactggc tgaacggcaa ggagtacaag tgcaaggtct ccaacaaagg cctcccgtcc   1020
tccatcgaga aaaccatctc caaaaccaaa gggcagcccc gagagccaca ggtgtacacc   1080
ctgcccccat cccgggagga tgaccaag aaccaggtca gcctgacctg cctggtcaaa    1140
ggcttctacc ccagcgacat cgccgtggag tgggagagca atgggcagcc ggagaacaac   1200
tacaagacca cgcctcccat gctggactcc gacggctcct tcttcctcta cagcaagcta   1260
accgtggaca gagcaggtg gcagcagggg aatgtcttct catgctccgt gatgcatgag    1320
gctctgcaca accactacac acagaagagc ctctccctgt ctcctggtaa atga           1374

<210> SEQ ID NO 20
<211> LENGTH: 457
<212> TYPE: PRT
<213> ORGANISM: Artificial Sequence
<220> FEATURE:
<223> OTHER INFORMATION: RH1-10 Antibody Heavy Chain Amino Acid Sequence

<400> SEQUENCE: 20

Met Glu Trp Ser Trp Val Phe Leu Phe Phe Leu Ser Val Thr Thr Gly
 1               5                  10                  15

Val His Ser Gln Val Gln Leu Leu Gln Ser Ala Ala Glu Val Lys Lys
             20                  25                  30

Pro Gly Glu Ser Leu Lys Ile Ser Cys Lys Gly Ser Gly Tyr Asp Phe
         35                  40                  45

Pro Gly Tyr Tyr Leu His Trp Val Arg Gln Ala Pro Gly Gln Gly Leu
     50                  55                  60

Glu Trp Met Gly Trp Ile Asn Ala Asn Ser Gly Ala Thr Asn Tyr Ala
 65                  70                  75                  80

Gln Asn Phe Gln Gly Arg Val Thr Met Thr Arg Asp Thr Ser Ile Ser
                 85                  90                  95
```

```
Ala Ala Tyr Met Glu Leu Ser Ser Leu Arg Ser Asp Asp Thr Ala Val
            100                 105                 110
Tyr Tyr Cys Thr Arg Glu Asp His Trp Gly Arg Gly Thr Thr Val Thr
            115                 120                 125
Val Ser Ser Ala Ser Thr Lys Gly Pro Ser Val Phe Pro Leu Ala Pro
130             135                 140
Cys Ser Arg Ser Thr Ser Glu Ser Thr Ala Ala Leu Gly Cys Leu Val
145             150                 155                 160
Lys Asp Tyr Phe Pro Glu Pro Val Thr Val Ser Trp Asn Ser Gly Ala
                165                 170                 175
Leu Thr Ser Gly Val His Thr Phe Pro Ala Val Leu Gln Ser Ser Gly
            180                 185                 190
Leu Tyr Ser Leu Ser Ser Val Val Thr Val Thr Ser Ser Asn Phe Gly
            195                 200                 205
Thr Gln Thr Tyr Thr Cys Asn Val Asp His Lys Pro Ser Asn Thr Lys
            210                 215                 220
Val Asp Lys Thr Val Glu Arg Lys Cys Cys Val Glu Cys Pro Pro Cys
225             230                 235                 240
Pro Ala Pro Pro Val Ala Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser Gln Glu Asp Pro Glu Val Gln Phe Asn Trp Tyr
            275                 280                 285
Val Asp Gly Val Glu Val His Asn Ala Lys Thr Lys Pro Arg Glu Glu
            290                 295                 300
Gln Phe Asn Ser Thr Phe Arg Val Val Ser Val Leu Thr Val Leu His
305             310                 315                 320
Gln Asp Trp Leu Asn Gly Lys Glu Tyr Lys Cys Lys Val Ser Asn Lys
                325                 330                 335
Gly Leu Pro Ser Ser Ile Glu Lys Thr Ile Ser Lys Thr Lys Gly Gln
            340                 345                 350
Pro Arg Glu Pro Gln Val Tyr Thr Leu Pro Pro Ser Arg Glu Glu Met
            355                 360                 365
Thr Lys Asn Gln Val Ser Leu Thr Cys Leu Val Lys Gly Phe Tyr Pro
370             375                 380
Ser Asp Ile Ala Val Glu Trp Glu Ser Asn Gly Gln Pro Glu Asn Asn
385             390                 395                 400
Tyr Lys Thr Thr Pro Pro Met Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
            435                 440                 445
Lys Ser Leu Ser Leu Ser Pro Gly Lys
450                 455

<210> SEQ ID NO 21
<211> LENGTH: 700
<212> TYPE: DNA
<213> ORGANISM: Artificial Sequence
<220> FEATURE:
<223> OTHER INFORMATION: RH2-59 Antibody Light Chain DNA Sequence

<400> SEQUENCE: 21
atgagtgtgc ccactcaggt cctggggttg ctgctgctgt ggcttacaga tgccagatgc       60
```

-continued

```
caggctgtgc tgactcagcc gtcctcagtg tctggggccc cagggcagag ggtcaccatc      120
tcctgcactg ggagcagctc caacatcggg gcaggttatg atgtacactg gtaccagcag      180
cttccaggaa cagcccccaa actcctcatc tatgctaaca ccaatcggcc ctcagggatc      240
cctgaccgat tctctggctc caagtctggc acctcggcct ccctggccat cactgggctc      300
cagactgagg atgaggctga ttattactgc cagtcctatg acaccagccc gagtgcctct      360
tatgtcttcg gaactgggac caagctgacc gtcctaggtc agcccaaggc caaccccacc      420
gtgaccctgt tccccccatc ttctgaggag ctgcaagcca acaaggccac cctggtgtgc      480
ctgatctctg acttctaccc tggcgctgtg acagtggcct ggaaggctga tggctctcct      540
gtgaaggctg gcgtggagac caccaagcca tctaagcagt ctaacaacaa gtatgctgcc      600
tcttcttacc tgtctctgac ccctgagcag tggaagagcc accggtctta ctcttgccag      660
gtgacccatg agggctctac agtggagaag acagtggccc                           700
```

```
<210> SEQ ID NO 22
<211> LENGTH: 238
<212> TYPE: PRT
<213> ORGANISM: Artificial Sequence
<220> FEATURE:
<223> OTHER INFORMATION: RH2-59 Antibody Light Chain Amino Acid Sequence

<400> SEQUENCE: 22

Met Ser Val Pro Thr Gln Val Leu Gly Leu Leu Leu Leu Trp Leu Thr
 1               5                  10                  15

Asp Ala Arg Cys Gln Ala Val Leu Thr Gln Pro Ser Ser Val Ser Gly
             20                  25                  30

Ala Pro Gly Gln Arg Val Thr Ile Ser Cys Thr Gly Ser Ser Ser Asn
         35                  40                  45

Ile Gly Ala Gly Tyr Asp Val His Trp Tyr Gln Gln Leu Pro Gly Thr
     50                  55                  60

Ala Pro Lys Leu Leu Ile Tyr Ala Asn Thr Asn Arg Pro Ser Gly Ile
 65                  70                  75                  80

Pro Asp Arg Phe Ser Gly Ser Lys Ser Gly Thr Ser Ala Ser Leu Ala
                 85                  90                  95

Ile Thr Gly Leu Gln Thr Glu Asp Glu Ala Asp Tyr Tyr Cys Gln Ser
            100                 105                 110

Tyr Asp Thr Ser Pro Ser Ala Ser Tyr Val Phe Gly Thr Gly Thr Lys
        115                 120                 125

Leu Thr Val Leu Gly Gln Pro Lys Ala Asn Pro Thr Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 23
```

```
<211> LENGTH: 1374
<212> TYPE: DNA
<213> ORGANISM: Artificial Sequence
<220> FEATURE:
<223> OTHER INFORMATION: RH2-59 Antibody Heavy Chain DNA Sequence

<400> SEQUENCE: 23
atggaatgga gctgggtctt tctcttcttc ctgtcagtaa ctacaggtgt ccactcggaa      60
gtgcagctgg tgcagtctgg ggctgaggtg aagaagcctg gggcctcagt gaaggtctcc     120
tgcaaggctt ctggatacac cttcaccgac tactatatac actgggtgcg acaggcccct     180
ggacaagggc ttgagtggat gggatggatc cactctaaca gtggcgccac aacctatgca     240
cagaagtttc aggccagggt caccatgagc agggacacgt ccagcagcac agcctacatg     300
gagttgagca gctgaatc tgacgacacg gccatgtatt tttgttcgag agaggactac     360
tggggcagag ggacaatggt caccgtctcg agtgcatcca ccaagggccc atccgtcttc     420
cccctggcgc cctgctccag gagcacctcc gagagcacag ccgccctggg ctgcctggtc     480
aaggactact cccccgaacc ggtgacggtg tcgtggaact caggcgccct gaccagcggc     540
gtgcacacct tccggctgt cctacagtcc tcaggactct actccctcag cagcgtggtg     600
accgtgacct ccagcaactt tggcacgcag acctacacct gcaacgtaga tcacaagccc     660
agcaacacca aggtggacaa gacagttgag cggaaatgct gcgtggagtg cccaccatgc     720
ccagcacctc cagtggccgg accatcagtc ttcctgttcc ccccaaaacc caaggacact     780
ctcatgatct cccggacccc tgaggtcacg tgcgtggtgg tggacgtgag ccaggaagac     840
cccgaggtcc agttcaactg gtacgtggat ggcgtggagg tgcataatgc caagacaaag     900
ccgcgggagg agcagttcaa cagcacgttc cgtgtggtca gcgtcctcac cgtcctgcac     960
caggactggc tgaacggcaa ggagtacaag tgcaaggtct ccaacaaagg cctcccgtcc    1020
tccatcgaga aaaccatctc caaaaccaaa gggcagcccc gagagccaca ggtgtacacc    1080
ctgcccccat cccgggagga gatgaccaag aaccaggtca gcctgacctg cctggtcaaa    1140
ggcttctacc ccagcgacat cgccgtggag tgggagagca atgggcagcc ggagaacaac    1200
tacaagacca cgcctcccat gctggactcc gacggctcct tcttcctcta cagcaagcta    1260
accgtggaca gagcaggtg gcagcagggg aatgtcttct catgctccgt gatgcatgag    1320
gctctgcaca accactacac acagaagagc ctctccctgt ctcctggtaa atga          1374

<210> SEQ ID NO 24
<211> LENGTH: 457
<212> TYPE: PRT
<213> ORGANISM: Artificial Sequence
<220> FEATURE:
<223> OTHER INFORMATION: RH2-59 Antibody Heavy Chain Amino Acid Sequence

<400> SEQUENCE: 24

Met Glu Trp Ser Trp Val Phe Leu Phe Phe Leu Ser Val Thr Thr Gly
  1               5                  10                  15

Val His Ser Glu Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Asp Tyr Tyr Ile His Trp Val Arg Gln Ala Pro Gly Gln Gly Leu
     50                  55                  60

Glu Trp Met Gly Trp Ile His Ser Asn Ser Gly Ala Thr Thr Tyr Ala
 65                  70                  75                  80

Gln Lys Phe Gln Ala Arg Val Thr Met Ser Arg Asp Thr Ser Ser Ser
```

|       |       |       | 85    |       |       |       | 90    |       |       |       | 95    |       |
|-------|-------|-------|-------|-------|-------|-------|-------|-------|-------|-------|-------|-------|

Thr Ala Tyr Met Glu Leu Ser Arg Leu Glu Ser Asp Asp Thr Ala Met
                    100                     105                     110

Tyr Phe Cys Ser Arg Glu Asp Tyr Trp Gly Arg Gly Thr Met Val Thr
            115                     120                     125

Val Ser Ser Ala Ser Thr Lys Gly Pro Ser Val Phe Pro Leu Ala Pro
130                     135                     140

Cys Ser Arg Ser Thr Ser Glu Ser Thr Ala Ala Leu Gly Cys Leu Val
145                     150                     155                     160

Lys Asp Tyr Phe Pro Glu Pro Val Thr Val Ser Trp Asn Ser Gly Ala
                    165                     170                     175

Leu Thr Ser Gly Val His Thr Phe Pro Ala Val Leu Gln Ser Ser Gly
            180                     185                     190

Leu Tyr Ser Leu Ser Ser Val Val Thr Val Thr Ser Ser Asn Phe Gly
                195                     200                     205

Thr Gln Thr Tyr Thr Cys Asn Val Asp His Lys Pro Ser Asn Thr Lys
    210                     215                     220

Val Asp Lys Thr Val Glu Arg Lys Cys Cys Val Glu Cys Pro Pro Cys
225                     230                     235                     240

Pro Ala Pro Pro Val Ala Gly Pro Ser Val Phe Leu Phe Pro Pro Lys
                    245                     250                     255

Pro Lys Asp Thr Leu Met Ile Ser Arg Thr Pro Glu Val Thr Cys Val
            260                     265                     270

Val Val Asp Val Ser Gln Glu Asp Pro Glu Val Gln Phe Asn Trp Tyr
                275                     280                     285

Val Asp Gly Val Glu Val His Asn Ala Lys Thr Lys Pro Arg Glu Glu
    290                     295                     300

Gln Phe Asn Ser Thr Phe Arg Val Val Ser Val Leu Thr Val Leu His
305                     310                     315                     320

Gln Asp Trp Leu Asn Gly Lys Glu Tyr Lys Cys Lys Val Ser Asn Lys
                    325                     330                     335

Gly Leu Pro Ser Ser Ile Glu Lys Thr Ile Ser Lys Thr Lys Gly Gln
            340                     345                     350

Pro Arg Glu Pro Gln Val Tyr Thr Leu Pro Pro Ser Arg Glu Glu Met
                355                     360                     365

Thr Lys Asn Gln Val Ser Leu Thr Cys Leu Val Lys Gly Phe Tyr Pro
    370                     375                     380

Ser Asp Ile Ala Val Glu Trp Glu Ser Asn Gly Gln Pro Glu Asn Asn
385                     390                     395                     400

Tyr Lys Thr Thr Pro Pro Met Leu Asp Ser Asp Gly Ser Phe Phe Leu
                    405                     410                     415

Tyr Ser Lys Leu Thr Val Asp Lys Ser Arg Trp Gln Gln Gly Asn Val
            420                     425                     430

Phe Ser Cys Ser Val Met His Glu Ala Leu His Asn His Tyr Thr Gln
                435                     440                     445

Lys Ser Leu Ser Leu Ser Pro Gly Lys
    450                     455

<210> SEQ ID NO 25
<211> LENGTH: 714
<212> TYPE: DNA
<213> ORGANISM: Artificial Sequence
<220> FEATURE:
<223> OTHER INFORMATION: RH2-80 Antibody Light Chain DNA Sequence

<400> SEQUENCE: 25

```
atgagtgtgc ccactcaggt cctggggttg ctgctgctgt ggcttacaga tgccagatgc    60
caggctgtgc tgactcagcc gtcctcagtg tctggggccc cagggcagag ggtctccatc   120
tcctgcactg ggagcagctc caacatcggg gcagcttatg atgtacactg gtaccagcag   180
cttccaggaa cagcccccag actcctcatc tatgttaaca acaatcggcc ctcagggggtc   240 cctgaccgat tctctggctc caagtcgggc acctcagcct ccctagtcat tgctgggctc   300
caggctgagg atgaggctga ttattactgc cagtcctatg acaatagtct gaatgcttat   360
gtcttcggaa ctgggaccaa gctgaccgtc ctaggtcagc ccaaggccaa ccccaccgtg   420
accctgttcc cccatcttc tgaggagctg caagccaaca aggccaccct ggtgtgcctg   480
atctctgact ctacccctgg cgctgtgaca gtggcctgga aggctgatgg ctctcctgtg   540
aaggctggcg tggagaccac caagccatct aagcagtcta acaacaagta tgctgcctct   600
tcttacctgt ctctgacccc tgagcagtgg aagagccacc ggtcttactc ttgccaggtg   660
acccatgagg gctctacagt ggagaagaca gtggcccccca cagagtgctc ttga         714
```

<210> SEQ ID NO 26
<211> LENGTH: 237
<212> TYPE: PRT
<213> ORGANISM: Artificial Sequence
<220> FEATURE:
<223> OTHER INFORMATION: RH2-80 Antibody Light Chain Amino Acid Sequence

<400> SEQUENCE: 26

```
Met Ser Val Pro Thr Gln Val Leu Gly Leu Leu Leu Leu Trp Leu Thr
 1               5                   10                  15

Asp Ala Arg Cys Gln Ala Val Leu Thr Gln Pro Ser Ser Val Ser Gly
                20                  25                  30

Ala Pro Gly Gln Arg Val Ser Ile Ser Cys Thr Gly Ser Ser Ser Asn
             35                  40                  45

Ile Gly Ala Ala Tyr Asp Val His Trp Tyr Gln Gln Leu Pro Gly Thr
         50                  55                  60

Ala Pro Arg Leu Leu Ile Tyr Val Asn Asn Asn Arg Pro Ser Gly Val
 65                  70                  75                  80

Pro Asp Arg Phe Ser Gly Ser Lys Ser Gly Thr Ser Ala Ser Leu Val
                 85                  90                  95

Ile Ala Gly Leu Gln Ala Glu Asp Glu Ala Asp Tyr Tyr Cys Gln Ser
            100                 105                 110

Tyr Asp Asn Ser Leu Asn Ala Tyr Val Phe Gly Thr Gly Thr Lys Leu
        115                 120                 125

Thr Val Leu Gly Gln Pro Lys Ala Asn Pro Thr Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Gly Ser Pro Val Lys Ala Gly Val Glu Thr Thr Lys Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

<210> SEQ ID NO 27
<211> LENGTH: 1374
<212> TYPE: DNA
<213> ORGANISM: Artificial Sequence
<220> FEATURE:
<223> OTHER INFORMATION: RH2-80 Antibody Heavy Chain DNA Sequence

<400> SEQUENCE: 27

```
atggaatgga gctgggtctt tctcttcttc ctgtcagtaa ctacaggtgt ccactcggag      60
gtgcagctgg tgcagtctgg ggctgaggtg aagaagcctg␣ggcctcagt gaaggtctcc     120
tgcaaggctt ctggatacac cttcaccgac tactatatac actgggtgcg acaggcccct     180
ggacaagggc ttgagtggat gggatggatc cactctaaca gtggcgccac aacctatgca     240
cagaagtttc aggccagggt caccatgagc agggacacgt ccagcagcac agcctacatg     300
gagttgagca ggctggaatc tgacgacacg gccatgtatt tttgttcgag agaggactac     360
tggggcaaag gacaatggt caccgtctcg agtgcatcca ccaagggccc atccgtcttc     420
cccctggcgc cctgctccag gagcacctcc gagagcacag ccgccctggg ctgcctggtc     480
aaggactact␣ccccgaacc␣ggtgacggtg␣tcgtggaact␣caggcgccct␣gaccagcggc     540
gtgcacacct tcccggctgt cctacagtcc tcaggactct actccctcag cagcgtggtg     600
accgtgacct␣ccagcaactt␣tggcacgcag␣acctacacct␣gcaacgtaga␣tcacaagccc     660
agcaacacca aggtggacaa gacagttgag cggaaatgct gcgtggagtg cccaccatgc     720
ccagcacctc cagtggccgg accatcagtc ttcctgttcc␣ccaaaaaacc caaggacact     780
ctcatgatct cccggacccc tgaggtcacg tgcgtggtgg tggacgtgag ccaggaagac     840
cccgaggtcc agttcaactg gtacgtggat ggcgtggagg tgcataatgc caagacaaag     900
ccgcgggagg agcagttcaa cagcacgttc cgtgtggtca gcgtcctcac cgtcctgcac     960
caggactggc tgaacggcaa ggagtacaag tgcaaggtct ccaacaaagg cctcccgtcc    1020
tccatcgaga aaaccatctc caaaaccaaa gggcagcccc gagagccaca ggtgtacacc    1080
ctgcccccat␣ccgggagga␣gatgaccaag␣aaccaggtca␣gcctgacctg␣cctggtcaaa    1140
ggcttctacc ccagcgacat cgccgtggag tgggagagca atgggcagcc ggagaacaac    1200
tacaagacca cgcctcccat gctggactcc gacggctcct tcttcctcta cagcaagcta    1260
accgtggaca agagcaggtg gcagcagggg aatgtcttct catgctccgt gatgcatgag    1320
gctctgcaca␣ccactacac␣acagaagagc␣ctctccctgt␣ctcctggtaa␣atga          1374
```

<210> SEQ ID NO 28
<211> LENGTH: 457
<212> TYPE: PRT
<213> ORGANISM: Artificial Sequence
<220> FEATURE:
<223> OTHER INFORMATION: RH2-80 Antibody Heavy Chain Amino Acid Sequence

<400> SEQUENCE: 28

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Ile His Trp Val Arg Gln Ala Pro Gly Gln Gly Leu
    50                  55                  60

Glu Trp Met Gly Trp Ile His Ser Asn Ser Gly Ala Thr Thr Tyr Ala
65                  70                  75                  80

```
Gln Lys Phe Gln Ala Arg Val Thr Met Ser Arg Asp Thr Ser Ser
                85                  90                  95

Thr Ala Tyr Met Glu Leu Ser Arg Leu Glu Ser Asp Asp Thr Ala Met
            100                 105                 110

Tyr Phe Cys Ser Arg Glu Asp Tyr Trp Gly Lys Gly Thr Met Val Thr
        115                 120                 125

Val Ser Ser Ala Ser Thr Lys Gly Pro Ser Val Phe Pro Leu Ala Pro
130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Thr Ser Ser Asn Phe Gly
        195                 200                 205

Thr Gln Thr Tyr Thr Cys Asn Val Asp His Lys Pro Ser Asn Thr Lys
    210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Phe Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 29
<211> LENGTH: 19
<212> TYPE: PRT
<213> ORGANISM: Artificial Sequence
<220> FEATURE:
<223> OTHER INFORMATION: Leader sequence for heavy chain
```

<400> SEQUENCE: 29

Met Glu Trp Ser Trp Val Phe Leu Phe Phe Leu Ser Val Thr Thr Gly
1               5                   10                  15

Val His Ser

<210> SEQ ID NO 30
<211> LENGTH: 20
<212> TYPE: PRT
<213> ORGANISM: Artificial Sequence
<220> FEATURE:
<223> OTHER INFORMATION: Leader sequence for light chain

<400> SEQUENCE: 30

Met Ser Val Pro Thr Gln Val Leu Gly Leu Leu Leu Leu Trp Leu Thr
1               5                   10                  15

Asp Ala Arg Cys
            20

<210> SEQ ID NO 31
<211> LENGTH: 36
<212> TYPE: DNA
<213> ORGANISM: Artificial Sequence
<220> FEATURE:
<223> OTHER INFORMATION: PCR primer, heavy chain forward

<400> SEQUENCE: 31
acaggtgtcc actcggaggt gcagctggtg cagtct                     36

<210> SEQ ID NO 32
<211> LENGTH: 36
<212> TYPE: DNA
<213> ORGANISM: Artificial Sequence
<220> FEATURE:
<223> OTHER INFORMATION: PCR primer, heavy chain reverse

<400> SEQUENCE: 32
gcccttggtg gatgcactcg agacggtgac cagggt                     36

<210> SEQ ID NO 33
<211> LENGTH: 36
<212> TYPE: DNA
<213> ORGANISM: Artificial Sequence
<220> FEATURE:
<223> OTHER INFORMATION: PCR primer, light chain forward

<400> SEQUENCE: 33
acagatgcca gatgccagtc tgtgttgacg cagccg                     36

<210> SEQ ID NO 34
<211> LENGTH: 36
<212> TYPE: DNA
<213> ORGANISM: Artificial Sequence
<220> FEATURE:
<223> OTHER INFORMATION: PCR primer, light chain reverse

<400> SEQUENCE: 34
gttggccttg ggctgactta aaacggtgag ctgggt                     36

<210> SEQ ID NO 35
<211> LENGTH: 266
<212> TYPE: PRT
<213> ORGANISM: Homo Sapien
<220> FEATURE:
<221> NAME/KEY: VARIANT
<222> LOCATION: (1)...(266)

<223> OTHER INFORMATION: Dkk-1 precursor

<400> SEQUENCE: 35

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 36
<211> LENGTH: 259
<212> TYPE: PRT
<213> ORGANISM: Homo Sapien
<220> FEATURE:
<221> NAME/KEY: VARIANT
<222> LOCATION: (1)...(259)
<223> OTHER INFORMATION: Dkk-2 precursor

<400> SEQUENCE: 36

Met Ala Ala Leu Met Arg Ser Lys Asp Ser Ser Cys Cys Leu Leu Leu
1               5                   10                  15

Leu Ala Ala Val Leu Met Val Glu Ser Ser Gln Ile Gly Ser Ser Arg
            20                  25                  30

Ala Lys Leu Asn Ser Ile Lys Ser Ser Leu Gly Gly Glu Thr Pro Gly
        35                  40                  45

Gln Ala Ala Asn Arg Ser Ala Gly Met Tyr Gly Leu Ala Phe Gly
    50                  55                  60

Gly Ser Lys Lys Gly Lys Asn Leu Gly Gln Ala Tyr Pro Cys Ser Ser

```
                65                  70                  75                  80
Asp Lys Glu Cys Glu Val Gly Arg Tyr Cys His Ser Pro His Gln Gly
                    85                  90                  95

Ser Ser Ala Cys Met Val Cys Arg Arg Lys Lys Arg Cys His Arg
                100                 105                 110

Asp Gly Met Cys Cys Pro Ser Thr Arg Cys Asn Asn Gly Ile Cys Ile
                115                 120                 125

Pro Val Thr Glu Ser Ile Leu Thr Pro His Ile Pro Ala Leu Asp Gly
            130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
                180                 185                 190

Phe Cys Cys Ala Arg His Phe Trp Thr Lys Ile Cys Lys Pro Val Leu
            195                 200                 205

His Gln Gly Glu Val Cys Thr Lys Gln Arg Lys Lys Gly Ser His Gly
            210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile

<210> SEQ ID NO 37
<211> LENGTH: 224
<212> TYPE: PRT
<213> ORGANISM: Homo Sapien
<220> FEATURE:
<221> NAME/KEY: VARIANT
<222> LOCATION: (1)...(224)
<223> OTHER INFORMATION: Dkk-4 precursor

<400> SEQUENCE: 37

Met Val Ala Ala Val Leu Leu Gly Leu Ser Trp Leu Cys Ser Pro Leu
1               5                   10                  15

Gly Ala Leu Val Leu Asp Phe Asn Asn Ile Arg Ser Ser Ala Asp Leu
                20                  25                  30

His Gly Ala Arg Lys Gly Ser Gln Cys Leu Ser Asp Thr Asp Cys Asn
            35                  40                  45

Thr Arg Lys Phe Cys Leu Gln Pro Arg Asp Glu Lys Pro Phe Cys Ala
50                  55                  60

Thr Cys Arg Gly Leu Arg Arg Arg Cys Gln Arg Asp Ala Met Cys Cys
65                  70                  75                  80

Pro Gly Thr Leu Cys Val Asn Asp Val Cys Thr Thr Met Glu Asp Ala
                85                  90                  95

Thr Pro Ile Leu Glu Arg Gln Leu Asp Glu Gln Asp Gly Thr His Ala
                100                 105                 110

Glu Gly Thr Thr Gly His Pro Val Gln Glu Asn Gln Pro Lys Arg Lys
            115                 120                 125

Pro Ser Ile Lys Lys Ser Gln Gly Arg Lys Gly Gln Glu Gly Glu Ser
            130                 135                 140

Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
```

```
                        165                 170                 175
Ser Arg Arg Gly His Lys Asp Thr Ala Gln Ala Pro Glu Ile Phe Gln
            180                 185                 190

Arg Cys Asp Cys Gly Pro Gly Leu Leu Cys Arg Ser Gln Leu Thr Ser
            195                 200                 205

Asn Arg Gln His Ala Arg Leu Arg Val Cys Gln Lys Ile Glu Lys Leu
            210                 215                 220

<210> SEQ ID NO 38
<211> LENGTH: 250
<212> TYPE: PRT
<213> ORGANISM: Maccaca Mulatta
<220> FEATURE:
<221> NAME/KEY: VARIANT
<222> LOCATION: (1)...(250)
<223> OTHER INFORMATION: Dkk-1 precursor

<400> SEQUENCE: 38

Met Met Ala Leu Gly Ala Ala Gly Ala Ala Arg Val Leu Val Ala Leu
  1               5                  10                  15

Ala Ala Ala Leu Gly Gly His Pro Leu Leu Gly Val Ser Ala Thr Asn
            20                  25                  30

Ser Val Leu Asn Ser Asn Ala Ile Lys Asn Leu Pro Pro Pro Gly Gly
            35                  40                  45

Ala Ala Gly His Pro Gly Ser Ala Val Ser Ala Ala Pro Ile Leu Tyr
     50                  55                  60

Pro Gly Gly Asn Lys Tyr Gln Thr Ile Asp Asn Tyr Pro Tyr Pro Cys
 65                  70                  75                  80

Ala Glu Asp Glu Glu Cys Gly Thr Asp Glu Tyr Ala Ser Pro Thr Arg
                 85                  90                  95

Gly Gly Asp Ala Gly Val Gln Ile Cys Leu Cys Arg Lys Arg Arg Lys
            100                 105                 110

Arg Cys Met Arg His Ala Met Cys Cys Gly Asn Tyr Cys Lys Asn Gly
            115                 120                 125

Ile Cys Val Ser Ser Asp Gln Asn Phe Arg Gly Glu Ile Glu Glu Thr
     130                 135                 140

Ile Thr Glu Ser Phe Gly Asn His Ser Thr Leu Asp Gly Tyr Ser Arg
145                 150                 155                 160

Arg Thr Thr Leu Ser Ser Met Tyr His Ser Lys Gly Gln Glu Gly Ser
                 165                 170                 175

Val Cys Leu Arg Ser Asp Cys Ala Thr Gly Leu Cys Cys Ala Arg His
            180                 185                 190

Phe Trp Ser Lys Cys Lys Pro Val Leu Lys Glu Gly Gln Val Cys Thr
            195                 200                 205

Lys His Arg Lys Gly Ser His Gly Leu Glu Ile Phe Gln Arg Cys Tyr
     210                 215                 220

Cys Gly Gly Leu Ser Cys Arg Ile Gln Lys Asp His His Gln Ala Ser
225                 230                 235                 240

Asn Ser Arg Leu His Thr Cys Gln Arg His
                 245                 250

<210> SEQ ID NO 39
<211> LENGTH: 1615
<212> TYPE: PRT
<213> ORGANISM: Homo Sapien
<220> FEATURE:
<221> NAME/KEY: VARIANT
<222> LOCATION: (1)...(1615)
<223> OTHER INFORMATION: LRP5
```

<400> SEQUENCE: 39

```
Met Glu Ala Ala Pro Gly Pro Pro Trp Pro Leu Leu Leu Leu Leu
 1               5                  10                  15

Leu Leu Leu Leu Ala Leu Cys Gly Cys Pro Ala Pro Ala Ala Ser
             20                  25                  30

Pro Leu Leu Leu Phe Ala Asn Arg Arg Asp Val Arg Leu Val Asp Ala
             35                  40                  45

Gly Gly Val Lys Leu Glu Ser Thr Ile Val Val Ser Gly Leu Glu Asp
         50                  55                  60

Ala Ala Ala Val Asp Phe Gln Phe Ser Lys Gly Ala Val Tyr Trp Thr
 65                  70                  75                  80

Asp Val Ser Glu Glu Ala Ile Lys Gln Thr Tyr Leu Asn Gln Thr Gly
                 85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
                115                 120                 125

Thr Asn Arg Ile Glu Val Ala Asn Leu Asn Gly Thr Ser Arg Lys Val
130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
                180                 185                 190

Asp Ile Tyr Trp Pro Asn Gly Leu Thr Ile Asp Leu Glu Glu Gln Lys
                195                 200                 205

Leu Tyr Trp Ala Asp Ala Lys Leu Ser Phe Ile His Arg Ala Asn Leu
        210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
                260                 265                 270

Glu Ile Leu Ser Ala Leu Tyr Ser Pro Met Asp Ile Gln Val Leu Ser
            275                 280                 285

Gln Glu Arg Gln Pro Phe Phe His Thr Arg Cys Glu Glu Asp Asn Gly
        290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
                340                 345                 350

Arg Arg Ile Ser Leu Asp Thr Pro Asp Phe Thr Asp Ile Val Leu Gln
            355                 360                 365

Val Asp Asp Ile Arg His Ala Ile Ala Ile Asp Tyr Asp Pro Leu Glu
370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415
```

```
Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
                500                 505                 510

Gln Glu Gly Lys Leu Tyr Trp Gly Asp Ala Lys Thr Asp Lys Ile Glu
            515                 520                 525

Val Ile Asn Val Asp Gly Thr Lys Arg Arg Thr Leu Leu Glu Asp Lys
530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
                580                 585                 590

Ala Val Asn Val Ala Lys Val Val Gly Thr Asn Pro Cys Ala Asp Arg
            595                 600                 605

Asn Gly Gly Cys Ser His Leu Cys Phe Phe Thr Pro His Ala Thr Arg
            610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
                660                 665                 670

Gly Val Lys Glu Ala Ser Ala Leu Asp Phe Asp Val Ser Asn Asn His
            675                 680                 685

Ile Tyr Trp Thr Asp Val Ser Leu Lys Thr Ile Ser Arg Ala Phe Met
            690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
            755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
                805                 810                 815

Arg Leu Tyr Trp Thr Asp Leu Asp Thr Asn Met Ile Glu Ser Ser Asn
                820                 825                 830

Met Leu Gly Gln Glu Arg Val Val Ile Ala Asp Asp Leu Pro His Pro
```

```
                835                 840                 845
Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895

Ser Ser Arg Gln Asp Gly Leu Asn Asp Cys Met His Asn Asn Gly Gln
                900                 905                 910

Cys Gly Gln Leu Cys Leu Ala Ile Pro Gly Gly His Arg Cys Gly Cys
                915                 920                 925

Ala Ser His Tyr Thr Leu Asp Pro Ser Ser Arg Asn Cys Ser Pro Pro
                930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
                980                 985                 990

Trp Val Asp Gly Arg Gln Asn Ile Lys Arg Ala Lys Asp Asp Gly Thr
                995                 1000                1005

Gln Pro Phe Val Leu Thr Ser Leu Ser Gln Gly Gln Asn Pro Asp Arg
                1010                1015                1020

Gln Pro His Asp Leu Ser Ile Asp Ile Tyr Ser Arg Thr Leu Phe Trp
1025                1030                1035                1040

Thr Cys Glu Ala Thr Asn Thr Ile Asn Val His Arg Leu Ser Gly Glu
                1045                1050                1055

Ala Met Gly Val Val Leu Arg Gly Asp Arg Asp Lys Pro Arg Ala Ile
                1060                1065                1070

Val Val Asn Ala Glu Arg Gly Tyr Leu Tyr Phe Thr Asn Met Gln Asp
                1075                1080                1085

Arg Ala Ala Lys Ile Glu Arg Ala Ala Leu Asp Gly Thr Glu Arg Glu
                1090                1095                1100

Val Leu Phe Thr Thr Gly Leu Ile Arg Pro Val Ala Leu Val Val Asp
1105                1110                1115                1120

Asn Thr Leu Gly Lys Leu Phe Trp Val Asp Ala Asp Leu Lys Arg Ile
                1125                1130                1135

Glu Ser Cys Asp Leu Ser Gly Ala Asn Arg Leu Thr Leu Glu Asp Ala
                1140                1145                1150

Asn Ile Val Gln Pro Leu Gly Leu Thr Ile Leu Gly Lys His Leu Tyr
                1155                1160                1165

Trp Ile Asp Arg Gln Gln Gln Met Ile Glu Arg Val Glu Lys Thr Thr
                1170                1175                1180

Gly Asp Lys Arg Thr Arg Ile Gln Gly Arg Val Ala His Leu Thr Gly
1185                1190                1195                1200

Ile His Ala Val Glu Glu Val Ser Leu Glu Glu Phe Ser Ala His Pro
                1205                1210                1215

Cys Ala Arg Asp Asn Gly Gly Cys Ser His Ile Cys Ile Ala Lys Gly
                1220                1225                1230

Asp Gly Thr Pro Arg Cys Ser Cys Pro Val His Leu Val Leu Leu Gln
                1235                1240                1245

Asn Leu Leu Thr Cys Gly Glu Pro Pro Thr Cys Ser Pro Asp Gln Phe
                1250                1255                1260
```

-continued

```
Ala Cys Ala Thr Gly Glu Ile Asp Cys Ile Pro Gly Ala Trp Arg Cys
1265                1270                1275                1280

Asp Gly Phe Pro Glu Cys Asp Asp Gln Ser Asp Glu Glu Gly Cys Pro
            1285                1290                1295

Val Cys Ser Ala Ala Gln Phe Pro Cys Ala Arg Gly Gln Cys Val Asp
        1300                1305                1310

Leu Arg Leu Arg Cys Asp Gly Glu Ala Asp Cys Gln Asp Arg Ser Asp
    1315                1320                1325

Glu Ala Asp Cys Asp Ala Ile Cys Leu Pro Asn Gln Phe Arg Cys Ala
1330                1335                1340

Ser Gly Gln Cys Val Leu Ile Lys Gln Gln Cys Asp Ser Phe Pro Asp
1345                1350                1355                1360

Cys Ile Asp Gly Ser Asp Glu Leu Met Cys Glu Ile Thr Lys Pro Pro
            1365                1370                1375

Ser Asp Asp Ser Pro Ala His Ser Ser Ala Ile Gly Pro Val Ile Gly
        1380                1385                1390

Ile Ile Leu Ser Leu Phe Val Met Gly Gly Val Tyr Phe Val Cys Gln
    1395                1400                1405

Arg Val Val Cys Gln Arg Tyr Ala Gly Ala Asn Gly Pro Phe Pro His
    1410                1415                1420

Glu Tyr Val Ser Gly Thr Pro His Val Pro Leu Asn Phe Ile Ala Pro
1425                1430                1435                1440

Gly Gly Ser Gln His Gly Pro Phe Thr Gly Ile Ala Cys Gly Lys Ser
            1445                1450                1455

Met Met Ser Ser Val Ser Leu Met Gly Gly Arg Gly Gly Val Pro Leu
        1460                1465                1470

Tyr Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser Pro
1490                1495                1500

Ala Thr Asp Pro Ser Leu Tyr Asn Met Asp Met Phe Tyr Ser Ser Asn
1505                1510                1515                1520

Ile Pro Ala Thr Val Arg Pro Tyr Arg Pro Tyr Ile Ile Arg Gly Met
            1525                1530                1535

Ala Pro Pro Thr Thr Pro Cys Ser Thr Asp Val Cys Asp Ser Asp Tyr
        1540                1545                1550

Ser Ala Ser Arg Trp Lys Ala Ser Lys Tyr Tyr Leu Asp Leu Asn Ser
    1555                1560                1565

Asp Ser Asp Pro Tyr Pro Pro Pro Thr Pro His Ser Gln Tyr Leu
    1570                1575                1580

Ser Ala Glu Asp Ser Cys Pro Pro Ser Pro Ala Thr Glu Arg Ser Tyr
1585                1590                1595                1600

Phe His Leu Phe Pro Pro Pro Ser Pro Cys Thr Asp Ser Ser
            1605                1610                1615

<210> SEQ ID NO 40
<211> LENGTH: 1613
<212> TYPE: PRT
<213> ORGANISM: Homo Sapien
<220> FEATURE:
<221> NAME/KEY: VARIANT
<222> LOCATION: (1)...(1613)
<223> OTHER INFORMATION: LRP6

<400> SEQUENCE: 40

Met Gly Ala Val Leu Arg Ser Leu Leu Ala Cys Ser Phe Cys Val Leu
1               5                   10                  15
```

```
Leu Arg Ala Ala Pro Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Lys Leu Tyr Trp Thr
            100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
            165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
```

```
                435                 440                 445
Arg Ala Ile Val Leu Asp Pro Met Val Gly Tyr Met Tyr Trp Thr Asp
450                 455                 460
Trp Gly Glu Ile Pro Lys Ile Glu Arg Ala Ala Leu Asp Gly Ser Asp
465                 470                 475                 480
Arg Val Val Leu Val Asn Thr Ser Leu Gly Trp Pro Asn Gly Leu Ala
                485                 490                 495
Leu Asp Tyr Asp Glu Gly Lys Ile Tyr Trp Gly Asp Ala Lys Thr Asp
                500                 505                 510
Lys Ile Glu Val Met Asn Thr Asp Gly Thr Gly Arg Arg Val Leu Val
                515                 520                 525
Glu Asp Lys Ile Pro His Ile Phe Gly Phe Thr Leu Leu Gly Asp Tyr
530                 535                 540
Val Tyr Trp Thr Asp Trp Gln Arg Arg Ser Ile Glu Arg Val His Lys
545                 550                 555                 560
Arg Ser Ala Glu Arg Glu Val Ile Ile Asp Gln Leu Pro Asp Leu Met
                565                 570                 575
Gly Leu Lys Ala Thr Asn Val His Arg Val Ile Gly Ser Asn Pro Cys
                580                 585                 590
Ala Glu Glu Asn Gly Gly Cys Ser His Leu Cys Leu Tyr Arg Pro Gln
                595                 600                 605
Gly Leu Arg Cys Ala Cys Pro Ile Gly Phe Glu Leu Ile Ser Asp Met
                610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Asn Val Ala Ile
                645                 650                 655
Pro Leu Thr Gly Val Lys Glu Ala Ser Ala Leu Asp Phe Asp Val Thr
                660                 665                 670
Asp Asn Arg Ile Tyr Trp Thr Asp Ile Ser Leu Lys Thr Ile Ser Arg
                675                 680                 685
Ala Phe Met Asn Gly Ser Ala Leu Glu His Val Val Glu Phe Gly Leu
690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
                740                 745                 750
Leu Ala Leu Asp Pro Ala Glu Gly Phe Met Tyr Trp Thr Glu Trp Gly
                755                 760                 765
Gly Lys Pro Lys Ile Asp Arg Ala Ala Met Asp Gly Ser Glu Arg Thr
                770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asn Met Leu Gly Leu Asn Arg Glu Val Ile Ala Asp Asp Leu
                820                 825                 830
Pro His Pro Phe Gly Leu Thr Gln Tyr Gln Asp Tyr Ile Tyr Trp Thr
                835                 840                 845
Asp Trp Ser Arg Arg Ser Ile Glu Arg Ala Asn Lys Thr Ser Gly Gln
850                 855                 860
```

-continued

```
Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
    930                 935                 940

Asn Arg Met Val Ile Asp Glu Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
                980                 985                 990

Gln Glu Asp Gly Ser Gln Gly Phe Thr Val Val Ser Ser Val Pro
            995                 1000                1005

Ser Gln Asn Leu Glu Ile Gln Pro Tyr Asp Leu Ser Ile Asp Ile Tyr
        1010                1015                1020

Ser Arg Tyr Ile Tyr Trp Thr Cys Glu Ala Thr Asn Val Ile Asn Val
1025                1030                1035                1040

Thr Arg Leu Asp Gly Arg Ser Val Gly Val Val Leu Lys Gly Glu Gln
                1045                1050                1055

Asp Arg Pro Arg Ala Ile Val Val Asn Pro Glu Lys Gly Tyr Met Tyr
            1060                1065                1070

Phe Thr Asn Leu Gln Glu Arg Ser Pro Lys Ile Glu Arg Ala Ala Leu
        1075                1080                1085

Asp Gly Thr Glu Arg Glu Val Leu Phe Phe Ser Gly Leu Ser Lys Pro
    1090                1095                1100

Ile Ala Leu Ala Leu Asp Ser Arg Leu Gly Lys Leu Phe Trp Ala Asp
1105                1110                1115                1120

Ser Asp Leu Arg Arg Ile Glu Ser Ser Asp Leu Ser Gly Ala Asn Arg
                1125                1130                1135

Ile Val Leu Glu Asp Ser Asn Ile Leu Gln Pro Val Gly Leu Thr Val
                1140                1145                1150

Phe Glu Asn Trp Leu Tyr Trp Ile Asp Lys Gln Gln Gln Met Ile Glu
        1155                1160                1165

Lys Ile Asp Met Thr Gly Arg Glu Gly Arg Thr Lys Val Gln Ala Arg
    1170                1175                1180

Ile Ala Gln Leu Ser Asp Ile His Ala Val Lys Glu Leu Asn Leu Gln
1185                1190                1195                1200

Glu Tyr Arg Gln His Pro Cys Ala Gln Asp Asn Gly Gly Cys Ser His
                1205                1210                1215

Ile Cys Leu Val Lys Gly Asp Gly Thr Thr Arg Cys Ser Cys Pro Met
                1220                1225                1230

His Leu Val Leu Leu Gln Asp Glu Leu Ser Cys Gly Glu Pro Pro Thr
        1235                1240                1245

Cys Ser Pro Gln Gln Phe Thr Cys Phe Thr Gly Glu Ile Asp Cys Ile
    1250                1255                1260

Pro Val Ala Trp Arg Cys Asp Gly Phe Thr Glu Cys Glu Asp His Ser
1265                1270                1275                1280

Asp Glu Leu Asn Cys Pro Val Cys Ser Glu Ser Gln Phe Gln Cys Ala
                1285                1290                1295
```

Ser Gly Gln Cys Ile Asp Gly Ala Leu Arg Cys Asn Gly Asp Ala Asn
                1300                1305                1310

Cys Gln Asp Lys Ser Asp Glu Lys Asn Cys Glu Val Leu Cys Leu Ile
        1315                1320                1325

Asp Gln Phe Arg Cys Ala Asn Gly Gln Cys Ile Gly Lys His Lys Lys
        1330                1335                1340

Cys Asp His Asn Val Asp Cys Ser Asp Lys Ser Asp Glu Leu Asp Cys
1345                1350                1355                1360

Tyr Pro Thr Glu Glu Pro Ala Pro Gln Ala Thr Asn Thr Val Gly Ser
                1365                1370                1375

Val Ile Gly Val Ile Val Thr Ile Phe Val Ser Gly Thr Val Tyr Phe
        1380                1385                1390

Ile Cys Gln Arg Met Leu Cys Pro Arg Met Lys Gly Asp Gly Glu Thr
        1395                1400                1405

Met Thr Asn Asp Tyr Val Val His Gly Pro Ala Ser Val Pro Leu Gly
        1410                1415                1420

Tyr Val Pro His Pro Ser Ser Leu Ser Gly Ser Leu Pro Gly Met Ser
1425                1430                1435                1440

Arg Gly Lys Ser Met Ile Ser Ser Leu Ser Ile Met Gly Gly Ser Ser
                1445                1450                1455

Gly Pro Pro Tyr Asp Arg Ala His Val Thr Gly Ala Ser Ser Ser Ser
        1460                1465                1470

Ser Ser Ser Thr Lys Gly Thr Tyr Phe Pro Ala Ile Leu Asn Pro Pro
        1475                1480                1485

Pro Ser Pro Ala Thr Glu Arg Ser His Tyr Thr Met Glu Phe Gly Tyr
        1490                1495                1500

Ser Ser Asn Ser Pro Ser Thr His Arg Ser Tyr Ser Tyr Arg Pro Tyr
1505                1510                1515                1520

Ser Tyr Arg His Phe Ala Pro Pro Thr Thr Pro Cys Ser Thr Asp Val
                1525                1530                1535

Cys Asp Ser Asp Tyr Ala Pro Ser Arg Arg Met Thr Ser Val Ala Thr
        1540                1545                1550

Ala Lys Gly Tyr Thr Ser Asp Leu Asn Tyr Asp Ser Glu Pro Val Pro
        1555                1560                1565

Pro Pro Pro Thr Pro Arg Ser Gln Tyr Leu Ser Ala Glu Glu Asn Tyr
        1570                1575                1580

Glu Ser Cys Pro Pro Ser Pro Tyr Thr Glu Arg Ser Tyr Ser His His
1585                1590                1595                1600

Leu Tyr Pro Pro Pro Pro Ser Pro Cys Thr Asp Ser Ser
                1605                1610

<210> SEQ ID NO 41
<211> LENGTH: 438
<212> TYPE: PRT
<213> ORGANISM: Artificial Sequence
<220> FEATURE:
<223> OTHER INFORMATION: RH1-10 Antibody Heavy Chain Amino Acid Sequence
      without leader

<400> SEQUENCE: 41

Gln Val Gln Leu Leu Gln Ser Ala Ala Glu Val Lys Lys Pro Gly Glu
1               5                   10                  15

Ser Leu Lys Ile Ser Cys Lys Gly Ser Gly Tyr Asp Phe Pro Gly Tyr
            20                  25                  30

Tyr Leu His Trp Val Arg Gln Ala Pro Gly Gln Gly Leu Glu Trp Met
        35                  40                  45

-continued

Gly Trp Ile Asn Ala Asn Ser Gly Ala Thr Asn Tyr Ala Gln Asn Phe
        50                  55                  60

Gln Gly Arg Val Thr Met Thr Arg Asp Thr Ser Ile Ser Ala Ala Tyr
 65                  70                  75                  80

Met Glu Leu Ser Ser Leu Arg Ser Asp Asp Thr Ala Val Tyr Tyr Cys
                 85                  90                  95

Thr Arg Glu Asp His Trp Gly Arg Gly Thr Thr Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Thr Ser Ser Asn Phe Gly Thr Gln Thr
            180                 185                 190

Tyr Thr Cys Asn Val Asp His Lys Pro Ser Asn Thr Lys Val Asp Lys
        195                 200                 205

Thr Val Glu Arg Lys Cys Cys Val Glu Cys Pro Pro Cys Pro Ala Pro
210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Phe Arg Val Val Ser Val Leu Thr Val Leu His Gln Asp Trp
290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Thr Lys Gly Gln Pro Arg Glu
                325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 42
<211> LENGTH: 217
<212> TYPE: PRT

<213> ORGANISM: Artificial Sequence
<220> FEATURE:
<223> OTHER INFORMATION: RH1-10 Antibody Light Chain Amino Acid Sequence without leader

<400> SEQUENCE: 42

```
Gln Ser Val Leu Thr Gln Pro Pro Ser Ala Ser Gly Ala Pro Gly Gln
 1               5                  10                  15

Arg Val Thr Ile Ser Cys Thr Gly Ser Ser Asn Ile Gly Ala Gly
             20                  25                  30

Tyr Asp Val His Trp Tyr Gln Gln Leu Pro Gly Ala Ala Pro Lys Leu
         35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
             85                  90                  95

Leu Ser Gly Tyr Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215
```

<210> SEQ ID NO 43
<211> LENGTH: 438
<212> TYPE: PRT
<213> ORGANISM: Artificial Sequence
<220> FEATURE:
<223> OTHER INFORMATION: RH2-59 Antibody Heavy Chain Amino Acid Sequence without leader

<400> SEQUENCE: 43

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Tyr Ile His Trp Val Arg Gln Ala Pro Gly Gln Gly Leu Glu Trp Met
         35                  40                  45

Gly Trp Ile His Ser Asn Ser Gly Ala Thr Thr Tyr Ala Gln Lys Phe
 50                  55                  60

Gln Ala Arg Val Thr Met Ser Arg Asp Thr Ser Ser Ser Thr Ala Tyr
 65                  70                  75                  80

Met Glu Leu Ser Arg Leu Glu Ser Asp Thr Ala Met Tyr Phe Cys
             85                  90                  95

Ser Arg Glu Asp Tyr Trp Gly Arg Gly Thr Met Val Thr Val Ser Ser
            100                 105                 110
```

```
Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Thr Ser Ser Asn Phe Gly Thr Gln Thr
                180                 185                 190

Tyr Thr Cys Asn Val Asp His Lys Pro Ser Asn Thr Lys Val Asp Lys
        195                 200                 205

Thr Val Glu Arg Lys Cys Cys Val Glu Cys Pro Pro Cys Pro Ala Pro
    210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
            245                 250                 255

Val Ser Gln Glu Asp Pro Glu Val Gln Phe Asn Trp Tyr Val Asp Gly
                260                 265                 270

Val Glu Val His Asn Ala Lys Thr Lys Pro Arg Glu Glu Gln Phe Asn
        275                 280                 285

Ser Thr Phe Arg Val Val Ser Val Leu Thr Val Leu His Gln Asp Trp
    290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Thr Lys Gly Gln Pro Arg Glu
            325                 330                 335

Pro Gln Val Tyr Thr Leu Pro Pro Ser Arg Glu Glu Met Thr Lys Asn
                340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
            405                 410                 415

Ser Val Met His Glu Ala Leu His Asn His Tyr Thr Gln Lys Ser Leu
                420                 425                 430

Ser Leu Ser Pro Gly Lys
        435

<210> SEQ ID NO 44
<211> LENGTH: 218
<212> TYPE: PRT
<213> ORGANISM: Artificial Sequence
<220> FEATURE:
<223> OTHER INFORMATION: RH2-59 Antibody Light Chain Amino Acid Sequence
      without leader

<400> SEQUENCE: 44

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Gly Thr Ala Pro Lys Leu
                35                  40                  45

Leu Ile Tyr Ala Asn Thr Asn Arg Pro Ser Gly Ile Pro Asp Arg Phe
 50                  55                  60

Ser Gly Ser Lys Ser Gly Thr Ser Ala Ser Leu Ala Ile Thr Gly Leu
 65                  70                  75                  80

Gln Thr Glu Asp Glu Ala Asp Tyr Tyr Cys Gln Ser Tyr Asp Thr Ser
                 85                  90                  95

Pro Ser Ala Ser Tyr Val Phe Gly Thr Gly Thr Lys Leu Thr Val Leu
                100                 105                 110

Gly Gln Pro Lys Ala Asn Pro Thr Val Thr Leu Phe Pro Pro Ser Ser
                115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Gly Ser Pro
145                 150                 155                 160

Val Lys Ala Gly Val Glu Thr Thr Lys Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Arg Ser Tyr Ser Cys Gln Val Thr His Glu Gly Ser Thr Val
                195                 200                 205

Glu Lys Thr Val Ala Pro Thr Glu Cys Ser
210                 215

<210> SEQ ID NO 45
<211> LENGTH: 438
<212> TYPE: PRT
<213> ORGANISM: Artificial Sequence
<220> FEATURE:
<223> OTHER INFORMATION: RH2-80 Antibody Heavy Chain Amino Acid Sequence
      without leader

<400> SEQUENCE: 45

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
                35                  40                  45

Gly Trp Ile His Ser Asn Ser Gly Ala Thr Thr Tyr Ala Gln Lys Phe
 50                  55                  60

Gln Ala Arg Val Thr Met Ser Arg Asp Thr Ser Ser Ser Thr Ala Tyr
65                  70                  75                  80

Met Glu Leu Ser Arg Leu Glu Ser Asp Asp Thr Ala Met Tyr Phe Cys
                 85                  90                  95

Ser Arg Glu Asp Tyr Trp Gly Lys Gly Thr Met Val Thr Val Ser Ser
                100                 105                 110

Ala Ser Thr Lys Gly Pro Ser Val Phe Pro Leu Ala Pro Cys Ser Arg
                115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

```
Leu Ser Ser Val Val Thr Val Thr Ser Ser Asn Phe Gly Thr Gln Thr
            180                 185                 190

Tyr Thr Cys Asn Val Asp His Lys Pro Ser Asn Thr Lys Val Asp Lys
            195                 200                 205

Thr Val Glu Arg Lys Cys Cys Val Glu Cys Pro Pro Cys Pro Ala Pro
210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
            245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
            275                 280                 285

Ser Thr Phe Arg Val Val Ser Val Leu Thr Val Leu His Gln Asp Trp
            290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Thr Lys Gly Gln Pro Arg Glu
            325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
            370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
            405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 46
<211> LENGTH: 217
<212> TYPE: PRT
<213> ORGANISM: Artificial Sequence
<220> FEATURE:
<223> OTHER INFORMATION: RH2-80 Antibody Light Chain Amino Acid Sequence
      without leader

<400> SEQUENCE: 46

Gln Ala Val Leu Thr Gln Pro Ser Ser Val Ser Gly Ala Pro Gly Gln
1               5                   10                  15

Arg Val Ser Ile Ser Cys Thr Gly Ser Ser Asn Ile Gly Ala Ala
            20                  25                  30

Tyr Asp Val His Trp Tyr Gln Gln Leu Pro Gly Thr Ala Pro Arg Leu
            35                  40                  45

Leu Ile Tyr Val Asn Asn Asn Arg Pro Ser Gly Val Pro Asp Arg Phe
50                  55                  60

Ser Gly Ser Lys Ser Gly Thr Ser Ala Ser Leu Val Ile Ala Gly Leu
65                  70                  75                  80

Gln Ala Glu Asp Glu Ala Asp Tyr Tyr Cys Gln Ser Tyr Asp Asn Ser
            85                  90                  95
```

```
Leu Asn Ala Tyr Val Phe Gly Thr Gly Thr Lys Leu Thr Val Leu Gly
            100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
        210                 215

<210> SEQ ID NO 47
<211> LENGTH: 112
<212> TYPE: PRT
<213> ORGANISM: Artificial Sequence
<220> FEATURE:
<223> OTHER INFORMATION: RH1-10 Antibody light chain variable region
      sequence

<400> SEQUENCE: 47

Gln Ser Val Leu Thr Gln Pro Pro Ser Ala Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Ala Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

<210> SEQ ID NO 48
<211> LENGTH: 113
<212> TYPE: PRT
<213> ORGANISM: Artificial Sequence
<220> FEATURE:
<223> OTHER INFORMATION: RH2-59 Antibody light chain variable region
      sequence

<400> SEQUENCE: 48

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Ala Asn Thr Asn Arg Pro Ser Gly Ile Pro Asp Arg Phe
    50                  55                  60
```

```
Ser Gly Ser Lys Ser Gly Thr Ser Ala Ser Leu Ala Ile Thr Gly Leu
 65                  70                  75                  80

Gln Thr Glu Asp Glu Ala Asp Tyr Tyr Cys Gln Ser Tyr Asp Thr Ser
                 85                  90                  95

Pro Ser Ala Ser Tyr Val Phe Gly Thr Gly Thr Lys Leu Thr Val Leu
            100                 105                 110

Gly

<210> SEQ ID NO 49
<211> LENGTH: 112
<212> TYPE: PRT
<213> ORGANISM: Artificial Sequence
<220> FEATURE:
<223> OTHER INFORMATION: RH2-80 Antibody light chain variable region
      sequence

<400> SEQUENCE: 49

Gln Ala Val Leu Thr Gln Pro Ser Ser Val Ser Gly Ala Pro Gly Gln
 1               5                  10                  15

Arg Val Ser Ile Ser Cys Thr Gly Ser Ser Asn Ile Gly Ala Ala
             20                  25                  30

Tyr Asp Val His Trp Tyr Gln Gln Leu Pro Gly Thr Ala Pro Arg Leu
             35                  40                  45

Leu Ile Tyr Val Asn Asn Arg Pro Ser Gly Val Pro Asp Arg Phe
         50                  55                  60

Ser Gly Ser Lys Ser Gly Thr Ser Ala Ser Leu Val Ile Ala Gly Leu
 65                  70                  75                  80

Gln Ala Glu Asp Glu Ala Asp Tyr Tyr Cys Gln Ser Tyr Asp Asn Ser
                 85                  90                  95

Leu Asn Ala Tyr Val Phe Gly Thr Gly Thr Lys Leu Thr Val Leu Gly
            100                 105                 110

<210> SEQ ID NO 50
<211> LENGTH: 336
<212> TYPE: DNA
<213> ORGANISM: Artificial Sequence
<220> FEATURE:
<223> OTHER INFORMATION: RH2-18 Antibody light chain variable region
      sequence

<400> SEQUENCE: 50
cagtctgtgc tgactcagcc accctcagcg tctggggccc cagggcagag ggtcaccatc     60
tcctgcactg ggagcagctc caacatcggg gctggttatg atgtacactg gtaccagcag    120
cttccaggag cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttattattgc cagtcctatg acagcagcct gagtggttat    300
gtcttcggaa ctgggaccaa ggtcaccgtc ctaggt                              336

<210> SEQ ID NO 51
<211> LENGTH: 336
<212> TYPE: DNA
<213> ORGANISM: Artificial Sequence
<220> FEATURE:
<223> OTHER INFORMATION: RH2-18 Antibody light chain variable region
      sequence

<400> SEQUENCE: 51
cagtctgtgt tgacgcagcc gccctcagtg tctggggccc cagggcagag ggtcaccatc     60
tcctgcactg ggagcagctc caacatcggg gcaggttatg atgtacactg gtaccagcag    120
```

```
cttccaggaa cagcccccaa actcctcatc tatggttaca gcaatcggcc ctcagggtc    180 cctgaccgat tctctggctc caagtctggc gcctcagcct cccctggccat cactgggctc   240 cggcctgacg atgaggctga ttactattgc cagtcctatg acaacagcct gagttcttat   300
gtcttcggag gtgggaccca gctcaccgtt ttaagt                              336
```

<210> SEQ ID NO 52
<211> LENGTH: 339
<212> TYPE: DNA
<213> ORGANISM: Artificial Sequence
<220> FEATURE:
<223> OTHER INFORMATION: RH2-59 Antibody light chain variable region
      sequence

<400> SEQUENCE: 52

```
caggctgtgc tgactcagcc gtcctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatgctaaca ccaatcggcc ctcagggatc   180
cctgaccgat tctctggctc caagtctggc acctcggcct cccctggccat cactgggctc   240 cagactgagg atgaggctga ttattactgc cagtcctatg acaccagccc gagtgcctct   300
tatgtcttcg gaactgggac caagctgacc gtcctaggt                           339
```

<210> SEQ ID NO 53
<211> LENGTH: 336
<212> TYPE: DNA
<213> ORGANISM: Artificial Sequence
<220> FEATURE:
<223> OTHER INFORMATION: RH2-80 Antibody light chain variable region
      sequence

<400> SEQUENCE: 53

```
caggctgtgc tgactcagcc gtcctcagtg tctggggccc cagggcagag ggtctccatc    60
tcctgcactg ggagcagctc caacatcggg gcagcttatg atgtacactg gtaccagcag   120
cttccaggaa cagcccccag actcctcatc tatgttaaca acaatcggcc ctcagggtc    180 cctgaccgat tctctggctc caagtcgggc acctcagcct cccctagtcat tgctgggctc   240 caggctgagg atgaggctga ttattactgc cagtcctatg acaatagtct gaatgcttat   300
gtcttcggaa ctgggaccaa gctgaccgtc ctaggt                              336
```

<210> SEQ ID NO 54
<211> LENGTH: 336
<212> TYPE: DNA
<213> ORGANISM: Artificial Sequence
<220> FEATURE:
<223> OTHER INFORMATION: RH1-10 Antibody heavy chain variable region
      sequence

<400> SEQUENCE: 54

```
caggtgcagc tgttgcagtc tgcagcagag gtgaaaaagc ccggggagtc tctgaagatc    60
tcctgtaagg gttctggata cgactttccc ggctactatc tgcactgggt gcgacaggcc   120
cctggacaag gccttgagtg gatgggctgg atcaacgcta acagtggtgc cacaaattat   180
gcacagaact tcagggcag ggtcaccatg accaggaca cgtccatcag cgcagcttac    240
atggagctga gcagcctgag atctgacgac acggccgtct attattgtac gagagaggac   300
cactggggcc gagggaccac ggtcaccgtc tcctca                              336
```

<210> SEQ ID NO 55

<211> LENGTH: 336
<212> TYPE: DNA
<213> ORGANISM: Artificial Sequence
<220> FEATURE:
<223> OTHER INFORMATION: RH2-18 Antibody heavy chain variable region sequence

<400> SEQUENCE: 55

| | | |
|---|---|---|
| gaggtgcagc tggtgcagtc tggggctgag gtgaagaagc ctggggcctc agtgaaggtc | 60 |
| tcctgcaagg cttctggata caccttcacc gactactata tacactgggt gcgacaggcc | 120 |
| cctggacaag gcttgagtg atgggatgg atccactcta acagtggcgc cacaacctat | 180 |
| gcacagaagt ttcaggccag ggtcaccatg agcagggaca cgtccagcag cacagcctac | 240 |
| atggagttga gcaggctgga atctgacgac acggccatgt attttgttc gagagaggac | 300 |
| tactggggcc aaggaacccct ggtcaccgtc tcgagt | 336 |

<210> SEQ ID NO 56
<211> LENGTH: 336
<212> TYPE: DNA
<213> ORGANISM: Artificial Sequence
<220> FEATURE:
<223> OTHER INFORMATION: RH2-59Antibody heavy chain variable region sequence

<400> SEQUENCE: 56

| | | |
|---|---|---|
| gaagtgcagc tggtgcagtc tggggctgag gtgaagaagc ctggggcctc agtgaaggtc | 60 |
| tcctgcaagg cttctggata caccttcacc gactactata tacactgggt gcgacaggcc | 120 |
| cctggacaag ggcttgagtg atgggatgg atccactcta acagtggcgc cacaacctat | 180 |
| gcacagaagt ttcaggccag ggtcaccatg agcagggaca cgtccagcag cacagcctac | 240 |
| atggagttga gcaggctgga atctgacgac acggccatgt attttgttc gagagaggac | 300 |
| tactggggca gagggacaat ggtcaccgtc tcgagt | 336 |

<210> SEQ ID NO 57
<211> LENGTH: 336
<212> TYPE: DNA
<213> ORGANISM: Artificial Sequence
<220> FEATURE:
<223> OTHER INFORMATION: RH2-80 Antibody heavy chain variable region sequence

<400> SEQUENCE: 57

| | | |
|---|---|---|
| gaggtgcagc tggtgcagtc tggggctgag gtgaagaagc ctggggcctc agtgaaggtc | 60 |
| tcctgcaagg cttctggata caccttcacc gactactata tacactgggt gcgacaggcc | 120 |
| cctggacaag ggcttgagtg atgggatgg atccactcta acagtggcgc cacaacctat | 180 |
| gcacagaagt ttcaggccag ggtcaccatg agcagggaca cgtccagcag cacagcctac | 240 |
| atggagttga gcaggctgga atctgacgac acggccatgt attttgttc gagagaggac | 300 |
| tactggggca agggacaat ggtcaccgtc tcgagt | 336 |

<210> SEQ ID NO 58
<211> LENGTH: 112
<212> TYPE: PRT
<213> ORGANISM: Artificial Sequence
<220> FEATURE:
<223> OTHER INFORMATION: RH1-10 Antibody heavy chain variable region sequence

<400> SEQUENCE: 58

Gln Val Gln Leu Leu Gln Ser Ala Ala Glu Val Lys Lys Pro Gly Glu
 1               5                  10                  15

Ser Leu Lys Ile Ser Cys Lys Gly Ser Gly Tyr Asp Phe Pro Gly Tyr
            20                  25                  30

Tyr Leu His Trp Val Arg Gln Ala Pro Gly Gln Gly Leu Glu Trp Met
        35                  40                  45

Gly Trp Ile Asn Ala Asn Ser Gly Ala Thr Asn Tyr Ala Gln Asn Phe
 50                  55                  60

Gln Gly Arg Val Thr Met Thr Arg Asp Thr Ser Ile Ser Ala Ala Tyr
65                  70                  75                  80

Met Glu Leu Ser Ser Leu Arg Ser Asp Asp Thr Ala Val Tyr Tyr Cys
            85                  90                  95

Thr Arg Glu Asp His Trp Gly Arg Gly Thr Thr Val Thr Val Ser Ser
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: RH2-59 Antibody heavy chain variable region
      sequence

<400> SEQUENCE: 59

Glu Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile His Ser Asn Ser Gly Ala Thr Thr Tyr Ala Gln Lys Phe
 50                  55                  60

Gln Ala Arg Val Thr Met Ser Arg Asp Thr Ser Ser Ser Thr Ala Tyr
65                  70                  75                  80

Met Glu Leu Ser Arg Leu Glu Ser Asp Asp Thr Ala Met Tyr Phe Cys
            85                  90                  95

Ser Arg Glu Asp Tyr Trp Gly Arg Gly Thr Met Val Thr Val Ser Ser
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: RH2-80 Antibody heavy chain variable region
      sequence

<400> SEQUENCE: 60

Glu Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile His Ser Asn Ser Gly Ala Thr Thr Tyr Ala Gln Lys Phe
 50                  55                  60

Gln Ala Arg Val Thr Met Ser Arg Asp Thr Ser Ser Ser Thr Ala Tyr
65                  70                  75                  80

Met Glu Leu Ser Arg Leu Glu Ser Asp Asp Thr Ala Met Tyr Phe Cys
            85                  90                  95

```
Ser Arg Glu Asp Tyr Trp Gly Lys Gly Thr Met Val Thr Val Ser Ser
            100                 105                 110
```

```
<210> SEQ ID NO 61
<211> LENGTH: 10
<212> TYPE: PRT
<213> ORGANISM: Artificial Sequence
<220> FEATURE:
<223> OTHER INFORMATION: RH1-10 LC CDR3

<400> SEQUENCE: 61

Gln Ser Tyr Asp Ser Ser Leu Ser Gly Tyr
  1               5                  10
```

```
<210> SEQ ID NO 62
<211> LENGTH: 7
<212> TYPE: PRT
<213> ORGANISM: Artificial Sequence
<220> FEATURE:
<223> OTHER INFORMATION: RH2-59 LC CDR2

<400> SEQUENCE: 62

Ala Asn Thr Asn Arg Pro Ser
  1               5
```

```
<210> SEQ ID NO 63
<211> LENGTH: 12
<212> TYPE: PRT
<213> ORGANISM: Artificial Sequence
<220> FEATURE:
<223> OTHER INFORMATION: RH2-59 LC CDR3

<400> SEQUENCE: 63

Gln Ser Tyr Asp Thr Ser Pro Ser Ala Ser Tyr Val
  1               5                  10
```

```
<210> SEQ ID NO 64
<211> LENGTH: 14
<212> TYPE: PRT
<213> ORGANISM: Artificial Sequence
<220> FEATURE:
<223> OTHER INFORMATION: RH2-80 LC CDR1

<400> SEQUENCE: 64

Thr Gly Ser Ser Ser Asn Ile Gly Ala Ala Tyr Asp Val His
  1               5                  10
```

```
<210> SEQ ID NO 65
<211> LENGTH: 7
<212> TYPE: PRT
<213> ORGANISM: Artificial Sequence
<220> FEATURE:
<223> OTHER INFORMATION: RH2-80 LC CDR2

<400> SEQUENCE: 65

Val Asn Asn Asn Arg Pro Ser
  1               5
```

```
<210> SEQ ID NO 66
<211> LENGTH: 11
<212> TYPE: PRT
<213> ORGANISM: Artificial Sequence
<220> FEATURE:
<223> OTHER INFORMATION: RH2-80 LC CDR3

<400> SEQUENCE: 66

Gln Ser Tyr Asp Asn Ser Leu Asn Ala Tyr Val
  1               5                  10
```

<210> SEQ ID NO 67
<211> LENGTH: 5
<212> TYPE: PRT
<213> ORGANISM: Artificial Sequence
<220> FEATURE:
<223> OTHER INFORMATION: RH1-10 HC CDR1

<400> SEQUENCE: 67

Gly Tyr Tyr Leu His
1               5

<210> SEQ ID NO 68
<211> LENGTH: 17
<212> TYPE: PRT
<213> ORGANISM: Artificial Sequence
<220> FEATURE:
<223> OTHER INFORMATION: RH1-10 HC CDR2

<400> SEQUENCE: 68

Trp Ile Asn Ala Asn Ser Gly Ala Thr Asn Tyr Ala Gln Asn Phe Gln
1               5                   10                  15

Gly

<210> SEQ ID NO 69
<211> LENGTH: 3
<212> TYPE: PRT
<213> ORGANISM: Artificial Sequence
<220> FEATURE:
<223> OTHER INFORMATION: RH1-10 HC CDR3

<400> SEQUENCE: 69

Glu Asp His
1

<210> SEQ ID NO 70
<211> LENGTH: 211
<212> TYPE: PRT
<213> ORGANISM: Cynomologous Monkey
<220> FEATURE:
<221> NAME/KEY: VARIANT
<222> LOCATION: (1)...(211)
<223> OTHER INFORMATION: Precursor DKK-4

<400> SEQUENCE: 70

Met Ala Ala Ala Val Leu Leu Gly Leu Ser Trp Leu Cys Ser Pro Leu
1               5                   10                  15

Ala Leu Val Leu Asp Phe Asn Asn Ile Arg Ser Ser Ala Asp Leu Gly
            20                  25                  30

Ala Arg Lys Gly Ser Gln Cys Leu Ser Asp Thr Asp Cys Asn Arg Lys
        35                  40                  45

Phe Cys Leu Gln Ser His Asn Glu Lys Pro Phe Cys Ala Cys Arg Gly
    50                  55                  60

Leu Gln Arg Arg Cys Gln Arg Asp Ala Met Cys Cys Gly Thr Leu Cys
65                  70                  75                  80

Met Asn Asp Val Cys Thr Thr Met Glu Asp Ala Pro Lys Leu Glu Arg
                85                  90                  95

Gln Leu Asp Glu Gln Asp Gly Thr His Ala Val Thr Thr Gly His Pro
            100                 105                 110

Val Gln Glu Asn Gln Pro Lys Arg Lys Ser Ile Lys Ser Gln Gly
        115                 120                 125

Arg Lys Gly Gln Glu Gly Glu Ser Leu Arg Thr Phe Asp Cys Gly Pro
    130                 135                 140

-continued

```
Gly Leu Cys Cys Ala Arg His Trp Thr Lys Ile Cys Lys Pro Val Leu
145                 150                 155                 160

Leu Glu Gly Gln Val Cys Arg Arg Gly His Lys Asp Thr Ala Gln Ala
            165                 170                 175

Pro Glu Ile Phe Gln Cys Asp Cys Gly Pro Gly Leu Leu Cys Arg Ser
            180                 185                 190

Gln Leu Thr Ser Gln Gln His Ala Arg Leu Arg Val Cys Gln Lys Ile
            195                 200                 205

Glu Lys Leu
    210

<210> SEQ ID NO 71
<211> LENGTH: 313
<212> TYPE: PRT
<213> ORGANISM: Artificial Sequence
<220> FEATURE:
<223> OTHER INFORMATION: Rhesus Dkk-2 Fusion protein
<220> FEATURE:
<221> NAME/KEY: VARIANT
<222> LOCATION: (1)...(158)
<223> OTHER INFORMATION: Rhesus Dkk-1 N-terminal
<220> FEATURE:
<221> NAME/KEY: VARIANT
<222> LOCATION: (159)...(274)
<223> OTHER INFORMATION: Rhesus Dkk-2 C-terminal
<220> FEATURE:
<221> NAME/KEY: VARIANT
<222> LOCATION: (275)...(313)
<223> OTHER INFORMATION: Myc and His epitope tags

<400> SEQUENCE: 71

Met Met Ala Leu Gly Ala Ala Gly Ala Ala Arg Val Leu Val Ala Leu
1               5                   10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
            115                 120                 125

Pro Gly Asn Tyr Cys Lys Asn Gly Ile Cys Val Ser Ser Asp Gln Asn
130                 135                 140

Asn Phe Arg Gly Glu Ile Glu Glu Thr Ile Thr Glu Ser Phe Gly Thr
145                 150                 155                 160

Arg His Arg Asp Arg Asn His Gly His Tyr Ser Asn His Asp Leu Gly
            165                 170                 175

Trp Gln Asn Leu Gly Arg Pro His Thr Lys Met Ser His Ile Lys Gly
            180                 185                 190

His Glu Gly Asp Pro Cys Leu Arg Ser Ser Asp Cys Ile Glu Gly Phe
            195                 200                 205

Cys Cys Ala Arg His Phe Trp Thr Lys Ile Cys Lys Pro Val Leu His
210                 215                 220
```

-continued

```
Gln Gly Glu Val Cys Thr Lys Gln Arg Lys Lys Gly Ser His Gly Leu
225                 230                 235                 240

Glu Ile Phe Gln Arg Cys Asp Cys Ala Lys Gly Leu Ser Cys Lys Val
                245                 250                 255

Trp Lys Asp Ala Thr Tyr Ser Ser Lys Ala Arg Leu His Val Cys Gln
            260                 265                 270

Lys Ile Glu Phe Cys Thr Tyr Pro Ala Gln Trp Arg Pro Leu Glu Ser
        275                 280                 285

Arg Gly Pro Phe Glu Gln Lys Leu Ile Ser Gly Gly Asp Leu Asn Met
    290                 295                 300

His Thr Glu His His His His His His
305                 310
```

ANTIBODIES SPECIFIC FOR DKK-1

CROSS REFERENCE TO RELATED APPLICATIONS

This application claims the benefit of U.S. Provisional Application No. 60/900,226, filed Feb. 8, 2007, the contents of which are incorporated herein by reference in their entirety.

BACKGROUND OF THE INVENTION (1) Field of the Invention

The present invention relates to antibodies and immunologically functional fragments thereof that selectively bind Dkk-1 and their use for treating a variety of different diseases including preventing or treating conditions relating to loss of bone mass or to stimulate production of new bone, as well as various non-bone related disorders.

(2) Description of Related Art

The skeletal disorder osteoporosis is the leading cause of morbidity in the elderly. Osteoporosis is characterized by bone loss resulting from an imbalance between bone resorption (destruction) and bone formation. This condition leads to an increased risk of bone fractures, which may occur following low levels of trauma. In the United States, there are currently about 20 million people with detectable fractures of the vertebrae due to osteoporosis. Mortality due to bone fractures is not uncommon among the elderly patient population.

Elderly, post-menopausal women are at the highest risk of developing osteoporosis due to a deficiency of estrogen, which is necessary for proper bone maintenance. Insufficient estrogen levels lead to increased production and longevity of destructive osteoclasts, which, in turn, leads to increased bone resorption. As a result, an average of 5% bone loss is observed in the vertebrae per year. Although less common, osteoporosis also affects elderly men. The existence of osteoporosis in elderly men may also be due, in part, to insufficient estrogen levels caused by a decrease in circulating testosterone.

Therapeutic strategies for overcoming bone loss include both the prevention of bone resorption and the stimulation of bone growth. The majority of therapeutic targets that have led to efficacious osteoporosis treatments fall into the former category. Thus, the first line of treatment/prevention of this condition has historically been the inhibition of bone resorption using compounds such as bisphosphonates, estrogens, selective estrogen receptor modulators (SERMs) and calcitonin. Because inhibition of bone resorption cannot restore bone mass, this approach is an ineffective treatment for patients who have already lost a significant amount of bone. Additionally, the effectiveness of osteoporosis treatments that function by this mechanism is not consistent across the skeletal anatomy because the rate of bone turnover differs from one site to another. For example, the bone turnover rate is higher in the trabecular bone of the vertebrae than in the cortex of the long bones; thus, bone resorption inhibitors are less effective in increasing hip bone mineral density (BMD) and preventing hip fracture. Therefore, osteoanabolic agents, which increase cortical/periosteal bone formation and bone mass at long bones, would address an unmet need in the treatment of osteoporosis, especially for patients with high risk of hip fractures.

One potential therapeutic target for metabolic disorders, including osteoporosis, is the low-density lipoprotein receptor related protein 5 (LRP5). LRP5 belongs to the low density lipoprotein receptor (LDLR) gene family of cell surface receptors, characterized by cysteine-rich, complement-type LDLR ligand binding domains. LRP5 was isolated based on its proximity to the locus of osteoporosis pseudoglioma syndrome (OPPG), an autosomal recessive disorder characterized by severe osteoporosis (Hey, et al. Gene 216: 103-111 (1998); U.S. Pat. Nos. 6,555,654 and 6,545,137). Additional support for the notion that LRP5 represents a therapeutic target for osteoporosis comes from the observation that loss of function mutations of LRP5 lead to OPPG (Gong et al, Cell 107: 513-523 (2001)).

Interestingly, aberrant expression of LRP5 is also associated with high bone mass trait (HBM), an autosomal dominant human genetic skeletal condition characterized by strikingly increased bone mass. Positional cloning of the HBM mutation demonstrated that HBM results from a G171V mutation of the LRP5 gene which leads to a gain of function (See for example, Little et al, Am. J. Hum. Genet. 70: 11-19 (2002); U.S. Pat. Nos. 6,770,461 and 6,780,609; U.S. Published Patent Application Nos. 20040038860 and 20050070699). These findings, together with the fact that null mutation of LRP5 in mice results in severe bone loss (Kato, J. Cell Biol. 157(2): 303-314 (2002)), demonstrated an essential role for LRP5 in bone formation and bone mass in humans.

Despite its specific role in stimulating bone growth, the LRP5 gene was shown to have a nearly ubiquitous expression profile. The mechanism by which activation of LRP5 leads to osteogenesis is not known. At the molecular level, it was recently shown that LRP5 and a closely related LRP6 are involved in Wnt signaling as co-receptors for Wnt. Wnt genes encode secreted proteins implicated in a diverse array of developmental and adult physiological processes, such as mediating cell growth and differentiation in the central nervous system. It was also shown that LRP5 and LRP6 are receptors for the secreted protein dickkopf-1 (Dkk-1) and that their association with Dkk-1 represses Wnt signaling (Mao et al., Nature 411: 321-325 (2001); Semenov et al, Curr. Biol., (2001); Bafico et al, Nat Cell Biol 3: 683-686 (2001)).

Dickkopf-1 (Dkk-1) is a secreted protein that participates in embryonic head induction and antagonizes Wnt (Glinka et al., Nature 391: 357-362 (1998)). The amino acid sequence of human Dkk-1 and nucleotides encoding it have been described (U.S. Pat. Nos. 6,344,541; 6844422; 7,057,017; Published Patent Application No. 20050069915; Krupnick et al., Gene 238: 301-313(1999)). Expression of Dkk-1 in human was thought to be restricted to placenta, suggesting a role for Dkk-1 in embryonic development (Krupnick et al., supra). Allen and colleagues (U.S. Published Patent Application No. 20040038860) describe assays relating to the interaction between LRP5, HBM or LRP6 with Dkk-1. Antibodies that bind Dkk-1 have been described in the aforementioned patents and patent applications and in U.S. Published patent Application Nos. 20050079173 and 20060127393.

Human Dkk-1 is a member of a Dickkopf gene family which includes Dkk-1, Dkk-2, Dkk-3, and Dkk4 (Krupnick et al., supra). Although Dkk-1 and Dkk-4 have been shown to suppress Wnt-induced secondary axis induction in Xenopus embryos, neither block axis induction triggered by Xenopus Dishevelled or Frizzled, suggesting that their Wnt inhibitory activity is upstream of Frizzled in the Wnt signaling pathway (Krupnick et al., supra). It has been suggested that Dkk-1 might have an inhibitory effect on bone formation, making them potential targets for the prevention or treatment of osteoporosis (Patel and Karensky, N. Eng. J. Med. 346: 1572-1573 (2002); Boyden et al., N. Eng. J. Med. 346: 1513-1521 (2002)). There is a need for reagents and methods that will selectively inhibit the interaction of Dkk-1 with LRP5/6 and thus stimulate the Wnt signaling pathway in bone with a corresponding increase in bone anabolism without cross reacting other members of the Dickkopf gene family.

BRIEF SUMMARY OF THE INVENTION

The present invention provides antibodies and immunologically functional fragments thereof that selectively bind Dkk-1. The antibodies and immunologically active fragments also block or reduce binding between Dkk-1 and LRP5 and/or LRP6, thereby stimulating at least one activity associated with Wnt signaling. In particular, the antibodies and immunologically functional fragments thereof selectively inhibit the interaction of Dkk-1 with LRP5/6 and thus stimulate the Wnt signaling pathway in bone with a corresponding increase in bone mass without detectable cross reaction with other members of the Dickkopf gene family. The antibodies and fragments include antibodies with a naturally occurring structure, as well as polypeptides that have an antigen binding domain (for example, a domain antibody). The antibodies and fragments can be used to treat a variety of different diseases including preventing or treating conditions relating to loss of bone mass or to stimulate production of new bone, as well as various non-bone related disorders. Nucleic acids molecules, vectors, and host cells useful in the production of the antibodies and selective binding agents are also provided.

Some of the antibodies and immunologically functional fragments that are provided include (a) one or more light chain (LC) complementary determining regions (CDRs) selected from the group consisting of (i) an LC CDR1 with at least 80% sequence identity to SEQ ID NO:12, (ii) an LC CDR2 with at least 80% sequence identity to SEQ ID NO:13; and (iii) an LC CDR3 with at least 80% sequence identity to SEQ ID NO:14; (b) one or more heavy chain (HC) CDRs selected from the group consisting of (i) an HC CDR1 with at least 80% sequence identity to SEQ ID NO:9; (ii) an HC CDR2 with at least 80% sequence identity to SEQ ID NO:10; and (iii) a HC CDR3 with at least 80% sequence identity to SEQ ID NO:11; or (c) one or more LC CDRs of (a) and one or more HC CDRs of (b).

Such antibodies or fragments can specifically bind a Dkk-1 polypeptide. Certain antibodies or fragments include one, two, three, four, five or all six of the forgoing CDRs.

The light chain and heavy chains of other antibodies or fragments are provided are as described above but have at least 90% sequence identity to the foregoing sequences. Still other antibodies or fragments thereof have a light chain in which CDR1 has the amino acid sequence as set forth in SEQ ID NO:12, CDR2 has the amino acid sequence as set forth in SEQ ID NO:13 and/or CDR3 has the amino acid sequence as set forth in SEQ ID NO:14. Some antibodies and fragments may also have a heavy chain in which CDR1 has the amino acid sequence as set forth in SEQ ID NO:9, CDR2 has the amino acid sequence as set forth in SEQ ID NO:10 and/or HC CDR3 has the amino acid sequence as set forth in SEQ ID NO:11. Particular antibodies or fragments include a light chain CDR3 with the amino acid sequence of SEQ ID NO:14 and/or a heavy chain CDR3 with the amino acid sequence of SEQ ID NO:11.

Further provided are antibodies and immunologically functional fragments that are include (a) a light chain variable region ($V_L$) having at least 80% sequence identity with SEQ ID NO:4; (b) a heavy chain variable region ($V_H$) having at least 80% sequence identity with SEQ ID NO:8; or (c) a $V_L$ of (a) and a $V_H$ of (b).

Further still, provided are antibodies or immunologically functional fragments that are similar in structure but the $V_L$ has at least 90% sequence identity with SEQ ID NO:4; and the $V_H$ has at least 90% sequence identity with SEQ ID NO:8. In particular antibodies or functional fragments, the $V_L$ has at least 95% sequence identity with SEQ ID NO:4; and the $V_H$ has at least 95% sequence identity with SEQ ID NO:8. In further still aspects, the antibodies or immunologically functional fragments include a $V_L$ that has the amino acid sequence of SEQ ID NO:4, and/or a $V_H$ that has the amino acid sequence of SEQ ID NO:8.

Some antibodies or fragments have a light chain that comprises or consists of the amino acid sequence of SEQ ID NO:2 or 3 and/or a heavy chain that comprises or consists of the amino acid sequence of SEQ ID NO:6 or 7.

Also included are antibodies or an immunologically functional fragments that specifically bind a mature human Dkk-1 protein consisting of amino acids 32-266 of SEQ ID NO:35 and having a tertiary structure established by a disulfide bond between cysteine residues 220 and 245, wherein the antibody binds to an epitope comprising in part a loop consisting of the amino acids between cysteine residues 201 and 210 of SEQ ID NO:35.

Further provided are antibodies or fragments that compete with an antibody such as those described above for specific binding to a Dkk-1 polypeptide. For example, some antibodies and fragments compete with an antibody that consists of two identical heavy chains and two identical light chains, wherein the heavy chains consist of the amino acid sequence set forth in SEQ ID NO:3 and the light chains consist of amino acid sequence set forth in SEQ ID NO:7.

The various antibodies and fragments that are provided can include a single light and/or heavy chain or a single variable light domain and/or a single variable heavy domain. Other antibodies and fragments include two light and/or two heavy chains. In those instances in which the antibody or fragment includes two light and/or heavy chains, the two light chains in some instances are identical to one another; likewise, the two heavy chains in some instances are identical. The antibodies that are provided may include, for example, monoclonal antibodies, a human antibody, a chimeric antibody, or a humanized antibody. The immunologically functional fragments may include, but are not limited to, a scFv, a Fab, a Fab', a (Fab')$_2$, or a domain antibody. In some instances, the antibody or fragment dissociates from a Dkk-1 polypeptide with a Kd of about 269 pM or less.

Further provided are pharmaceutical compositions that include any of the foregoing antibodies and immunologically active fragments. Such compositions typically also include a buffer, a pharmaceutically acceptable diluent, a carrier, a solubilizer, an emulsifier, or a preservative. The use of the foregoing antibodies and immunologically active fragments in the preparation of a pharmaceutical composition or medicament is also described.

A variety of nucleic acids encoding the foregoing antibodies are also provided. Some nucleic acids, for instance, encode (a) a light chain CDR with the amino acid sequence as set forth in SEQ ID NO:14; and/or (b) a heavy chain CDR with the amino acid sequence as set forth in SEQ ID NO:11, such that the encoded CDR(s) encode an antibody or an immunologically functional fragment thereof that can specifically bind a Dkk-1 polypeptide. In particular aspects, the nucleic acids comprise or consist of a sequence that encodes a variable light region ($V_L$) and/or a variable heavy region ($V_H$) of an antibody or immunologically active fragment, wherein the $V_L$ has at least 80%, 90% or 95% sequence identity with SEQ ID NO:4 and the $V_H$ has at least 80%, 90%, or 95% sequence identity with SEQ ID NO:8. Some of the nucleic acids include a sequence that encodes a $V_L$ that comprises or consists of SEQ ID NO:4 and/or a sequence that encodes a $V_H$ that comprises or consists of SEQ ID NO:8. Still other nucleic acids include sequences that encode both a $V_L$ or $V_H$ with the foregoing sequence characteristics. Expression vectors comprising the foregoing nucleic acids are also disclosed herein, as are cells (for example, lower eukaryotic cells such as yeast cells or higher eukaryote cells such as mammalian cells such as CHO cells or insect cells) that comprise such expression vectors. Methods of producing an antibody or an immunologically active fragment thereof by culturing cells that contain such expression vectors are also described.

In another aspect, the use of the foregoing antibodies or immunologically functional fragments in the treatment of a variety of diseases is disclosed. In particular methods, an effective amount of an antibody or immunologically active fragment as described herein is administered to an individual in need thereof to treat osteoporosis, arthritis, multiple myeloma, metastatic bone disease, periodontal disease, diseases responsive to stem cell renewal, inflammatory diseases, neurological diseases, ocular diseases, renal diseases, pulmonary diseases, and skin diseases. Some treatment methods involve treating rheumatoid arthritis, psoriatic arthritis or osteoarthritis.

Further provided herein are methods of treating or preventing loss of bone mass comprising administering to an individual in need thereof a therapeutically effective amount of an antibody or immunologically functional fragment thereof as described herein. In a particular aspect, the individual is one that suffers from osteoporosis or other bone loss disease or disorder, for example, osteopenia, Paget's disease, periodontitis, rheumatoid arthritis, and bone loss due to immobilization. In a further aspect of this embodiment, the individual is one who suffers from cancer that metastasizes to bone, and in another aspect, the patient is one who suffers from multiple myeloma.

Methods of inducing or stimulating increased bone mass are also disclosed. Such methods involve administering to an individual a therapeutically effective amount of an antibody or immunologically functional fragment thereof as disclosed herein. In one aspect, the individual suffers from cancer that metastasizes to bone, and in another aspect, the patient suffers from multiple myeloma. In yet another aspect, the individual is selected from those who have osteoporosis, osteopenia, Paget's disease, periodontitis, rheumatoid arthritis, psoriatic arthritis, ankylosing spondylitis, and bone loss due to immobilization. In an additional aspect of this method, the individual is a bone graft recipient or one who suffers from a bone fracture.

The Dkk-1 antibodies and immunologically functional fragments thereof disclosed herein may provide a therapeutic treatment for alleviating the bone-destructive effects of cancer cells (for example, multiple myeloma, breast cancer, prostate cancer, and the like) invading the bone micro-environment.

In light of the above, further provided is a method of inducing Wnt activity in an individual comprising administering to the individual a therapeutically effective amount of an antibody or immunologically functional fragment thereof as described herein.

DEFINITIONS

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD and IgE, respectively.

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, $IgG_1$, $IgG_2$, $IgG_3$ and $IgG_4$. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the $C_H2$ domain of the heavy chain immunoglobulin constant region which comprises an N-linked glycosylation site of the $C_H2$ domain, or a variant thereof. In addition, these terms can refer to an antibody fragment of at least the Fab region that at least contains an N-linked glycosylation site.

The term "Fc" fragment refers to the 'fragment crystallized' C-terminal region of the antibody containing the $C_H2$ and $C_H3$ domains (FIG. 1). The term "Fab" fragment refers to the 'fragment antigen binding' region of the antibody containing the $V_H$, $C_H1$, $V_L$ and $C_L$ domains (See FIG. 1).

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be synthesized by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies herein can be made by the hybridoma method first described by Kohler et al., (1975) Nature, 256: 495, or may be made by recombinant DNA methods (See, for example, U.S. Pat. No. 4,816,567).

The term "fragments" within the scope of the terms "antibody" or "immunoglobulin" include those produced by digestion with various proteases, those produced by chemical cleavage and/or chemical dissociation and those produced recombinantly, so long as the fragment remains capable of specific binding to a target molecule. Among such fragments are Fc, Fab, Fab', Fv, F(ab')2, and single chain Fv (scFv) fragments. Hereinafter, the term "immunoglobulin" also includes the term "fragments" as well.

Immunoglobulins further include immunoglobulins or fragments that have been modified in sequence but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (See, for example, Intracellular Antibodies: Research and Disease Applications, (Marasco, ed., Springer-Verlag New York, Inc., 1998).

The term "epitope" refers to a site on an antigen to which B and/or T cells respond or a site on a molecule against which an antibody will be produced and/or to which an antibody will bind. For example, an epitope can be recognized by an antibody defining the epitope. A linear epitope is an epitope wherein an amino acid primary sequence comprises the epitope recognized. A linear epitope typically includes at least 3, and more usually, at least 5, for example, about 8 to about 10 amino acids in a unique sequence. A conformational epitope, in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope encompasses an increased number of amino acids relative to a linear epitope. With regard to recognition of conformational epitopes, the antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize the epitope.

Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology (1996) Vol. 66, Morris (Ed.).

As used herein, the term "Dkk-1" includes, for example, rhesus monkey, murine, and human forms of Dkk-1. The amino acid sequences for the human and Rhesus monkey Dkk-1 proteins are shown, respectively, in SEQ ID NOS:35 and 38. The human Dkk-1 protein (SEQ ID NO:35) has a leader sequence consisting of amino acids 1-31 of SEQ ID NO:35. The murine Dkk-1 protein sequence has been disclosed in Glinka, et al., Nature 391: 357-362 (1998). The Rhesus monkey Dkk-1 has been disclosed in International Publication No. WO2005049640. The term "Dkk-1" also includes variants of such native sequences that are immunologically cross-reactive with these native proteins. These Dkk-1 proteins can inhibit the interaction between LRP5 or LRP6 proteins with Wnt. An exemplary amino acid sequence for the human LRP5 is given in SEQ ID NO:39. An exemplary amino acid sequence encoding human LRP6 is given in SEQ ID NO:40. The term can also refer to a fragment of a native or variant form of Dkk-1 that contains an epitope to which the antibody disclosed herein can specifically bind.

The term "osteopenia" refers to a patient with bone loss of at least one standard deviation compared with a standard patient considered to have normal bone mineral density (BMD). For present purposes, the measurement is determined by Dual Energy X-ray Absorptiometry (DEXA) and the patient's BMD is compared with an age and gender-matched standard (Z score). In determining osteopenia, BMD measurements may be taken of one or more bones.

The term "therapeutically effective amount" refers to the amount of an anti-Dkk-1 antibody determined to produce a therapeutic response in a mammal. Such therapeutically effective amounts are readily ascertained by one of ordinary skill in the art.

BRIEF DESCRIPTION OF THE DRAWINGS

FIG. 1C shows the amino acid sequences of the RH2-18 light chain and heavy chain amino acid sequences (SEQ ID NO:3 and SEQ ID NO:7, respectively). The leader sequences for the light and heavy chain sequences are not shown. The variable regions are shown in italics.

FIG. 1D shows the amino acid sequence of the light chain variable region (SEQ ID NO:4) aligned with the sequence for the region in the germline (SEQ ID NO:16). The three light chain (LC) complementary determining regions (CDRs) are underlined and the amino acid sequence differences in the frameworks between the variable region sequence in RH2-18 and the germline sequence are shown in bold-faced type.

FIG. 1E shows the amino acid sequence of the heavy chain variable region (SEQ ID NO:8) aligned with the sequence for the region in the germline (SEQ ID NO:15). The three heavy chain (HC) CDRs are underlined and the amino acid sequence differences in the frameworks between the variable region sequence in RH2-18 and the germline sequence are shown in bold-faced type.

Figure 1A:
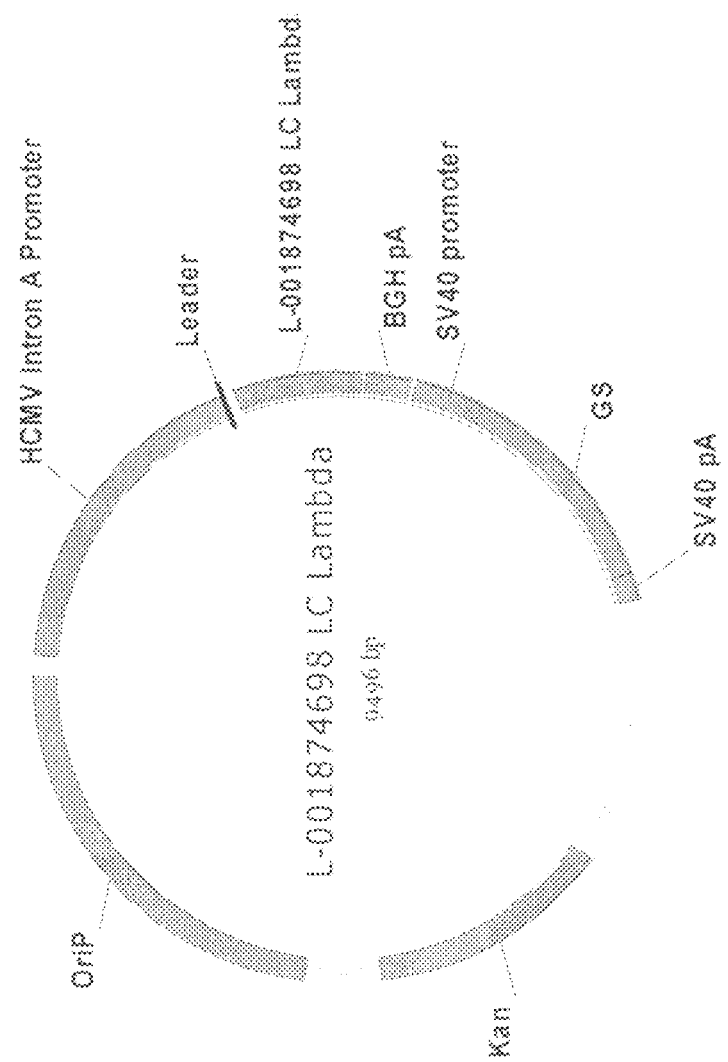
FIG. 1A shows a diagram of the plasmid encoding the RH2-18 light chain. OriP is the Epstein Barr virus origin of replication for expression in eukaryote cells. HCMV intron A promoter is the human cytomegalovirus promoter and first intron. LC Lambda encodes the light chain lambda constant region. Leader encodes a leader or signal sequence for secretion of the light chain polypeptide into the culture medium. BGH pA is the bovine growth hormone polyadenylation signal sequence. SV40 promoter is the SV40 virus promoter. GS is Glutamine synthase. SV40 is the SV40 polyadenylation signal sequence. Kan is the kanamycin gene for selection of the vector in E. coli.

Therefore fore, a variety of anti-Dkk-1 antibodies and immunologically functional fragments thereof, including single chain antibodies, domain antibodies, and polypeptides with an antigen binding region, useful for regulating the activity of Dkk-1 are provided. These anti-Dkk-1 antibodies and immunologically functional fragments thereof specifically bind to the human Dkk-1 polypeptide, relieve Dkk-1 inhibition of the Wnt signaling pathway, and induce bone formation in bone tissue.

In certain embodiments of the invention, the anti-Dkk-1 antibody is of the IgG1, IgG2 or IgG4 subtype. In preferred embodiments, the antibody is a fully human monoclonal antibody, which preferably does not provoke either antibody-dependent cellular cytotoxicity (ADCC), complement-mediated cytotoxicity (CMC), or form immune complexes to any extent, while retaining its normal pharmacokinetic (PK) properties. In a currently preferred embodiment, the antibody has an IgG2m4 isotype (See U.S. application Ser. No. 11/581, 931 filed Oct. 17, 2006 and U.S. application Ser. No. 11/256, 332 filed Oct. 21, 2005).

The variable regions of each light/heavy immunoglobulin chain pair comprising an antibody typically forms the antigen binding site. Variable regions of immunoglobulin chains generally exhibit the same overall structure consisting of relatively conserved framework regions (FR) joined by three hypervariable regions or "complementarily determining regions" (CDRs). The CDRs from the two chains of each heavy chain/light chain pair typically are aligned by the framework regions to form a structure that binds specifically with a specific epitope on the target protein. From the N-terminal to C-terminal of the immunological chain, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system has been described in Chothia and Lesk, J. Mol. Viol. 196: 901-917 (1987); Chothia et al., Nature 342: 878-883 (1989).

Specific examples of some of the full-length light and heavy immunoglobulin chains of the anti-Dkk-1 antibodies that are provided and their corresponding nucleotide and amino acid sequences are summarized in Table 1.

TABLE 1

Light and Heavy Chains

| Antibody Name | Chain Name | Chain Type | Nucleotide Sequence (SEQ ID NO:) | Amino Acid Sequence (SEQ ID NO) |
|---|---|---|---|---|
| RH1-10 | L1 | Light | 17 | 18 |
| RH2-18 | L2 | Light | 2 | 2 |
| RH2-59 | L3 | Light | 21 | 22 |
| RH2-80 | L4 | Light | 25 | 26 |
| RH1-10 | H1 | Heavy | 19 | 20 |
| RH2-18 | H2 | Heavy | 5 | 6 |
| RH2-59 | H3 | Heavy | 23 | 24 |
| RH2-80 | H4 | Heavy | 27 | 28 |

An anti-Dkk-1 antibody can be formed by combining any one of the light chains listed in Table 1 with any of the heavy chains listed in Table 1. In some instances, the antibody include at least one heavy chain and one light chain from those listed in Table 1 and in other instances, the antibody contains two identical light chains and two identical heavy chains. As an example, an antibody or immunologically functional fragment can include two L2 light chains and two Hi heavy chains, or two L2 light chains and two H3 heavy chains, or two L2 light chains and two H4 heavy chains and other similar combinations of pairs of light chains and pairs of heavy chains as listed in Table 1.

Exemplary anti-Dkk-1 antibodies capable of binding to the aforementioned multi-dimensional conformational epitope in the C-terminal region of Dkk-1 are the monoclonal antibodies RH1-10, RH2-18, RH2-59, and RH2-80 (see, examples below), each of which comprises a light chain and a heavy chain.

The complete light chain of RH1-10 is encoded by the nucleotide sequence shown in SEQ ID NO:17, and the complete heavy chain of RH1-10 by the nucleotide sequence shown in SEQ ID NO:19. The corresponding light and heavy chain amino acid sequences of RH1-10 are shown, respectively, in SEQ ID NOS:18 and 20. Amino acid residues 1 to 20 of SEQ ID NO:18 and residues 1 to 19 of SEQ ID NO:20 correspond to the signal sequences of these the light and heavy chains of RH1-10, respectively. The amino acid sequence of the light chain without the signal sequence is shown in SEQ ID NO:42, the amino acid sequence of the heavy chain lacking the signal sequence is shown in SEQ ID NO:41. Thus, in one aspect of the foregoing embodiment, the heavy chain may consist of amino acids 20 to 457 of SEQ ID NO:20 (H1 corresponding to SEQ ID NO:41), and in another aspect of this embodiment, the light chain may consist of amino acids 21 to 237 of SEQ ID NO:18 (L1 corresponding to SEQ ID NO:42). In yet another aspect of this embodiment, the antibody comprises both a heavy chain consisting of amino acids 20 to 457 of SEQ ID NO:20 and a light chain consisting of amino acids 21 to 237 of SEQ ID NO:18. In some instances, the antibody consists of two identical heavy chains each consisting of amino acids 20-457 of SEQ ID NO:20 and two identical light chains each consisting of amino acids 21 to 237 of SEQ ID NO:18.

The complete light chain of RH2-18 is encoded by the nucleotide sequence shown in SEQ ID NO:1, and the complete heavy chain of RH2-18 by the nucleotide sequence shown in SEQ ID NO:5. The corresponding light and heavy chain amino acid sequences of RH2-18 are shown, respectively, in SEQ ID NOS:2 and 6. Amino acid residues 1 to 20 of SEQ ID NO:2 and residues 1 to 19 of SEQ ID NO:6 correspond to the signal sequences of these the light and heavy chains of RH2-18, respectively. The amino acid sequence of the light chain without the signal sequence is shown in SEQ ID NO:3, the amino acid sequence of the heavy chain lacking the signal sequence is shown in SEQ ID NO:7. Thus, in one aspect of the foregoing embodiment, the heavy chain may consist of amino acids 20 to 457 of SEQ ID NO:6 (H2 corresponding to SEQ ID NO:7), and in another aspect of this embodiment, the light chain may consist of amino acids 21 to 237 of SEQ ID NO:2 (L2 corresponding to SEQ ID NO:3). In yet another aspect of this embodiment, the antibody comprises both a heavy chain consisting of amino acids 20 to 457 of SEQ ID NO:6 and a light chain consisting of amino acids 21 to 237 of SEQ ID NO:2. In some instances, the antibody consists of two identical heavy chains each consisting of amino acids 20-457 of SEQ ID NO:6 and two identical light chains each consisting of amino acids 21 to 237 of SEQ ID NO:2.

The complete light chain of RH2-59 is encoded by the nucleotide sequence shown in SEQ ID NO:21, and the complete heavy chain of RH2-59 by the nucleotide sequence shown in SEQ ID NO:23. The corresponding light and heavy chain amino acid sequences of RH2-59 are shown, respectively, in SEQ ID NOS:22 and 24. Amino acid residues 1 to 20 of SEQ ID NO:22 and residues 1 to 19 of SEQ ID NO:24 correspond to the signal sequences of these the light and heavy chains of RH2-59, respectively. The amino acid sequence of the light chain without the signal sequence is shown in SEQ ID NO:44, the amino acid sequence of the heavy chain lacking the signal sequence is shown in SEQ ID NO:43. Thus, in one aspect of the foregoing embodiment, the heavy chain may consist of amino acids 20 to 457 of SEQ ID NO:24 (H3 corresponding to SEQ ID NO:43), and in another aspect of this embodiment, the light chain may consist of amino acids 21 to 237 of SEQ ID NO:22 (L3 corresponding to SEQ ID NO:44). In yet another aspect of this embodiment, the antibody comprises both a heavy chain consisting of amino acids 20 to 457 of SEQ ID NO:24 and a light chain consisting of amino acids 21-237 of SEQ ID NO:22. In some instances, the antibody consists of two identical heavy chains each consisting of amino acids 20 to 457 of SEQ ID NO:24 and two identical light chains each consisting of amino acids 21 to 237 of SEQ ID NO:22.

The complete light chain of RH2-80 is encoded by the nucleotide sequence shown in SEQ ID NO:25, and the complete heavy chain of RH2-80 by the nucleotide sequence shown in SEQ ID NO:27. The corresponding light and heavy chain amino acid sequences of RH2-80 are shown, respectively, in SEQ ID NOS:26 and 28. Amino acid residues 1 to 20 of SEQ ID NO:26 and residues 1 to 19 of SEQ ID NO:28 correspond to the signal sequences of these the light and heavy chains of RH2-80, respectively. The amino acid sequence of the light chain without the signal sequence is shown in SEQ ID NO:46, the amino acid sequence of the heavy chain lacking the signal sequence is shown in SEQ ID NO:45. Thus, in one aspect of the foregoing embodiment, the heavy chain may consist of amino acids 20 to 457 of SEQ ID NO:28 (H4 corresponding to SEQ ID NO:45), and in another aspect of this embodiment, the light chain may consist of amino acids 21 to 237 of SEQ ID NO:26 (L4 corresponding to SEQ ID NO:46). In yet another aspect of this embodiment, the antibody comprises both a heavy chain consisting of amino acids 20 to 457 of SEQ ID NO:28 and a light chain consisting of amino acids 21 to 237 of SEQ ID NO:26. In some instances, the antibody consists of two identical heavy chains each consisting of amino acids 20 to 457 of SEQ ID NO:28 and two identical light chains each consisting of amino acids 21 to 237 of SEQ ID NO:26.

Other anti-Dkk-1 antibodies that are provided are variants of antibodies formed by any combination of the heavy and light chains disclosed above and comprise light and/or heavy chains that each have at least 70%, 75%, 80%, 85%, 90%, 95%, 97%, or 99% identity to the amino acid sequences of these light and heavy chains. In some instances, such antibodies include at least one heavy chain and one light chain, whereas in other instances such variant forms contain two identical light chains and two identical heavy chains.

Also provided are anti-Dkk-1 antibodies that comprise a light chain variable region selected from the group consisting of VL1, VL2, VL3, and VL4 and/or a heavy chain variable region selected from the group consisting of VH1, VH2, VH3, and VH4 as shown in Table 2 below, and immunologically functional fragments, derivatives, muteins and variants of these light chain and heavy chain variable regions.

TABLE 2

Variable Regions

| Antibody Name | Chain Name | Chain Type | Nucleotide Sequence (SEQ ID NO:) | Amino Acid Sequence (SEQ ID NO) |
|---|---|---|---|---|
| RH1-10 | VL1 | Light | 50 | 47 |
| RH2-18 | VL2 | Light | 51 | 4 |
| RH2-59 | VL3 | Light | 52 | 48 |
| RH2-80 | VL4 | Light | 53 | 49 |
| RH1-10 | VH1 | Heavy | 54 | 58 |
| RH2-18 | VH2 | Heavy | 55 | 8 |
| RH2-59 | VH3 | Heavy | 56 | 59 |
| RH2-80 | VH4 | Heavy | 57 | 60 |

Thus, the anti-Dkk-1 antibodies that are provided thus include, but are not limited to, those having the following form: VL1VH1, VL1VH2, VL1VH3, VL1VH4, VL2VH1, VL2VH2, VL2VH3, VL2VH4, VL3VH1, VL3VH2, VL3VH3, VL3VH4, VL4VH1, VL4VH2, VL4VH3, and VL4VH3. In some instances, the foregoing antibodies include two light chain variable region domains and two heavy chain variable region domains wherein each light chain is the same and each heavy chain is the same. In other instances, the foregoing antibodies include two light chain variable region domains and two heavy chain variable region domains wherein each light chain is different and each heavy chain is different.

As a specific example of such anti-Dkk-1 antibodies, particular antibodies or immunologically functional fragments thereof can comprise the variable region of the light chain or the variable region of the heavy chain of RH2-18, wherein the light chain variable region consists of amino acids 21 to 132 of SEQ ID NO:2 (VL1 corresponding to SEQ ID NO:4) and the heavy chain variable region consists of amino acids 20 to 131 of SEQ ID NO:6 (VH1 corresponding to SEQ ID NO:8). In one aspect of this embodiment, the antibody consists of two identical heavy chains and two identical light chains. Also provided, for instance, is an antibody comprising a light chain variable region that consists of amino acids 21 to 132 of SEQ ID NO:2 or an antigen-binding or an immunologically functional fragment thereof and further comprising a heavy chain variable region that consists of amino acids 20 to 131 of SEQ ID NO:6.

Particular anti-Dkk-1 antibodies can comprise a light chain variable domain comprising a sequence of ammo acids that differs from the sequence of a light chain variable domain selected from VL1, VL2, VL3, or VL4 from 1 up to about 20 amino acid residues, wherein each such sequence difference is independently either a deletion, insertion, or substitution of one amino acid. The light chain variable region in some antibodies comprises a sequence of amino acids that has at least 70%, 75%, 80%, 85%, 90%, 95%, 97%, or 99% sequence identity to the amino acid sequences of the light chain variable region of VL1, VL2, VL3, or VL4.

Particular anti-Dkk-1 antibodies can comprise a heavy chain variable domain comprising a sequence of amino acids that differs from the sequence of a heavy chain variable domain selected from VH1, VH2, VH3, or VH4 from 1 up to about 20 amino acid residues, wherein each such sequence difference is independently either a deletion, insertion, or substitution of one amino acid. The heavy chain variable region in some antibodies comprises a sequence of amino acids that has at least 70%, 75%, 80%, 85%, 90%, 95%, 97% or 99% sequence identity to the amino acid sequences of the heavy chain variable region of VH1, VH2, VH3, or VH4.

Particular anti-Dkk-1 antibodies that are disclosed herein can comprise one or more amino acid sequences that are identical or have substantial sequence identity to the amino acid sequences of one or more of the CDRs as summarized in Table 3.

TABLE 3

| | | CDRs | | |
|---|---|---|---|---|
| Antibody Name | Chain | CDR | Amino Acid Sequence | SEQ ID NO: |
| RH2-18 | Light | LC CDR1 | TGSSSNIGAGYDVH | 12 |
| RH2-18 | Light | LC CDR2 | GYSNRPS | 13 |
| RH2-18 | Light | LC CDR3 | QSYDNSLSSY | 14 |
| RH1-10 | Light | LC CDR1 | TGSSSNIGAGYDVH | 12 |
| RH1-10 | Light | LC CDR2 | GNSNRPS | 13 |
| RH1-10 | Light | LC CDR3 | QSYDSSLSGY | 61 |
| RH2-59 | Light | LC CDR1 | TGSSSNIGAGYDVH | 12 |
| RH2-59 | Light | LC CDR2 | ANTNRPS | 62 |
| RH2-59 | Light | LC CDR3 | QSYDTSPSASYV | 63 |
| RH2-80 | Light | LC CDR1 | TGSSSNIGAAYDVH | 64 |
| RH2-80 | Light | LC CDR2 | VNNNRPS | 65 |
| RH2-80 | Light | LC CDR3 | QSYDNSLNAYV | 66 |
| RH2-18 | Heavy | HC CDR1 | DYYIH | 9 |
| RH2-18 | Heavy | HC CDR2 | WIHSNSGATTYAQKFQA | 10 |
| RH2-18 | Heavy | HC CDR3 | EDY | 11 |
| RH1-10 | Heavy | HC CDR1 | GYYLH | 67 |
| RH1-10 | Heavy | HC CDR2 | WINANSGATNYAQNFQG | 68 |
| RH1-10 | Heavy | HC CDR3 | EDH | 69 |

TABLE 3-continued

| | | CDRs | | |
|---|---|---|---|---|
| Antibody Name | Chain | CDR | Amino Acid Sequence | SEQ ID NO: |
| RH2-59 | Heavy | HC CDR1 | DYYIH | 9 |
| RH2-59 | Heavy | HC CDR2 | WIHSNSGATTYAQKFQA | 10 |
| RH2-59 | Heavy | HC CDR3 | EDY | 11 |
| RH2-80 | Heavy | HC CDR1 | DYYIH | 9 |
| RH2-80 | Heavy | HC CDR2 | WIHSNSGATTYAQKFQA | 10 |
| RH2-80 | Heavy | HC CDR3 | EDY | 11 |

The anti-Dkk-1 antibodies and immunological functional fragments that are provided can include one or more of the CDRs listed above and can include any combination of the CDRs. For example, some antibodies or fragments can include both the light chain CDR3 and the heavy chain CDR3. Certain antibodies have variant forms of the CDRs listed in Table 3, with one or more of the CDRs each having at least 80%, 85%, 90% or 95% sequence identity to a CDR sequence listed in Table 3. For example, the antibody or fragment can include both a light chain CDR3 and a heavy chain CDR3 that each have at least 80%, 85%, 90% or 95% sequence identity to the light chain CDR3 sequence and the heavy chain CDR3, respectively, listed in Table 3. Differences from the listed sequences usually are conservative substitutions. Polypeptides comprising one or more of the light or heavy chain CDRs may be produced by using a suitable vector to express the polypeptides in a suitable host cell as described in greater detail below.

The heavy and light chain variable regions and the CDRs that are disclosed in Table 2 and 3 can be used to prepare any of the various types of immunologically functional fragments that are known in the art including, but not limited to, domain antibodies, Fab fragments, Fab' fragments, F(ab'): fragments, Fv: fragments, single-chain antibodies and scFvs.

Anti-Dkk-1 Antibody Epitope

The anti-Dkk-1 antibodies bind to a complex multi-dimensional conformational epitope in the C-terminus region of the Dkk-1. The C-terminal domain of Dkk-1 is predicted to form a globular tertiary structure by homology model with colipase (as described below). The results shown in Example 5 indicate that the epitope recognized by the anti-Dkk-1 antibodies as exemplified by the RH2-18 antibody is a complex epitope affected by both sequence and tertiary structure of Dkk-1 in its cysteine-rich-domain-2 in the C-terminus. FIG. 5C shows a structural-homology model of Dkk-1 C-terminal domain (amino acid residues 187 to 266) indicating the amino acid residues necessary for binding of Dkk-1 to the RH2-18 antibody as determined by alanine-scanning (See FIG. 5C). Substitutions of amino acid residues $S_{187}$ to $V_{188}$, $R_{203}$ through $K_{208}$, $E_{24}$, and $L_{243}$ were found to result in diminished antigen-antibody interaction in immunoblotting experiments using non-denatured protein. Thus, these amino acid residues appear to play an important role in the formation of the complex epitope. Amino acid residues $R_{171}$ to $L_{174}$, which are outside the amino acid sequence shown in the C-terminal homology model, were also found to contribute to the complex epitope. In addition, substituting amino acid $C_{220}$ with alanine also resulted in a loss of RH2-18 binding to Dkk-1. However, specific substitutions of the amino acid residues as indicated in FIG. 5*c* mapping to the second and third fingers (loops) of the Dkk-1 C-terminal domain did not appear to adversely affect binding of RH2-18 to Dkk-1 and, therefore, are not considered necessary for the binding of RH2-18 to Dkk-1.

Thus, the RH2-18 antibody binds a complex epitope comprising amino acid residues from different discrete regions of the second cysteine-rich domain were identified as being necessary for antibody binding: amino acid residues $S_{187}$ and $V_{188}$, both in a region preceding the first finger domain, and amino acids $R_{203}$, $H_{204}$, $F_{205}$, $W_{206}$, $S_{207}$, and $K_{208}$, all of which comprise the first finger of the domain. Further towards the C-terminus of the domain, and preceding the second finger, are $E_{241}$ and $L_{243}$, which were also required for RH2-18 binding to Dkk-1. Finally, $Cys_{220}$ is necessary for RH2-18 binding to Dkk-1. Cys220 is predicted to play an important role in establishing a proper tertiary structure, again an indication of the complex nature of this epitope. Together, the data suggest that RH2-18 epitope is defined by a topographical surface of Dkk-1 C-terminal region that includes but is not limited to the first finger domain $A_{202}$-$I_{209}$ of Dkk-1. Thus, the anti-Dkk-1 antibodies bind to a complex epitope of mature human Dkk-1 protein consisting of amino acids 32-266 of SEQ ID NO:35 and having a tertiary structure established by a disulfide bond between cysteine residues 220 and 245, wherein the antibody binds to an epitope comprising a loop consisting of the amino acids between cysteine residues 201 and 210 of SEQ ID NO:35

The Dkk-1 amino acid sequence is closely related to that of Dkk-2 and Dkk-4 with 50% and 45% identity at the amino acid-level, respectively. A comparison of the amino acid sequences of human Dkk-1, -2, -4, and Rhesus monkey Dkk-1 (FIG. 6A) shows a lack of conservation of amino acid residues located within Dkk-1 that were identified as important for RH2-18 binding to Dkk-1 as described above. The amino acid residues in Dkk-1 that are necessary for RH2-18 binding are enclosed within the blue boxes. As can be seen, there is a complete lack of sequence conservation within the corresponding regions in Dkk-2 and Dkk-4. Based on the epitope mapping of amino acid residues in Dkk-1, which showed that amino acid residues Arg171 to Leu174, Ser187, Val188, Ser207, and Glu241 are necessary for binding of RH2-18 to Dkk-1 and based on the lack of sequence conservation between Dkk-1 and Dkk-2 and Dkk-4 at amino acid residues Arg171 to Leu174, Ser187, Val188, Ser207, and Glu241, RH2-18 and other anti-Dkk-1 antibodies sharing a similar epitope are predicted to have a high degree of selectivity for Dkk-1. As shown in Example 5, there was little or no detectable specific binding of RH2-18 to Dkk-2 or Dkk-4. Selectivity of the antibody towards Dkk-1 was minimally 100-fold and the detection limit for binding of RH2-18 to rhesus Dkk-1 was found to be about 1 ng. These data indicate RH2-18 antibody and similar anti-Dkk-1 antibodies described herein recognize a novel, complex, three-dimensional epitope covering several discrete regions of Dkk-1, which indicates that RH2-18 and the similar antibodies are unique.

Production of Anti-Dkk-1 Antibodies

The anti-Dkk-1 antibodies herein can be made by a hybridoma method first described by Kohler et al., (1975) Nature, 256:495, or may be made by recombinant DNA methods (See, for example, Example 1; U.S. Pat. No. 4,816,567). In a currently preferred aspect, the anti-Dkk-1 antibodies herein are made by recombinant DNA methods.

Recombinant DNA constructs encoding the anti-Dkk-1 antibodies herein can be used to transform lower eukaryote host cells such as yeast or filamentous fungi, plant host cells, mammalian host cells, insect host cells, or microbial host cells. Transformation can be performed using any known method for introducing nucleic acids into a host cell. The optimal transformation procedure used will depend upon the type of host cell being transformed.

Typical recombinant DNA expression constructs comprise a nucleic acid molecule encoding a polypeptide encoding the one or more of the following: a heavy chain constant region (for example, $C_H1$, $C_H2$ and/or $C_H3$); a heavy chain variable region; a light chain constant region; a light chain variable region; and, one or more CDRs of the light or heavy chain of the anti-Dkk-1 antibody. These nucleic acid sequences are inserted into an appropriate expression vector using standard ligation techniques. For example, in one embodiment, a nucleic acid encoding the RH2-18 heavy chain and a nucleic acid encoding the RH2-18 light chain are each ligated into an expression vector and each chain is separately expressed. Alternatively, a single nucleic acid encoding both the heavy and light chains joined by a peptide cleavage site such that after expression of the light and heavy chains as a single polypeptide, the peptide cleavage site is cleaved to produce separate light and heavy chains.

The expression vector is typically selected to be functional in the particular host cell employed. Suitable expression vectors can be purchased, for example, from Invitrogen Life Technologies or BD Biosciences. Other useful vectors for cloning and expressing the antibodies and fragments of the invention include those described in Bianchi and McGrew, Biotech. Biotechnol. Bioeng. 84(4):439-44 (2003). Additional suitable expression vectors are discussed, for example, in Methods Enzymol. 185 (D. V. Goeddel, ed.), 1990, New York: Academic Press.

Typically, expression vectors further include nucleic acid sequences for plasmid or virus maintenance and for cloning and expression of exogenous nucleotide sequences. These nucleic acid sequences typically include one or more of the following operatively-linked nucleotide expression sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a tag-encoding sequence located at the 5' or 3' end of the coding sequence and encoding a polyHis tag (such as hexaHis), or another tag for which commercially available antibodies exist, such as FLAG, HA (hemaglutinin from influenza virus), or myc. The tag can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

The nucleotide expression sequences in the expression vector may be homologous (from the same species or strain as the host cell), heterologous (from a species other than the host cell species or strain), hybrid (a combination of sequences from more than one source), synthetic, or native. As such, the source of an expression sequence may be any prokaryotic or eukaryotic organism. Expression sequences useful in the vectors may be obtained by any of several methods well known in the art. An origin of replication is typically a part of prokaryotic expression vectors, particularly those purchased commercially, and the origin aids in the amplification of the vector in a host cell. If the vector does not contain an origin of replication site, one may be chemically synthesized based on a known sequence, and ligated into the vector.

The expression vectors will typically contain a promoter that is recognized by the host organism and is operably linked to nucleic acid encoding the anti-Dkk-1 antibody thereof to produce the anti-Dkk-1 antibody. Promoters may be inducible promoters or constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding anti-Dkk-1 antibody by removing the promoter from the source DNA by restriction enzyme digestion or amplifying the promoter by polymerase chain reaction and inserting the desired promoter sequence into the vector. Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus40 (SV40). Other suitable mammalian promoters include heterologous mammalian promoters, for example, heat-shock promoters and the actin promoter. An enhancer sequence may be inserted into the vector to increase transcription in higher eukaryotes of a nucleic acid encoding an anti-Dkk-1 antibody. Enhancers are cis-acting elements of DNA, usually about 10 to 300 bp in length, that act on promoters to increase transcription. Enhancers are relatively orientation and position independent.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence.

A selectable marker gene element encodes a protein necessary for the survival and growth of a host cell grown in a selective culture medium. Typical selection marker genes used in expression vectors encode proteins that (a) confer resistance to antibiotics or other toxins, for example, ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, anti-Dkk-1 antibodies having particular glycosylation structures or patterns are desired. For example, many mammalian and plant cells will produce proteins with particular N-glycans that render the protein immunogenic when introduced into an individual. In the case of the anti-Dkk-1 antibodies where invoking an immune response against the anti-Dkk-1 antibodies is undesirable, it is preferred that the glycosylation pathway of the mammalian host cells be modified to produce anti-Dkk-1 antibodies without the undesirable N-glycans. Methods for modifying the glycosylation pathway in mammalian cells to produce antibodies with particular N-glycans has been described in, for example, International Patent Application No. WO0061739, and U.S. Published Patent Application Nos. 20040093621, 20040259150, 20030157108, 20040191256, 20040136986, and U.S. Pat. No. 6,946,292. A method for modifying the glycosylation pathway in plants has been described by Cox et al., Nature Biotechnology, doi:10.1038/nbt1260, published on-line 26 Nov. 2006. Many lower eukaryote cells also produce proteins with particular N-glycans that render the protein immunogenic when introduced into an individual. In the case of the anti-Dkk-1 antibodies, it is preferred that the glycosylation pathway of the lower eukaryote host cells be modified to produce anti-Dkk-1 antibodies without the undesirable N-glycans. Methods for modifying the glycosylation pathway in lower eukaryotes, including yeast, to produce antibodies with particular N-glycans and glycosylation patterns have been described in for example, U.S. Pat. No. 7,029, 872 and in Published U.S. Patent Application Nos. 20060034829, 20060024304, 20060034828, 20060034830, 20060029604, and 20060024292.

The transformed host cell, when cultured under appropriate conditions, synthesizes an anti-Dkk-1 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (for example, Hep G2), and a number of other cell lines. In certain embodiments, the best cell line for expressing a particular DNA construct may be selected by testing various cell lines to determine which ones have the highest levels of expression levels and produce antibodies with constitutive Dkk-1 binding properties.

In particular embodiments, it is preferable that the antibodies be produced in a lower eukaryote cell genetically engineered to produce glycoproteins having humanlike N-glycan structures. U.S. Pat. No. 7,029,872 and in Published U.S. Patent Application Nos. 20060034829, 20060024304, 20060034828, 20060034830, 20060029604, and 20060024292 disclose producing antibodies in lower eukaryote cells such as yeast and filamentous fungi that have predominantly particular N-glycan structures. Genetically engineered lower eukaryotes that can be used to produce the antibodies include those selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysospo-* rium *lucknowense*, *Fusarium* sp., *Fusarium gramineum*, *Fusarium venenatum* and *Neurospora crassa*.

Anti-Dkk-1 Antibody Compositions

Further provided are compositions comprising an effective amount of the anti-Dkk-1 antibodies or immunologically functional fragments thereof together with one or more of the following: a pharmaceutically acceptable diluent, a carrier, a solubilizer, an emulsifier, a preservative, and/or an adjuvant. Thus, the use of the antibodies and immunologically active fragments that are provided herein in the preparation of a pharmaceutical composition or medicament is also included. Such compositions can be used in the treatment of a variety of bone disorders such as osteoporosis. Acceptable formulation components for pharmaceutical preparations are nontoxic to recipients at the dosages and concentrations employed.

In addition to the anti-Dkk-1 antibodies and immunologically functional fragments that are provided, the compositions may also contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates, or other organic acids); bulking agents (such as mannitol or glycine); chelating agents (such as ethylenediamine tetraacetic acid (EDTA)); complexing agents (such as caffeine, polyvinylpyrrolidone, beta-t cyclodextrin or hydroxypropyl-beta-cyclodextrin); fillers; monosaccharides; disaccharides; and other carbohydrates (such as glucose, mannose or dextrans); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol; sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants.

The primary vehicle or carrier in a pharmaceutical composition may be either aqueous or non aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising anti-Dkk-1 antibodies or immunologically functional fragments thereof may be prepared for storage by mixing the selected composition having the desired degree of purity with optional formulation agents in the form of a lyophilized cake or an aqueous solution. Further, the anti-Dkk-1 antibodies or immunologically functional fragments thereof may be formulated as a lyophilizate using appropriate excipients such as sucrose. The formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5 to 8.5, or acetate buffer of about pH 4.0 to 5.5, which may further include sorbitol or a suitable substitute therefor.

The effective amount of a pharmaceutical composition comprising anti-Dkk-1 antibodies or immunologically functional fragments thereof will depend, for example, upon the therapeutic context and objectives. One skilled in the art will appreciate that the appropriate dosage levels for treatment, according to certain embodiments, will thus vary depending, in part, upon the molecule delivered, the indication for which the anti-Dkk-1 antibody is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg to up to about 100 mg/kg or more, depending on the factors mentioned above. In certain embodiments, the dosage may range from: 0.1 µg/kg up to about 150 mg/kg; or 1 µg/kg up to about 100 mg/kg, or 5 µg/kg up to about 50 mg/kg. In general, it is currently expected that the anti-Dkk-1 antibodies or immunological fragments thereof will be formulated as a sterile, clear liquid at a concentration of at least 10 mg/mL in isotonic buffered saline (20 mM histidine, 150 mM sodium chloride, 0.05% polysorbate 80, pH 6.4). A typical antibody formulation is filled as a single dose, 0.6 mL glass vials filled with 3.3 mL of solution per vial and each vial is stopped with a West Fluortec Teflon-coated stopper and sealed with an aluminum cap.

Although IV administration of antibody therapy for osteoporosis indications is considered acceptable; the optimal profile for the antibodies herein is subcutaneous or intraperitoneal dosing, once biweekly or monthly.

The anti-Dkk-1 antibodies or fragments have therapeutic use in stimulating osteoblast activity and increasing bone mineral density or bone mass. These antibodies and fragments are thus useful for treating patients suffering from various medical disorders that involve excessive bone loss or patients who require the formation of new bone even where there may not necessarily be excessive osteoclast activity. Blocking Dkk-1 activity results in heightened osteoblast activation via signaling transmitted by Wnt proteins. Excessive osteoclast activity is associated with numerous osteogenic disorders that can be treated with the anti-Dkk-1 antibodies and immunologically functional fragments that are provided, including ostopenia, osteoporosis, periodontitis, Paget's disease, bone loss due to immobilization, lytic bone metastases and arthritis, including rheumatoid arthritis, psoriatic-arthritis, ankylosing spondylitis and other conditions that involve bone erosion.

Various other low bone mass conditions can also be treated including a variety of forms of osteoporosis, including but not limited to, glucocorticoid induced osteoporosis, osteoporosis induced after transplantation, osteoporosis associated with chemotherapy, immobilization induced osteoporosis, osteoporosis due to mechanical unloading, and osteoporosis associated with anticonvulsant use. Additional bone diseases that can be treated with some of the antibodies or fragments include bone disease associated with renal failure and nutritional, gastrointestinal and/or hepatic associated bone diseases.

Different forms of arthritis can also be treated, examples including osteoarthritis and rheumatoid arthritis. The antibodies and fragments can also be used to treat systemic bone loss associated with arthritis (for example, rheumatoid arthritis). In treating arthritis, patients may benefit by perilesional or intralesional injections of the subject antibodies or fragments thereof. For example, the antibody or fragment thereof can be injected adjacent to or directly into an inflamed joint, thus stimulating repair of damaged bone at the site.

Some cancers are known to increase osteoclast activity and induce bone resorption, such as breast and prostate cancer. Multiple myeloma, which arises in bone marrow, also is associated with bone loss, in part likely due to the increased expression of Dkk-1 by plasma cells, which then suppresses the bone building activity of osteoblasts in the vicinity. Reducing Dkk-1 activity by administering the subject antibodies or immunologically functional fragments thereof can result in an increase in osteoblast activity that serves to counteract the excessive osteoclast activity, thereby reducing the severity of the aforementioned disorders, reducing bone erosion and inducing new bone formation in the patient.

Treatment with certain of the anti-Dkk-l-specific antibodies or immunologically functional fragments can induce a significant increase in bone mineral density in a patient suffering from an osteopenic disorder. Inhibiting Dkk-1 with the antibodies or immunologically functional fragments described herein can also be used in various bone repair applications. For example, certain antibodies and fragments can be useful in retarding wear debris osteolysis associated with artificial joints, accelerating the repair of bone fractures, and enhancing the incorporation of bone grafts into the surrounding living bone into which they have been engrafted.

Anti-Dkk-1 antibodies or immunologically functional fragments thereof can be administered alone or in combination with other therapeutic agents, for example, in combination with cancer therapy agents, with agents that inhibit osteoclast activity or with other agents that enhance osteoblast activity. For example, the inventive antibodies can be administered to cancer patients undergoing radiation therapy or chemotherapy.

Anti-Dkk-1 antibodies and immunologically functional fragments thereof may be used alone for the treatment of the above referenced conditions resulting in loss of bone mass or in combination with a therapeutically effective amount of a bone growth promoting (anabolic) agent or a bone anti-resorptive agent including but not limited to: bone morphogenic factors designated BMP-1 to BMP-12; transforming growth factor-$\beta$ and TGF-$\beta$ family members; fibroblast growth factors FGF-1 to FGF-10; interleukin-1 inhibitors, INF$\alpha$ inhibitors; RANK ligand inhibitors, parathyroid hormone (PTH), E series prostaglandins, bisphosphonates, and bone-enhancing minerals such as fluoride and: calcium. Anabolic agents that can be used in combination with the inventive antibodies and functional fragments thereof include parathyroid hormone and insulin-like growth factor (IGF), wherein the latter agent is preferably complexed with an IGF binding protein.

In addition, the anti-Dkk-1 antibodies can be administered to patients in combination with antibodies that bind to tumor cells and induce a cytotoxic and/or cytostatic effect on tumor growth. Examples of such antibodies include those that bind to cell surface proteins Her2, CDC20, CDC33, mucin-like glycoprotein I and epidermal growth factor receptor (EGFR) present on tumor cells and induce a cytostatic and/or cytotoxic effect on tumor cells displaying these proteins. Also, combination therapy can include as cancer therapy agents polypeptides that selectively induce apoptosis in tumor cells, such as the TNF-related polypeptide TRAIL.

The anti-Dkk-1 antibodies or immunologically functional fragments thereof can be administered concurrently with other treatments and therapeutic agents being administered for the same condition. Anti-Dkk-1 antibodies or immunologically functional fragments thereof can be administered prophylactically to prevent or mitigate the onset of loss of bone mass by early stage cancer (stages I or II), or can be given to ameliorate an existing condition of loss of bone mass due to metastasis to the bone. Anti-Dkk-1 antibodies of the invention may be used to prevent and/or treat the growth of tumor cells in bone. Cancer that metastasizes to bone can spread readily as tumor cells stimulate osteoclasts to resorb the internal bone matrix. Treatment with an anti-Dkk-1 antibody or immunologically functional fragment thereof will help maintain bone mineral density at the site of such metastases by stimulating increased osteoblast activity. Any cancer that has potential to metastasize to bone may be prevented or treated with an anti-Dkk-1 antibody administered before or after metastasis has occurred.

It is expected that the antibodies herein will be effective as monotherapy. However, it is also expected that the antibodies herein could be administered with existing treatments for osteoporosis, such as (but not limited to) alendronate, risedronate, ibandronate, zoledronic acid, calcitonin, estrogen(s), PTH, and conjugated estrogens, raloxifene and other selective estrogen receptor modulators, teriparatide, vitamin D and its metabolites, among others. In addition to these approved treatments, it is also expected that the antibodies herein may provide synergistic/additive benefit for any of several approaches currently in development for the treatment of osteoporosis, which include without limitation, cathepsin K inhibitors, ATP6 inhibitors, chloride channel-7 inhibitors, denosumab, or other anti-RANK antibodies or inhibitors, osteoprotegerin-Fc, $\alpha v \beta 3$ integrin antagonists, and calcilytics, among others.

Dkk-1 has also been implicated in the pathogenesis of myeloma bone disease through the suppression of osteoblast differentiation. Tian et al. (N. Engl. J. Med. 349: 2483-2494 (2003) found overexpression of the Dkk-1 gene and Dkk-1 protein in multiple myeloma (MM) patients with focal bone lesions. In vitro, recombinant human Dkk-1 or bone marrow plasma with high Dkk-1 levels inhibited osteoblast function. This effect was neutralized by treatment with a polyclonal anti-Dkk-1 antibody. It was also suggested that the reduction of Dkk-1 levels after treatment (autologous stem cell transfer) may be correlated with the normalization of osteoblast function, which could provide a basis for developing agents that block Dkk-1 activity such as the antibodies disclosed herein, thus restoring osteoblast function and counteracting the increased osteoclastogenesis observed in myeloma (See, Politou et al. In J Cancer 119:1728 (2006)).

Mice engrafted with primary multiple myeloma cells expressing varying levels of Dkk-1 when treated with control or Dkk-1 neutralizing antibodies for four to six weeks show reduced BMD in controls but increased BMD from pre-treatment levels ($p<0.001$) in the anti-Dkk1 antibody group. The bone anabolic effect of anti-DKK1 antibodies was associated with reduced multiple myeloma burden ($p<0.04$). The authors concluded that Dkk-1 is a key player in multiple myeloma bone disease and that blocking Dkk-1 activity in myelomatous bones reduces osteolytic bone resorption, increases bone formation, and helps control multiple myeloma growth (See, Yaccoby et al., Blood. Oct. 26, 2006; [Epub ahead of print]). In addition, PC-3 prostate cancer cells express the Wnt inhibitor Dkk-1. Decreasing Dkk-1 levels enabled the PC-3 cells to induce osteoblastic activity, including alkaline phosphatase production and mineralization, in murine bone marrow stromal cells indicating that Dkk-1 blocked Wnt-mediated osteoblastic activity in PC-3 cells (Hall et al., Cancer Res 65:7554 (2005)). Together, the above results suggest the involvement of Wnt-signaling and Dkk-1 in cancer cells known to invade bone environment. Therefore, the Dkk-1 antibodies and immunologically functional fragments thereof disclosed herein may provide a therapeutic treatment for alleviating the bone-destructive effects of cancer cells (for example, multiple myeloma, breast cancer, prostate cancer, and the like) invading the bone micro-environment.

The following examples are intended to promote a further understanding of the present invention.

EXAMPLE 1

The human anti-Dkk-1 antibodies were prepared using the Cambridge Antibody Technology (CAT) human single chain Fv phage display library (Cambridgeshire, United Kingdom). The library was panned against both Rhesus monkey and mouse Dkk-1 (RhDkk-1 and MsDkk-1, respectively). Each library was subjected to three rounds of solution-based panning against biotin labeled Dkk-1 (100 nM). Though the percentage of sequence identity and similarity is high between mouse and rhesus Dkk-1, six different panning strategies were employed to ensure library selections would cross react to Dkk-1 from both species (Table 4). It is from scheme (E) that all subsequent data originates.

TABLE 4

CAT scFV Phage Display Library Selections vs. Dkk-1

| Scheme | Round1 | Round 2 | Round 3 |
|---|---|---|---|
| A | MsDkk-1 | MsDkk-1 | MsDkk-1 |
| B | MsDkk-1 | RhDkk-1 | MsDkk-1 |
| C | MsDkk-1 | MsDkk-1 | RhDkk-1 |
| D | RhDkk-1 | RhDkk-1 | RhDkk-1 |
| E | RhDkk-1 | RhDkk-1 | MsDkk-1 |
| F | RhDkk-1 | MsDkk-1 | RhDkk-1 |

To validate the antigen specificity of the selected scFv-phage clones, 176 phage clones from each library in round 2 and 88 clones from each third round library were tested in a time-resolved fluorescence (TRF) ELISA assay using HEK293 cells overexpressing LRP5 or LRP6 and rhesus or mouse Dkk-1 protein labeled with fluorescent Europium-chelate (Eu). Eu-Dkk-1 protein binding to human embryonic kidney, HEK293 cells overexpressing human LRP5 or LRP6 was monitored by measuring the time-resolved fluorescence of bound ligand. When Dkk-1 protein bound to LRP5 (or 6)-expressing cells, a strong signal was detected. When the Dkk-1 was tested in the presence of an anti-Dkk-1 antibody, a reduction in fluorescent signal indicated interference with the Dkk-1/LRP5 (or 6) interaction. 264 Dkk-1 scFVs were tested in this primary assay for the ability to inhibit binding of Dkk-1 protein to the cell surface. Based on the above assay, 20 scFVs among the group identified to inhibit binding of Dkk-1 to the cell surface (Table 5) were chosen for conversion to fully human IgGs.

TABLE 5

Diverse sequence anti-Dkk-1 inhibitory antibody clones.

| SEQ ID | Library | Phage ELISA (+) Rhesus | Phage ELISA (+) Mouse | % inhibition of Dkk-1 | Comments |
|---|---|---|---|---|---|
| RH1-10 | BMV | X | X | 89% | Sequence represented 17x |
| RH1-12 | BMV | X | X | 63% | |
| RH1-25 | BMV | X | X | 66% | |
| RH1-26 | BMV | X | X | 64% | |
| RH1-28 | BMV | X | X | 80% | Sequence represented 4x |
| RH1-30 | BMV | X | X | 74% | |
| RH1-60 | BMV | X | X | 66% | |
| RH1-96 | BMV | X | X | 63% | |
| RH2-18 | CS | X | X | 74% | |
| RH2-31 | CS | X | X | 89% | Sequence represented 4x |
| RH2-54 | CS | X | X | 67% | |
| RH2-59 | CS | X | X | 61% | Sequence represented 4x |
| RH2-80 | CS | X | X | 62% | |
| RH3-9 | DP47 | X | X | 61% | |
| RH3-15 | DP47 | X | X | 77% | Sequence represented 5x |
| RH3-29 | DP47 | X | X | 66% | Sequence represented 5x |
| RH3-54 | DP47 | X | X | 62% | |
| RH3-76 | DP47 | X | X | 67% | |
| RH3-84 | DP47 | X | X | 66% | |
| RH3-94 | DP47 | X | X | 68% | |

DNA encoding the heavy chain variable regions were fused in-frame with DNA encoding the IgG2M4 constant region whereas DNA encoding the light chain variable regions were fused in-frame with DNA encoding either lambda or kappa light chain constant region in alignment with the corresponding variable regions. The resulting antibody expression vectors are shown in the plasmid maps (FIGS. 1A and 1B) by using the expression vector encoding antibody RH2-18 as an example. The cloning procedure is described below. The light chain lambda vector that was used was built in-house and comprises cloning sites flanked by a human CMV (HCMV) promoter and leader sequence on the 5' end of one cloning site and the light chain lambda sequences and bovine growth hormone (BGH) pA polyadenylation signal on the 3' side of the other cloning site. The heavy chain IgG2M4 constant region vector that was used was built in-house and comprises cloning sites flanked by an HCMV promoter and leader sequence on the 5' end of one cloning site and heavy chain IgG2M4 sequences and BGH pA polyadenylation signal on the 3' side of the other cloning site. The expression vectors carry oriP from Epstein Barr virus (EBV) viral genome for prolonged expression in 293EBNA cells and the bacterial sequences for kanamycin selection marker and replication origin in E. coli. The leader sequence at the amino termini of the antibodies mediated the secretion of the expressed antibodies into the culture medium. The leader sequence for heavy chain is MEWSWVFLFFLSVTTGVHS (SEQ ID NO:29) and light chain: MSVPTQVLGLLLLWLTDARC (SEQ ID NO:30)The rest of the 19 scFv leads were converted to IgG in the same manner.

Figure 1B:
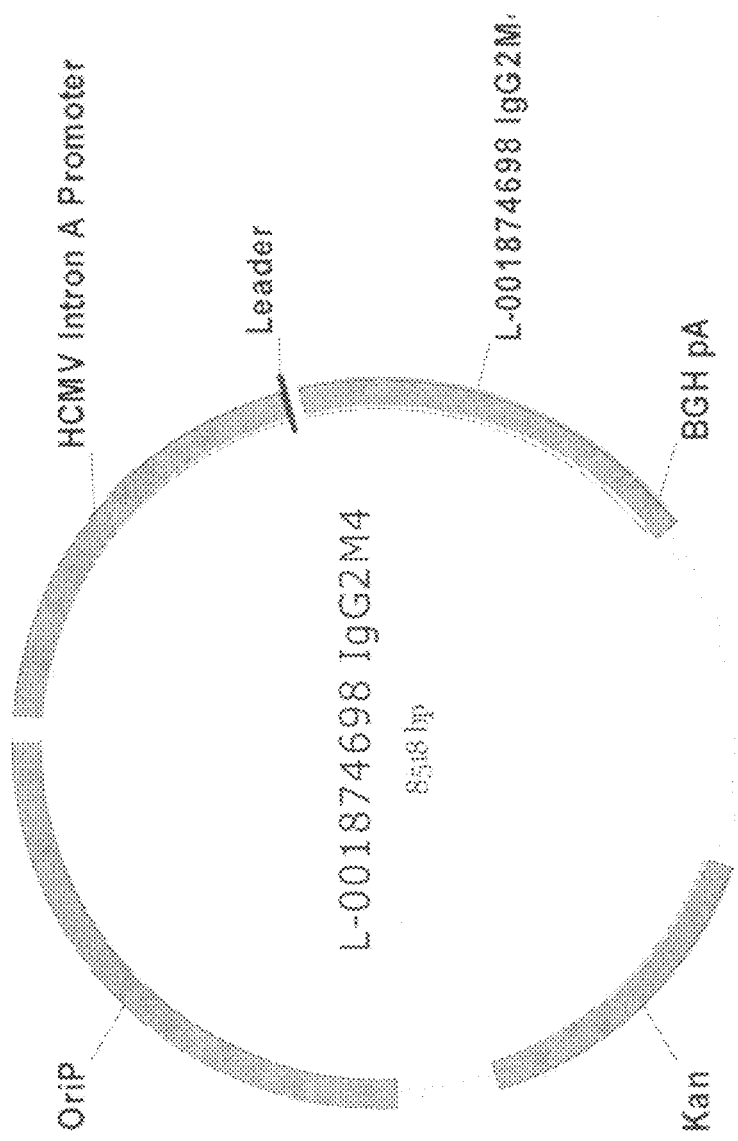
FIG. 1B shows a diagram of the plasmid encoding the RH2-18 heavy chain. OriP is the Epstein Barr virus origin of replication for expression in eukaryote cells. HCMV intron A promoter is the human cytomegalovirus promoter and first intron. IgG2M4 encodes the heavy chain IgG2M4 constant region. Leader encodes a leader or signal sequence for secretion of the light chain polypeptide into the culture medium. BGH pA is the bovine growth hormone polyadenylation signal sequence. Kan is the kanamycin gene for selection of the vector in E. coli.

To make the vectors shown in FIGS. 1A and 1B, the respective variable regions were PCR amplified in a volume of 25 μL containing high fidelity PCR master mix, template volume 1 μL and forward and reverse primers: 1 μL each. PCR conditions were one cycle of 94° C. for two minutes, 25 cycles of 94° C. for 1.5 minutes, 60° C. for 1.5 minutes and 72° C. for 1.5 minutes with a final extension at 72° C. for 7 minutes. The following PCR primers were used heavy chain forward, 5'-ACAGG TGTCC ACTCG GAGGT GCAGC TGGTG CAGTC T-3' (SEQ ID NO:31); heavy chain reverse 5'-GC-CCT TGGTG GATGC ACTCG AGACG GTGAC CAGGG T-3' (SEQ ID NO:32) and light chain forward 5'-ACAGA TGCCA GATGC CAGTC TGTGT TGACG CAGCC G-3' (SEQ ID NO:33); light chain reverse 5'-GTTGG CCTTG GGCTG ACTTA AAACG GTGAG CTGGG T-3' (SEQ ID NO:34). The amplified light and heavy chain variable region PCR products were cloned in-frame with the appropriate leader sequence at the 5'-end and constant region at the 3'-end using In-Fusion strategy (Clontech, Palo Alto, Calif.) and cloned into E. coli XL10 cells from Stratagene, La Jolla, Calif.). The DNA sequences for the clones were confirmed by sequencing and the amino acid sequences were deduced from the DNA sequences. The amino acid sequences for RH2-18 light and heavy chains (without the leader sequences) are shown in FIG. 1C. The variable regions are italicized. FIGS. 1D and 1E show the CDR regions for the RH2-18 light chain and heavy chain variable regions and also identify the sequence differences in the frameworks between the RH2-18 light chain and heavy chain variable regions and the corresponding regions in the germline.

Figure 1F:
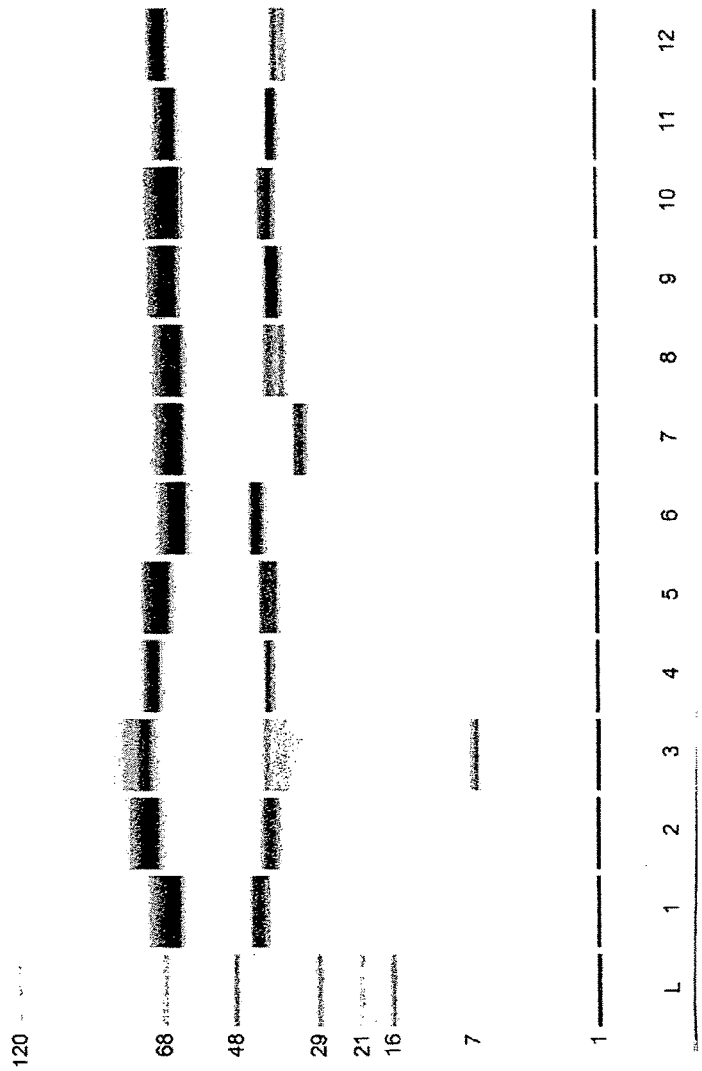
FIG. 1F shows the results of a LABCHIP 90 capillary electrophoresis of 12 converted anti-Dkk-1 antibodies purified for in vitro analysis. Lane 2 is the RH2-18 anti-Dkk-1 antibody.

The above plasmids were transfected into 293EBNA monolayer cells using FUGENE transfection reagents (FUGENE is a trademark of Fugent LLC and is available-from Roche Diagnostics, Nutley, N.J.). The transfected cells were incubated in OPTI-MEM serum free medium (Invitrogen) and the secreted antibodies were purified from the culture medium using protein A/G affinity chromatography. The concentration of purified antibodies was determined by OD at 280 nm and the purity by LABCHIP capillary SDS gel electrophoresis (Caliper Life Sciences, Hopkinton, Mass.). FIG. 1F shows the results of a LABCHIP electrophoresis analysis for 12 converted antibodies. Lane 2 shows the RH2-18 antibody. The antibodies purified were used for in vitro characterization as described herein. The above plasmids were also used for mass production of RH2-18 antibody and the other antibodies for in vivo animal studies described in the animal study section.

For all biological assays, rhesus Dkk-1 protein was prepared by Baculovirus expression and purified via metal-affinity resin. Isolated anti-Dkk-1 antibodies from CAT-library panning were selected on the basis of ability to bind to rhesus (and mouse) Dkk-1 proteins. To determine if an antibody inhibited Dkk-1-interactions with cell surface receptors (LRP5/6) and inhibited of Dkk-1-function, the following assays were established: a cell-based Dkk-1-binding assay, a Dkk-1 functional assay measuring canonical Wnt-signaling, and a cell differentiation assay for Dkk-1-functional analysis using the osteoblastic differentiation marker alkaline phosphatase (ALP). The above assays were run in consecutive order to select neutralizing antibodies for (a) blocking Dkk-1 binding to LRP5/6, (b) inhibiting Dkk-1-function in Wnt signaling, and (c) neutralizing the negative Dkk-l-function on bone cell differentiation in vitro.

EXAMPLE 2

A time-resolved fluorescence (TRF) cell-based assay was used to show that four of the anti-Dkk-1 antibodies inhibited Dkk-1 binding to LRP5/6.

Figure 2A:
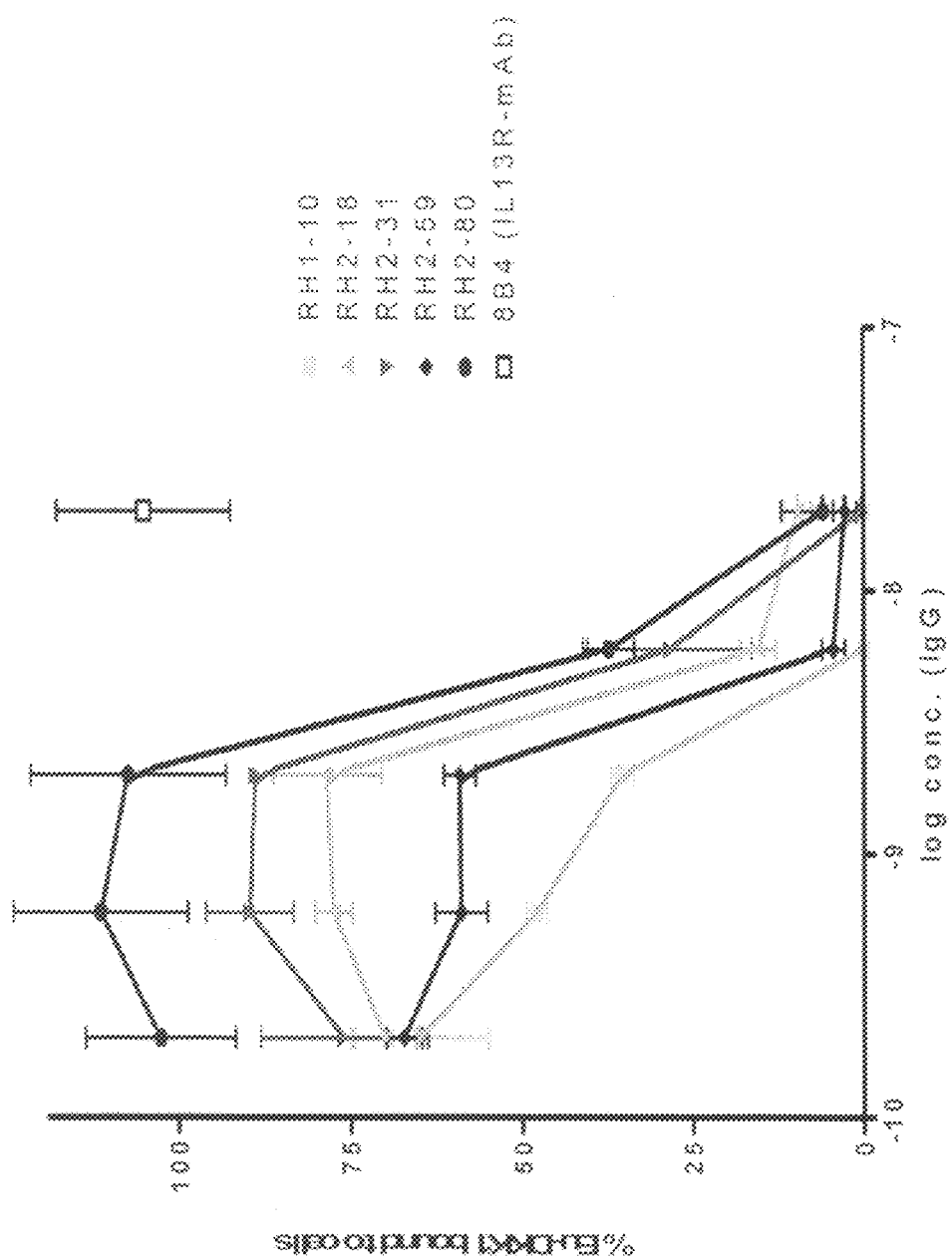
FIG. 2A shows Eu-Dkk-1 binding to HEK293hLrp5 cells and inhibitory activity of anti-Dkk-1 antibodies RH2-10, RH2-18, RH2-31, RH2-59, and RH2-80 at various concentrations. 8B4 is a control antibody that is non-specific for Dkk-1.
Figure 2B:
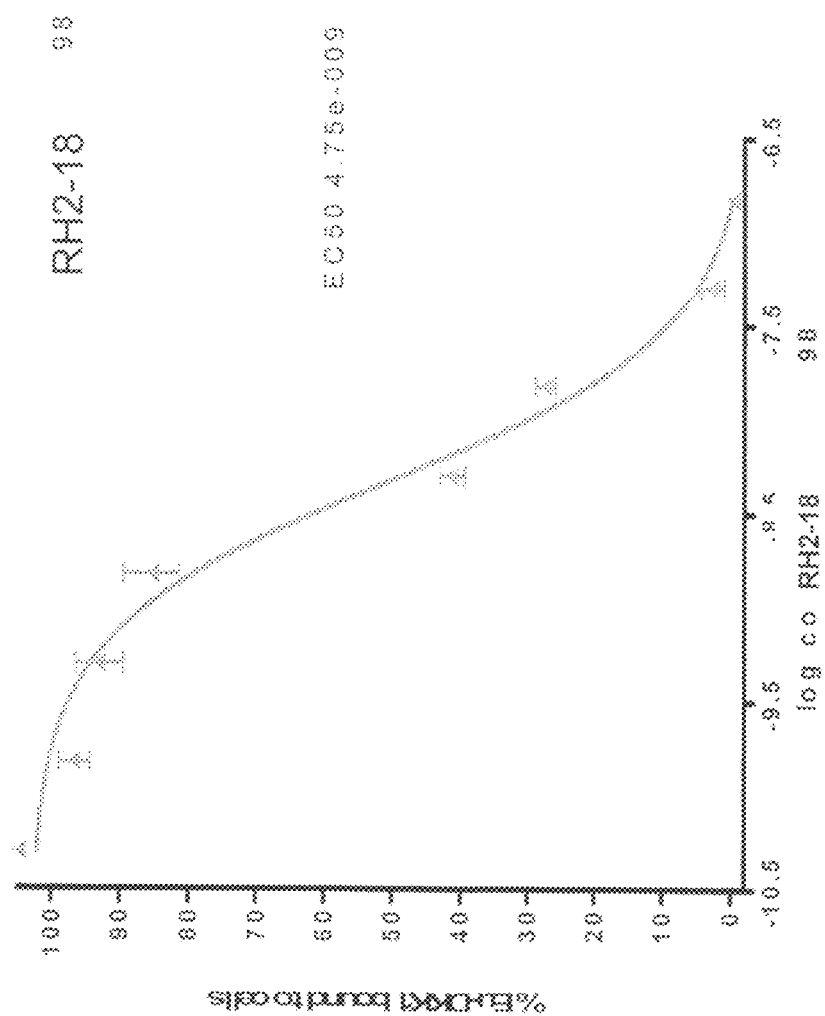
FIG. 2B shows the result for RH2-18 antibodies retitrated using an extended dose range. The results show that for this assay format the RH2-18 antibodies had an effective dose of about 5 nM.

For the assay, the anti-Dkk-1 antibodies were added to HEK cells overexpressing LRP5 (HEK293hLrp5 cells) at final concentrations of 0.2, 0.6, 2.0, 6.0, and 20 nM. Anti-IL3 Receptor monoclonal antibody (8B4) was used as a negative control. Eu-labeled Dkk-1 (100 pM) was incubated with the cells in absence or presence of the antibodies for 20 minutes. Dkk-1 bound in solution by the antibodies and thus blocked from binding to the cell surface of the HEK293hLrp5 cells was removed by 4× wash steps and Eu-labeled Dkk-1 bound to cell surface was measured by TRF signal. Eu-labeled Dkk-1 protein binding to HEK293 cells overexpressing human LRP5 or LRP6 was monitored by measuring the time-resolved fluorescence of bound ligand. The results for the top five of these antibodies (RH1-10, RH2-18, RH2-31, RH2-59, and RH2-80) are shown in FIG. 2A and 2B. FIG. 2A shows Eu-Dkk-1 binding to HEK293hLrp5 cells and the ability of the above five antibodies to inhibit binding of the Dkk-1 to LRP5. FIG. 2A shows a titration of RH2-18 antibody inhibition of Dkk-1 binding to LRP5 over an extended dose range. FIG. 2B shows that in this assay format, an effective dose of RH2-18 was about 5 nM. The data in FIGS. 2A and 2B shows that the inhibitory activity of the anti-Dkk-1 antibodies was substantial to complete in the low nanomolar range (4.75 nM for RH2-18 antibody). Additional analyses, using Eu-labeled recombinant mouse Dkk-1 provided similar results, indicating that the inhibitory mechanism of the selected anti-Dkk-1 antibodies was conserved for both the mouse and rhesus Dkk-1 protein.

EXAMPLE 3

This example shows the neutralizing activity of the anti-Dkk-1 antibodies on Dkk-1 function in Wnt signaling. Dkk-1 is a negative regulator of the canonical Wnt-signaling through β-catenin and nuclear Lef-1/TCF.

Figure 3:
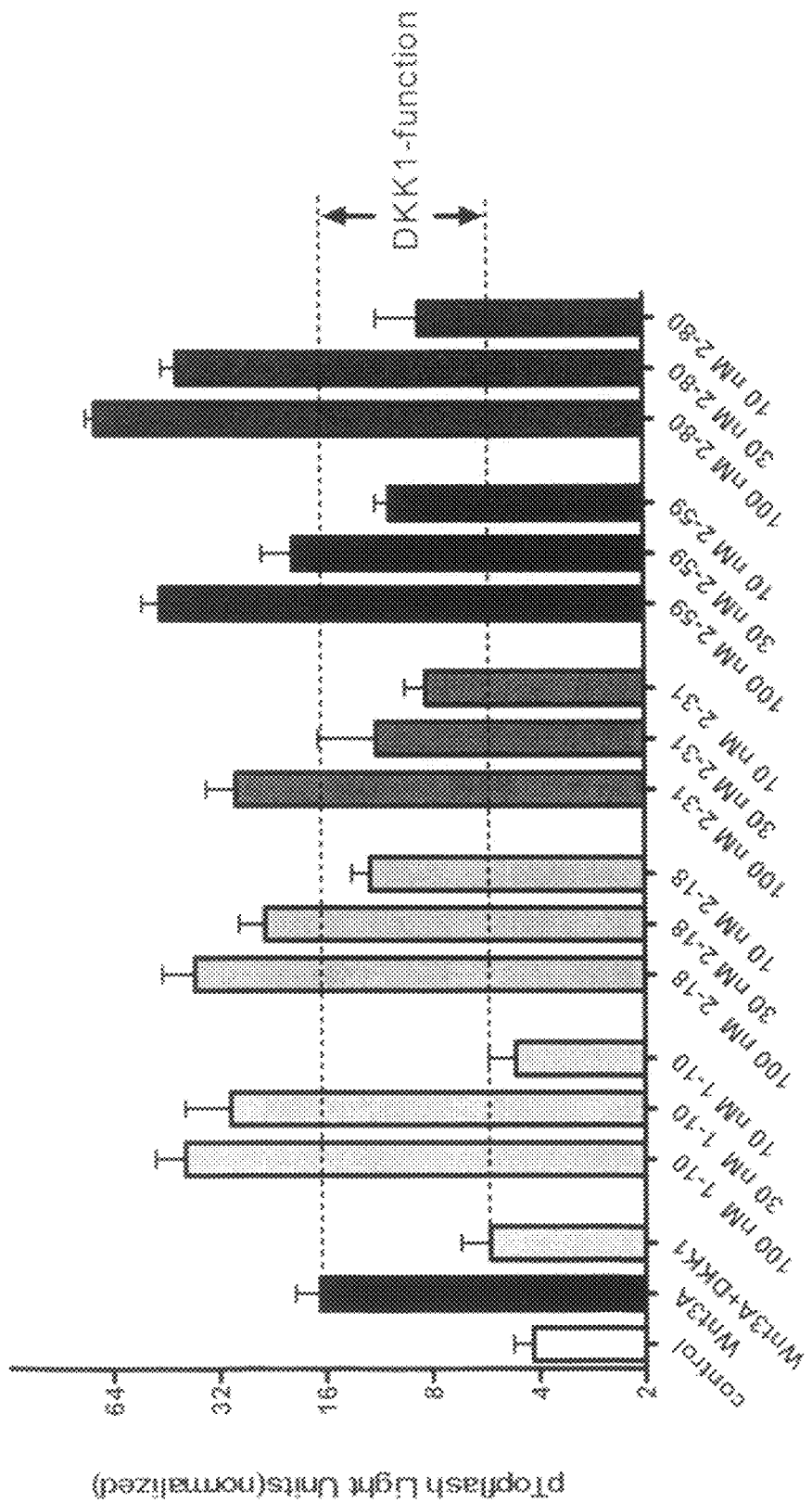
FIG. 3 shows the neutralizing activities of anti-Dkk-1 antibodies RH1-10, RH2-18, RH2-31, RH2-59, and RH2-80 antibodies on Dkk-1 function in Wnt3A induced signaling. Treatment with Wnt3A significantly stimulated the signaling pathway (black bar) compared to control treatment (open bar). Anti-Dkk-1 antibodies were added at indicated concentrations.

HEK293hLrp5 cells were co-transfected with a reporter plasmid with Lef-1/TCF binding sites (pTOPflash) and an expression vector encoding Lef-1. Cells transfected with pTOPflash/Lef-1 are highly responsive to Wnt-ligands as indicated by increased activity of the reporter (luciferase). Rhesus monkey Dkk-1 (50 nM) robustly inhibits pTopflash activity in this cell system. The anti-Dkk-1 antibodies RH1-10, RH2-18, RH2-31, and RH2-80 were tested here for their ability to also neutralize Dkk-1-function over a 20 hour time period. The anti-Dkk-1 antibodies were added at 10, 30, and 100 nM concentrations. The results shown in FIG. 3 indicate that all of the tested anti-Dkk-1 antibodies blocked Dkk-1 binding to the LRP5 on the cell surface and thereby inhibited the functional activity of Dkk-1 in the Wnt3A signaling pathway. As shown in FIG. 3, treatment with Wnt3A significantly stimulated the signaling pathway compared to the control and that Rhesus monkey Dkk-1 inhibited Wnt3A activation of the reporter readout. The antibodies neutralized the Dkk-1 effect at 30 nM and higher concentrations. Note that with all anti-Dkk-1 antibodies tested, signals could rise to greater than with Wnt3A ligand alone. This effect required addition of recombinant Dkk-1 protein to the assay system, as in a parallel assay this antibody effect on Wnt-signaling was not observed in the absence of exogenously added rhesus-Dkk-1 protein.

EXAMPLE 4

The effect of the neutralizing Dkk-1 antibodies on osteoblastic cell differentiation in vitro was tested. The mesenchymal pluripotent cell line, C3H10T1/2, differentiates towards the osteoblastic cell lineage by treatment with osteogenic factors. Wnt3A treatment over three days induces the expression of the early osteoblastic marker alkaline phosphatase (ALP). Dkk-1 inhibits Wnt3A induced differentiation as determined by measuring endogenous ALP activities. This osteoblastic cell differentiation system provides a relevant cell context and a more prolonged 3-day assay period.

Figure 4:
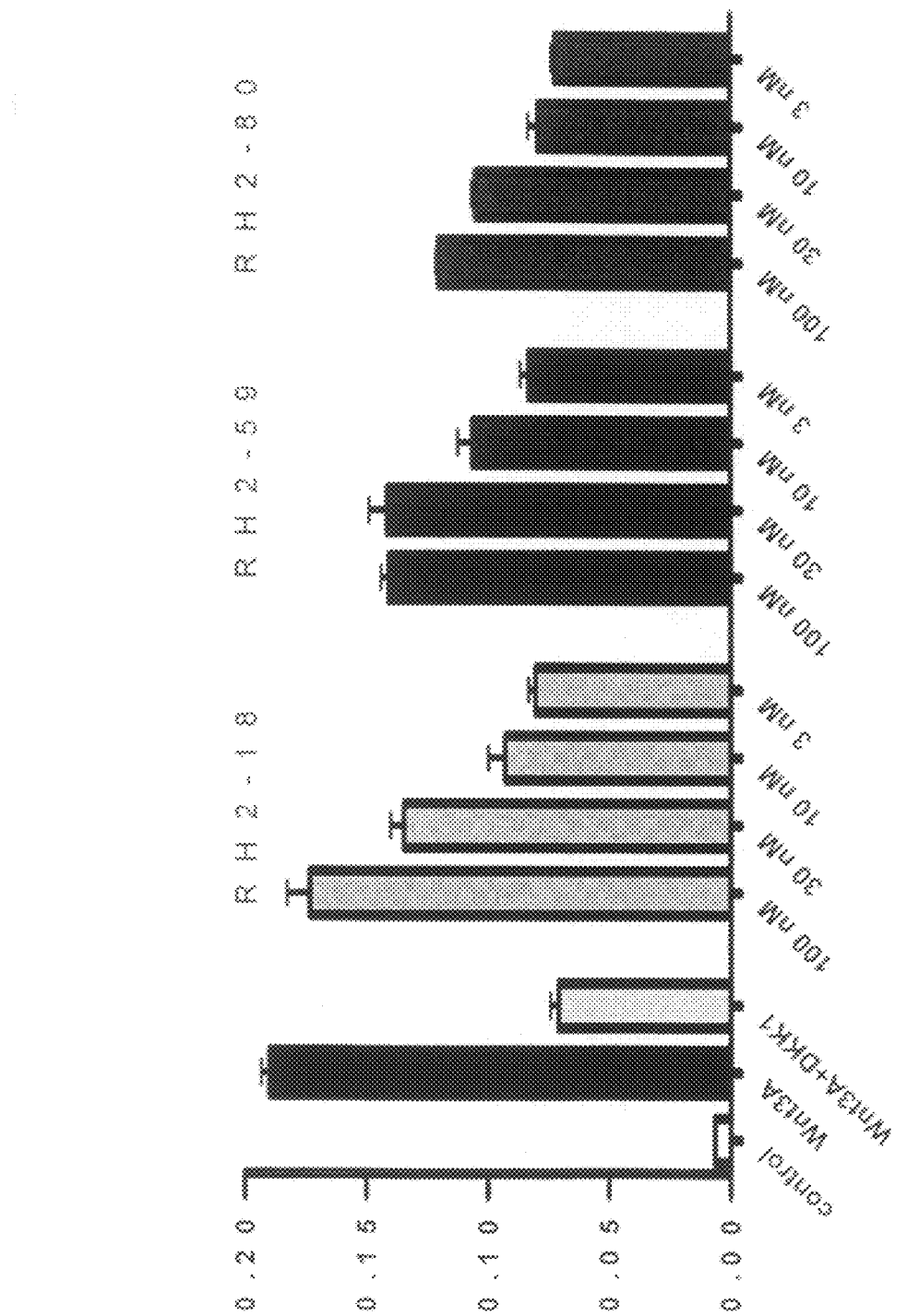
FIG. 4 shows the effect of the RH2-18, Rh2-59, and Rh2-80 antibodies on osteoblastic cell differentiation. Differentiation of C3H10T1/2 cells towards the osteoblastic phenotype was determined by increased endogenous ALP activities.

Osteoblastic cell differentiation of C3H10T1/2 cells was determined by measuring the increase in endogenous ALP activities. Cells were grown to confluence in culture and treated with Wnt3A for 3 days to induce osteoblastic differentiation. Concomitant treatment with recombinant Dkk-1 inhibited Wnt3A induced ALP activity. As shown in FIG. 4, when anti-Dkk-1 antibodies RH2-18, RH2-59, or RH2-80 were added at 10 nM, 30 nM or 100 nM final concentrations, the inhibitory function of Dkk-1 on osteoblastic cell differentiation was neutralized in a dose-dependent manner. The neutralizing effect of 100 nM RH2-18 on Dkk-1 was nearly complete and its stability sufficient to produce and maintain a neutralizing effect within a 3-day assay period. RH2-31 was found to have little potency/stability and was therefore excluded from further studies (data not shown). Related analyses of endogenous marker genes (TROY, IGFBP2, Axin2) induced within the first 24 hours of treatment showed a similar capacity for these antibodies to block Dkk-1 inhibition of Wnt3a-induced gene expression in this cell background.

EXAMPLE 5

An epitope map of the RH2-18 antibody was constructed. Dkk-1 protein is composed of two cysteine-rich domains located in the N-terminal and C-terminal regions, respectively. We generated deletion constructs for Dkk-1 encoding either the N-terminal or C-terminal region of rhesus-Dkk-1 and confirmed that cysteine-rich-domain-2 located in the C-terminal half of Dkk-1 is necessary and sufficient for Dkk-1 binding to the receptor LRP5/6.

The neutralizing anti-Dkk-1 antibodies disclosed herein cannot detect denatured Dkk-1 protein on Western-immunoblots. Further, they do not bind to discrete peptides derived from the Dkk-1 C-terminus. This suggested that the epitope on Dkk-1 that is recognized by the anti-Dkk-1 antibodies herein is complex (that is, topographical based and not peptide-based).

Figure 5A:
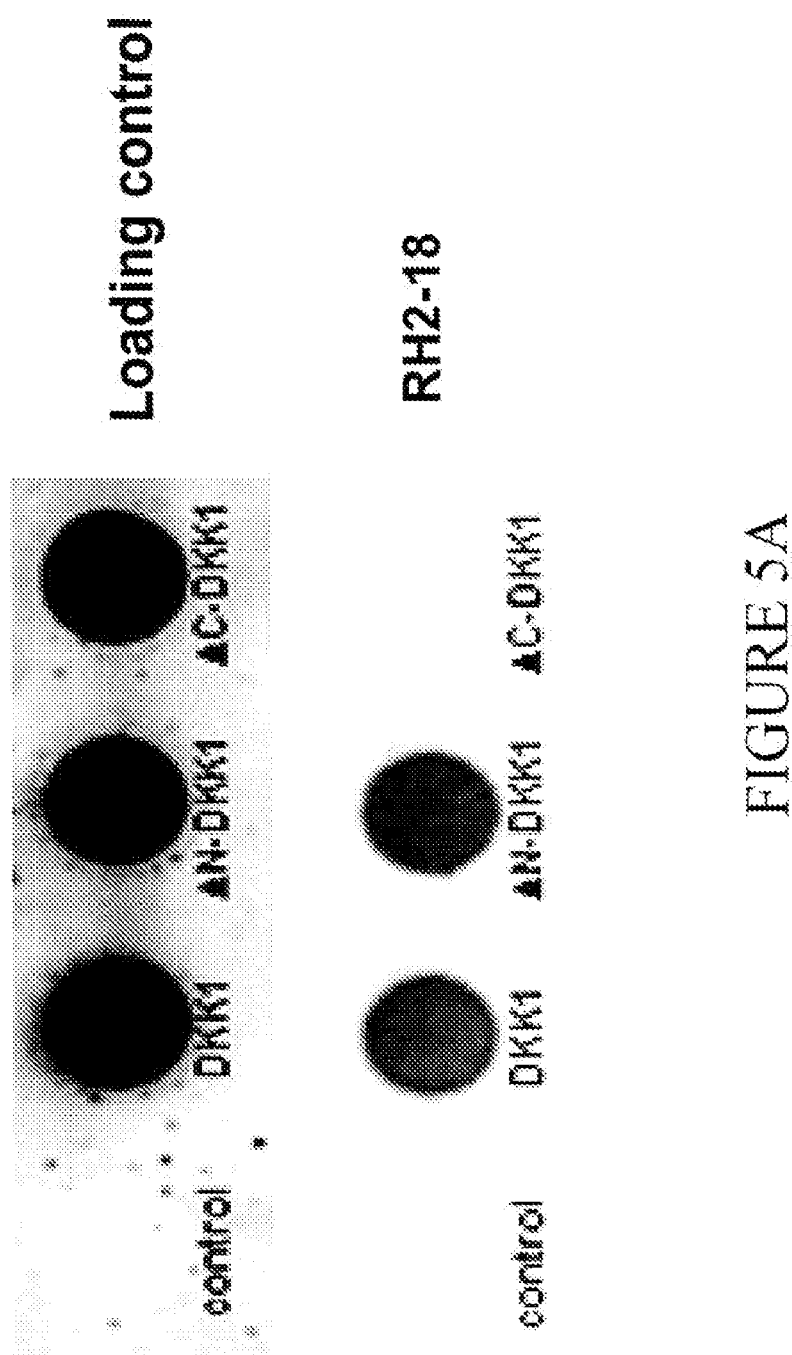
FIG. 5A shows a dot-blot binding analysis using antibody RH2-18 showing its specificity for the C-terminal region of Dkk-1. Rhesus monkey Dkk-1 proteins were fused to a green fluorescent protein (GFP) tag (loading control). Full-length rhesus Dkk-1 protein, C-terminal region (ΔN-Dkk-1, encoding residues 159 to 266) or N-terminal region (ΔC-Dkk-1, encoding residues 1-158) were expressed and analyzed by dot-immunoblotting using RH2-18 antibody.

FIG. 5A shows a dot-blot binding analysis of RH2-18. Rhesus Dkk-1 proteins were fused to a GFP tag (loading control). Full-length rhesus Dkk-1 protein, C-terminal region (ΔN-Dkk-1, encoding amino acid residues 159 to 266) or N-terminal region (ΔC-Dkk-1) were expressed and analyzed by dot-immunoblotting using RH2-18 antibody. Briefly, DKK1-GFP tagged variants were expressed in transiently transfected 293 cells and native conditioned media was blotted directly onto nitcocellulose membranes. Bound native protein was probed with tag-antibody (anti-GFP, Abcam Inc., Cambridge, Mass.) or anti-DKK1 antibody RH2-18. Bound antibodies were detected with secondary antibodies coupled to alkaline phosphatase.

The dot blot analyses showed the binding of neutralizing antibodies RH2-18 (as well as RH1-10, RH2-31, RH2-59, RH2-80) to the C-terminal region of Dkk-1 (amino acids 159- to 266). This indicated that the antibody epitope(s) maps primarily to within cysteine-rich-domain-2 of Dkk-1. Moreover, the dot blot analysis showed that the antibody binds to native protein (whereas the Western blots demonstrated no binding to denatured protein). The C-terminal domain of Dkk-1 is predicted to form a globular tertiary structure by homology model with colipase (as described below). Together these data indicate that the epitope of the ant-Dkk-1 antibodies herein and RH2-18 antibody in particular is defined by a complex epitope affected by both sequence and tertiary structure of Dkk-1 in its cysteine-rich-domain-2.

Figure 5B:
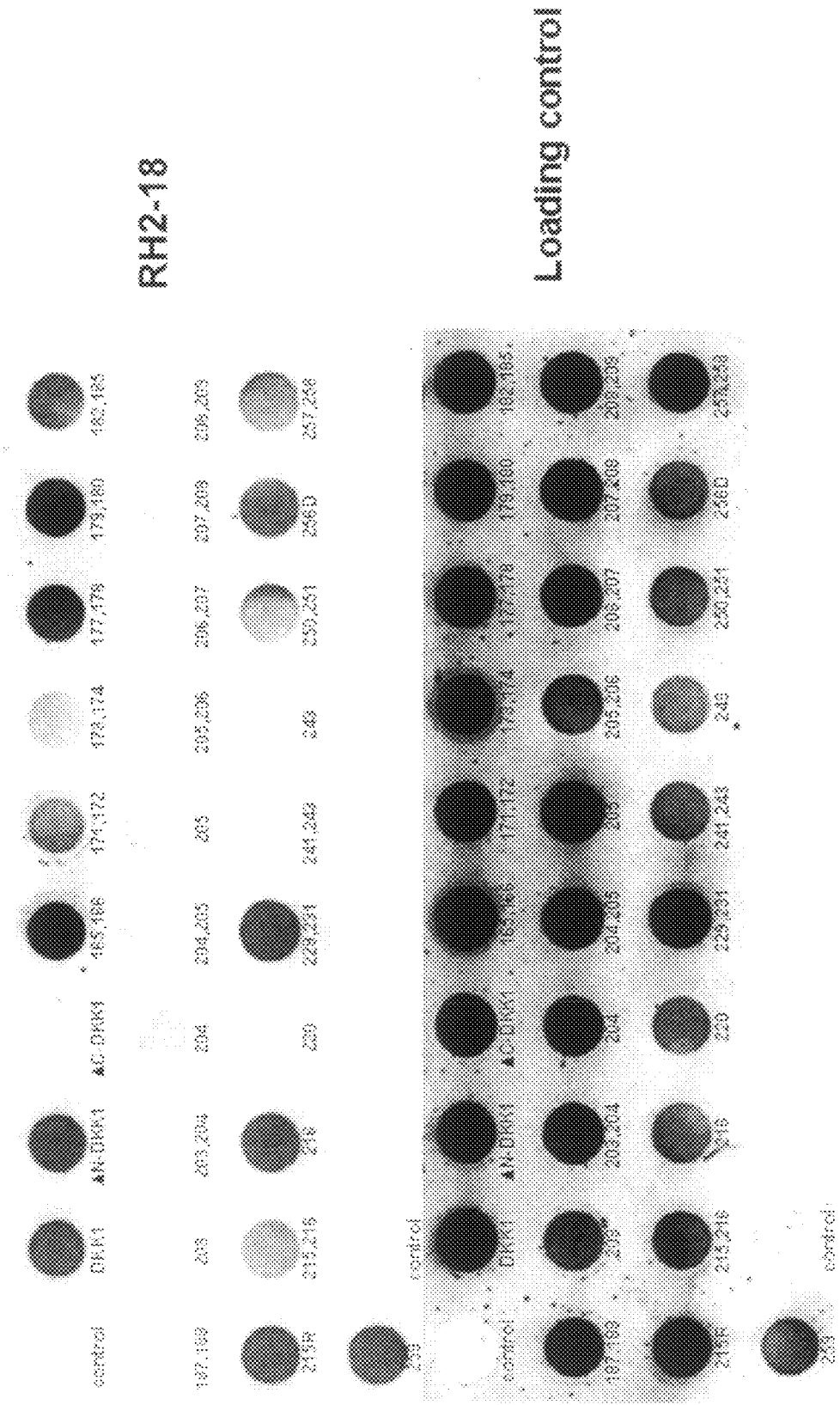
FIG. 5B shows a dot-blot binding analysis that shows that RH2-18 antibody binding is lost when various amino acid substitutions are made in the Dkk-1 C-terminal domain. Rhesus Dkk-1 proteins were fused to a GFP tag (loading control). Full-length rhesus Dkk-1 protein, C-terminal region (ΔN-Dkk-1, encoding residues 159 to 266) or N-terminal region (ΔC-Dkk-1) were expressed and analyzed by dot-immunoblotting using RH2-18 antibody. Alanine-substitutions were introduced in ΔN-Dkk-1 and the position numbers of the amino acid-residues substituted are indicated.
Figure 5C:
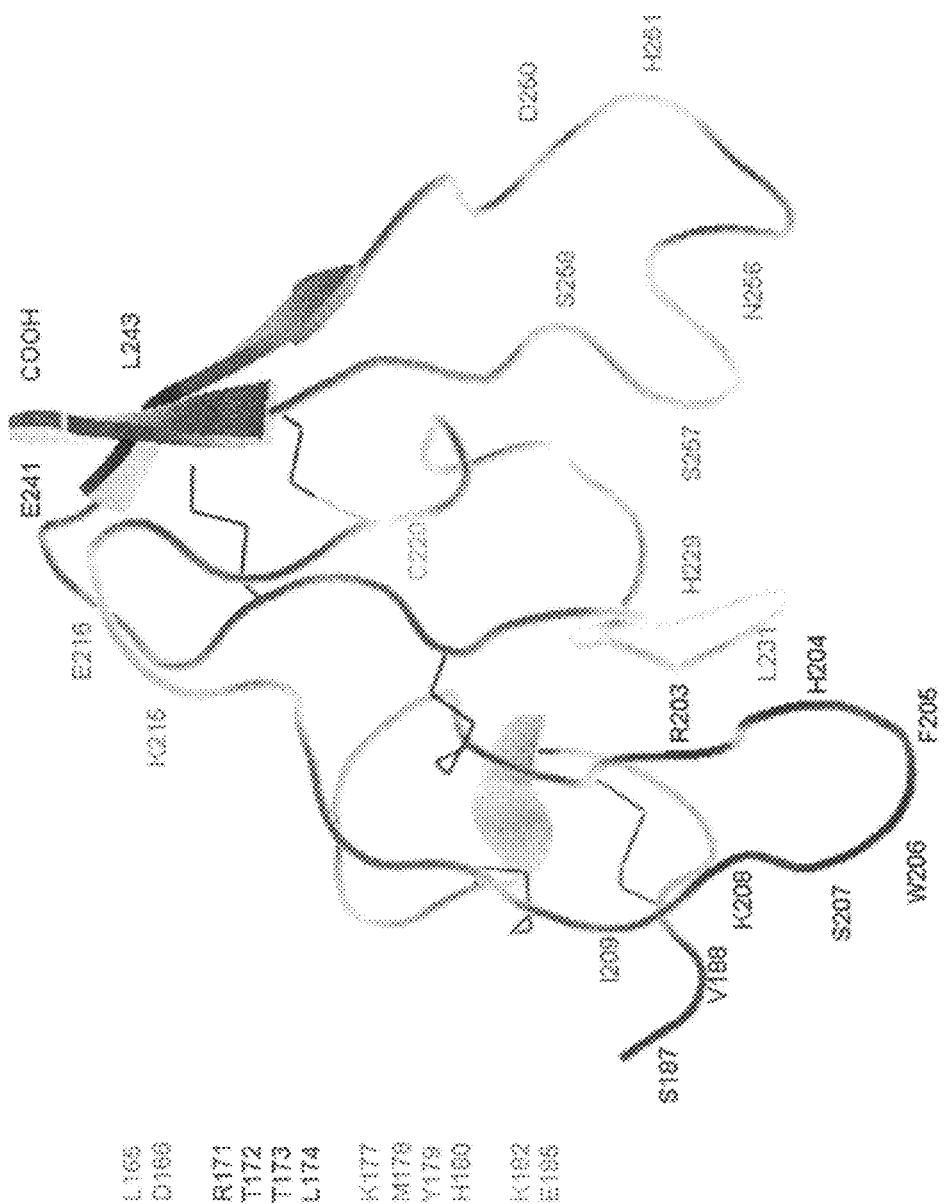
FIG. 5C shows a structural-homology model of Dkk-1 C-terminal domain (amino acids 187 to 266) showing the amino acid residues necessary for binding of RH2-18 antibody. Amino acid-numbers given have been substituted by Alanine-scanning. Substitutions of amino acid matched normal controls (about 5 SD above the mean in clinical populations). The responsible mutations (e.g., $G_{171}V$) have been tested in transgenic mice leading to increased bone mass and bone formation rates. Canonical Wnt signaling is blocked in the presence of the inhibitory protein Dickkopf-1 (Dkk1), which is highly expressed in bone. Dkk-1 is a 266 amino acid protein with a 26 kDa molecular mass. The protein has two cysteine rich domains— amino acids 97 to 138 and 183 to 245, a motif that is highly conserved among species. Dkk-1 shares a high percentage of sequence identity/similarity between species (human: rhesus 97/99, human: mouse 80/87 and rhesus: mouse 79/87). Interestingly, Dkk-1 loses its ability to inhibit hypermorphic $G_{171}$ mutants of LRP5, a key signaling defect of the mutated receptor. Further, heterozygous knockout mice lacking Dkk-1 similarly show an increase in bone mass (as do $G_{171}$V-LRP5 mice), which is accompanied by a four-fold rise on bone formation rates. The composite data surrounding LRP5 and its inhibition by Dkk-1 suggest that an osteoanabolic response could be generated through selective activation of the receptor or by interfering therapies that prevent Dkk-1 inhibition of LRP5 signaling in the bone microenvironment. Indeed, as shown in the Examples, the neutralizing anti-Dkk-1 antibodies disclosed herein (at 0.5 to 5.0 mg/kg, s.c. twice weekly) increased bone mass in growing mice with PTH-like effects on the distal and whole femur. Other anti-Dkk-1 antibodies have also been shown to increase bone mass in growing mice, for example, see for example, U.S. Published Application No. 20060127393.

Additional analyses of the C-terminal domain using site-directed mutagenesis (alanine-scanning method) identified amino acid residues $S_{187}$ to $V_{188}$, $R_{203}$ through $K_{208}$, and $E_{241}$ through $L_{243}$ as the Dkk-1 amino acid-residues most important for RH2-18 antibody binding to Dkk-1. In this regard, mutations to these residues caused a striking reduction in the capacity of the antibody to bind to the mutant Dkk-1 in the dot blot analyses (See FIG. 5B). FIG. 5B shows a loss of RH2-18 binding by various amino acid substitutions in the Dkk-1 C-terminal domain as determined by dot-blot binding analyses. Rhesus Dkk-1 proteins were fused to a GFP tag (loading control). Full-length rhesus Dkk-1 protein, C-terminal region (ΔN-Dkk-1, encoding amino acid residues 159 to 266) or N-terminal region (ΔC-Dkk-1, encoding residues 1 to 158) were expressed and analyzed by dot-immunoblotting using RH2-18. Alanine-substitutions were introduced in ΔN-Dkk-1 and the amino acid-residues affected are indicated. From independent structure/function analysis of Dkk-1 by alanine-scanning, amino acid residues $R_{203}$, $H_{204}$ ($F_{205}$) within the C-terminal domain were identified as necessary for Dkk-1 binding to LRP6 (See Identification of DKK1 Residues Necessary for Interaction with LRP5/6. Lipfert et al., J. Bone Miner. Res. 21: S99 (2006)). Thus, these residues are important for both Dkk-1 function (binding to LRP5/6) and for binding the RH2-18 antibody. The overlap between the key amino acid residues required for Dkk1 interaction with LRP5 and the amino acid residues for Dkk1 binding to RH2-18 antibody provide a rationale for the inhibitory activity of the RH2-18 antibody.

Interpretation of the effects of the mutations shown in FIG. 5B is best considered in the context of a three-dimensional model of the second cysteine-rich domain (See FIG. 5C). FIG. 5C shows a structural-homology model of Dkk-1 C-terminal domain (amino acid residues 187 to 266) indicating the amino acid residues necessary for binding of Dkk-1 to the RH2-18 antibody as determined by alanine-scanning (See FIG. 5C). Substitutions of amino acid residues found to result in diminished antigen-antibody interaction in immunoblotting experiments using non-denatured protein are amino acid residues $S_{187}$ to $V_{188}$, $R_{203}$ through $K_{208}$, $E_{241}$, and $L_{243}$), which appear to play a role in the formation of a complex epitope. Amino acid residues $R_{171}$ to $L_{174}$, which are outside the amino acid sequence shown in the C-terminal homology model, were also found to contribute to the complex epitope. In addition, substituting amino acid $C_{220}$ with alanine also resulted in a loss of RH2-18 binding to Dkk-1.

Thus, the RH2-18 antibody binds a complex epitope comprising amino acid residues from different discrete regions of the second cysteine-rich domain were identified as being necessary for antibody binding: amino acid residues $S_{187}$ and $V_{188}$, both in a region preceding the first finger domain, and amino acids $R_{203}$, $H_{204}$, $F_{205}$, $W_{206}$, $S_{207}$, and $K_{208}$, all of which comprise the first finger of the domain. Further towards the C-terminus of the domain, and preceding the second finger, are $E_{241}$ and $L_{243}$, which were also required for RH2-18 binding to Dkk-1. Finally, $Cys_{220}$ is necessary for RH2-18 binding to Dkk-1. $Cys_{220}$ is predicted to play an important role in establishing a proper tertiary structure, RH2-18 to bind the Dkk-1, again an indication of the complex nature of this epitope. Together, the data suggest that RH2-18 epitope is defined by a topographical surface of Dkk-1 C-terminal region that includes but is not limited to the first finger domain $A_{202}$-$I_{209}$ of Dkk-1.

A comparison of the amino acid sequences of human Dkk-1, -2, -4, and Rhesus monkey Dkk-1 (FIG. 6A) shows a lack of conservation of amino acid residues located within Dkk-1 that were identified as important for RH2-18 binding to Dkk-1 as described above. Amino acid residues in Dkk-1 that were deemed to be necessary for RH2-18 binding are enclosed within the blue boxes. Note the lack of sequence conservation between Dkk-1 and Dkk-2 and Dkk-4 for amino acid residues: $Arg_{171}$-$Leu_{174}$, $Ser_{187}$ to $Val_{188}$, $Ser_{207}$ and $Glu_{241}$. Based on the epitope mapping of residues in Dkk-1 that are necessary for binding of RH2-18 and based on the lack of sequence conservation between Dkk-1 and Dkk-2 and Dkk-4 at amino acid residues $Arg_{171}$ to $Leu_{174}$, $Ser_{187}$, $Val_{188}$, $Ser_{207}$, and $Glu_{241}$, RH2-18 and other antibodies sharing a similar epitope are predicted to show a high degree of selectivity for Dkk-1.

Figure 6A:
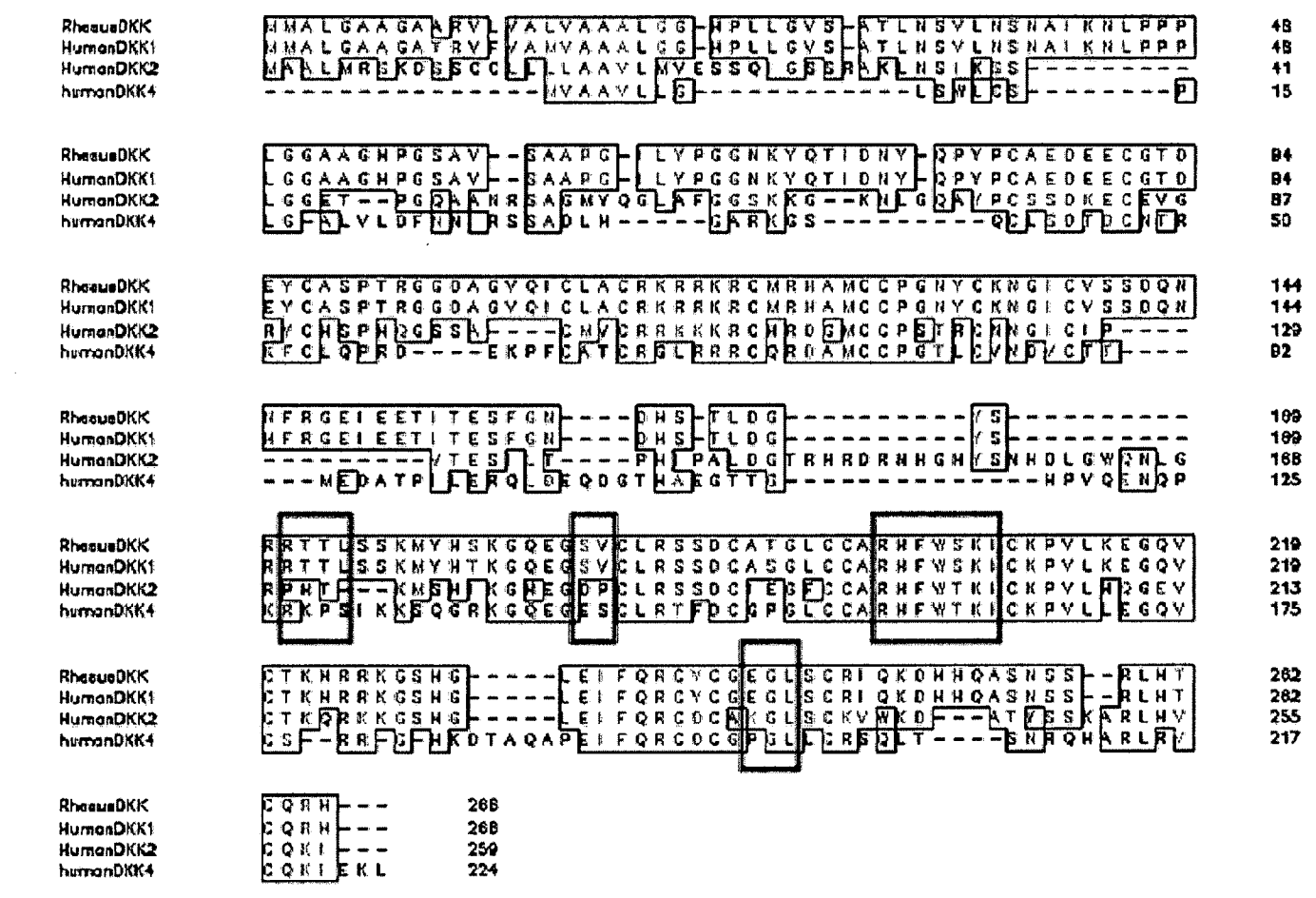
Figure 6B:
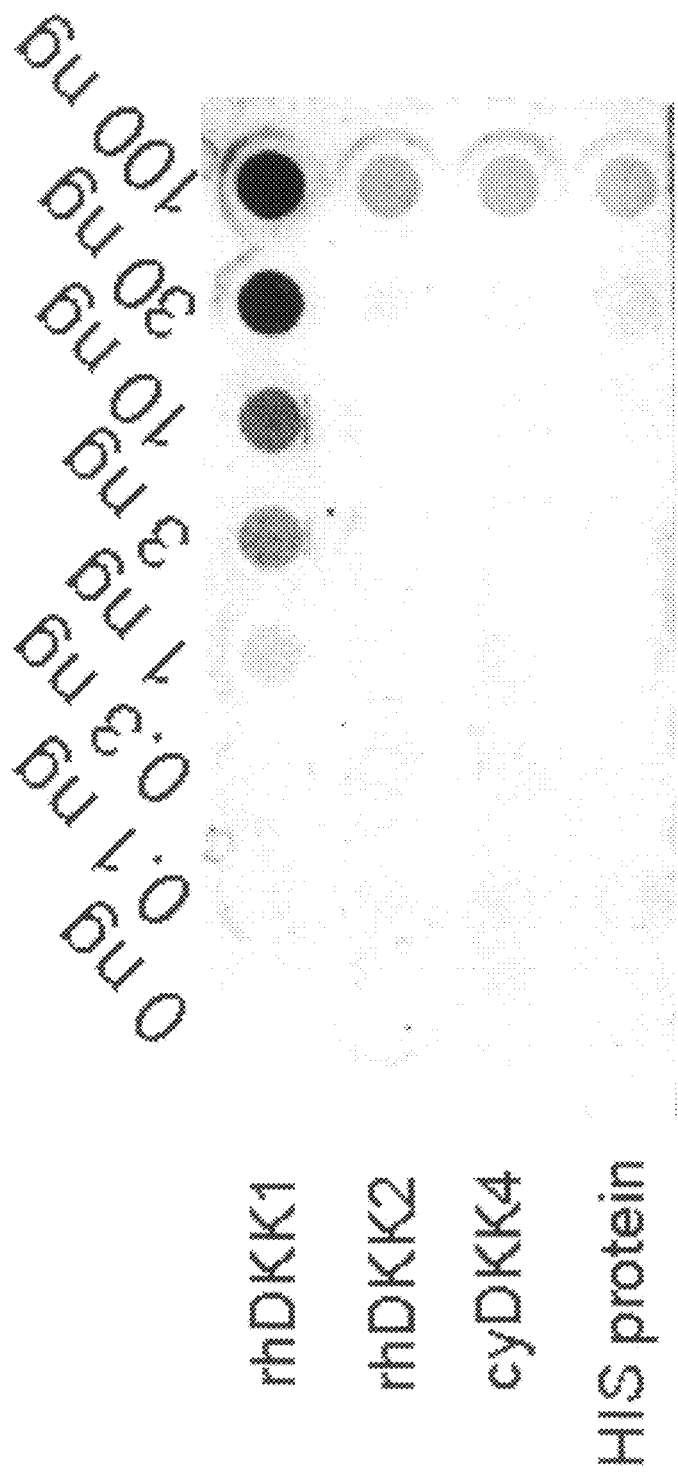

The Dkk-1 amino acid sequence is closely related to that of Dkk-2 and Dkk-4 with 50% and 45% identity at the amino acid-level, respectively. Cross-reactivity of RH2-18 against rhesus monkey Dkk-2 (using a chimeric protein consisting of the N-terminal region of the rhesus Dkk-1 fused to the C-terminal region of the rhesus Dkk-2 with myc and His-6 tags at the C-terminal end of the Dkk-2 C-terminal region; see SEQ ID NO:71) and cynomolgus monkey Dkk-4 (SEQ ID NO:70) was tested by dot-blot analysis using recombinant proteins. Native recombinant rhesus monkey Dkk-1, Dkk-2, and cynomolgus monkey Dkk-4 proteins (0.1 ng to 100 ng) were used. A non-related recombinant protein was loaded as a control for non-specific assay signal (HIS protein). The dot blots were probed with RH2-18. FIG. 6B shows that there was little or no detectable specific binding of RH2-18 to Dkk-2 or Dkk-4. Selectivity of the antibody towards Dkk-1 was minimally 100-fold. In this assay format, the detection limit for binding of RH2-18 to rhesus Dkk-1 was found to be about 1 ng. Signal strength at all concentrations of these Dkk isoforms was comparable to that towards a non-related HIS-tagged protein. Consistent with the epitope mapping and the sequence alignment data, the results showing that there was little to no cross-reactivity of the antibody to these proteins suggest there would be a low probability that RH2-18 would bind to Dkk-2 or Dkk-4. These data indicate RH2-18 and similar antibodies recognize a novel, complex, three dimensional epitope covering several discrete regions of Dkk-1, which indicates that RH2-18 and similar antibodies are unique.

EXAMPLE 6

The affinity of the RH2-18 antibody for human Dkk-1 and Rhesus Dkk-1 was determined by measuring RH2-18 binding kinetics by surface plasmon resonance in a Biacore 3000 instrument according to manufacturer's instructions (Biacore, Inc., Piscataway, N.J.). Several independent affinity studies were performed using different RH2-18 antibody lots against human Dkk-1 and rhesus Dkk-1. The calculated Kd values for each experiment ranged from 202 to 269 pM for binding to human Dkk-1, with a mean value of 251 pM. For rhesus monkey Dkk-1, the range was between 771 to 934 pM and the mean value was 858 pM.

The quality of the RH2-18 antibodies was assessed by size exclusion chromatography in comparison to other well characterized mABs. The results suggest excellent stability of RH2-18 antibodies as there was no apparent aggregation.

EXAMPLE 7

RH2-18 was evaluated in in vivo pharmacodynamic and efficacy studies.

Genetic proof-of-concept data exists that indicates that disrupting the Dkk-1/Wnt interaction in the developing skeleton causes increased bone mass. In addition, an anti-Dkk-1 antibody developed by Amgen was osteoanabolic when injected to rats in a three week study (30 mg/kg, twice weekly s.c.) (See, DKK1 Inhibition Increases Bone Mineral Density in Rodents Grisanti M et al., J. Bone Miner. Res. 21: S25 (2006). Bone mass increases were seen in both growing and adult mice dosed in a similar fashion and for a similar period of time. An in vivo proof-of-concept study was undertaken with RH2-18 to validate the phenotype pharmacologically. This study was performed in growing mice with a plan to later test the response in the adult skeleton. Thus, the purpose of the study was to establish that RH2-18 antibodies, which neutralized all tested Dkk-1 functions in vitro, increased bone mass in the growing skeleton. The tested hypothesis, therefore, was that RH2-18 increases bone mass in a dose-effect fashion in the long bone of growing mice.

Figure 8:
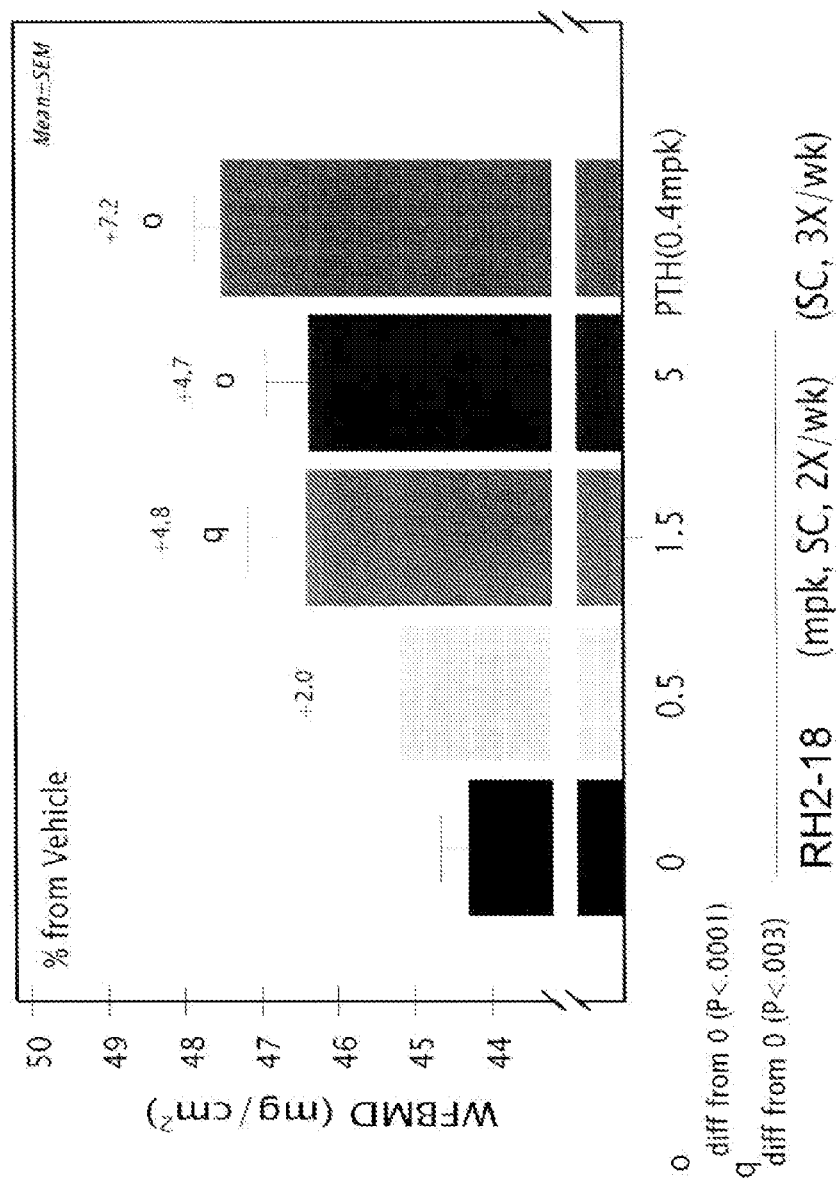
Figure 9:
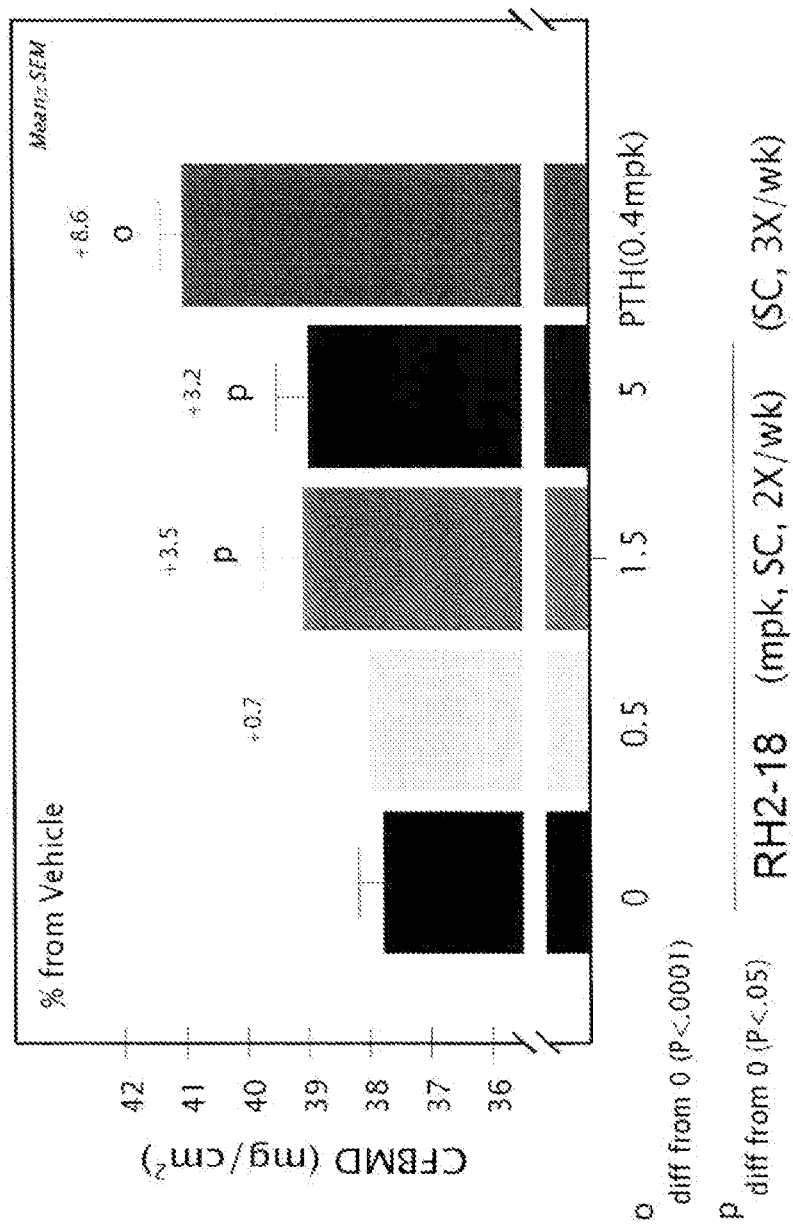

Five week old C57BL/6J female mice were obtained and acclimated to the animal facility for one week. RH2-18 antibody was administered subcutaneously (s.c.) in 0.1 mL phosphate buffer per mouse. There were 11 mice per group. Mice were treated twice weekly for four consecutive weeks with 0, 0.5, 1.5, or 5 mg/kg RH2-18 antibody, or 0.4 mg/kg PTH (1-34) (s.c., 3×/wk). At necropsy, femurs and vertebrae were dissected free and fixed in 70% ethanol. Whole femurs were scanned by Piximus (GE/Lunar; Schenectady, N.Y.) dual energy X-ray absorptiometry. The femurs were subdivided into a distal region of interest (ROI), located 0 to 3 mm from the distal end, and a central region of interest, located 5 to 10 mm from the distal end. The central ROI is composed of 100% cortical bone, while the distal ROI is about 20% trabecular bone. Piximus software calculates bone mineral density (BMD, $mg/cm^2$) for whole bone (WFBMD), distal femur (DFBMD), and central femur (CFBMD). The results are shown in FIGS. 7 through 9.

Figure 7:
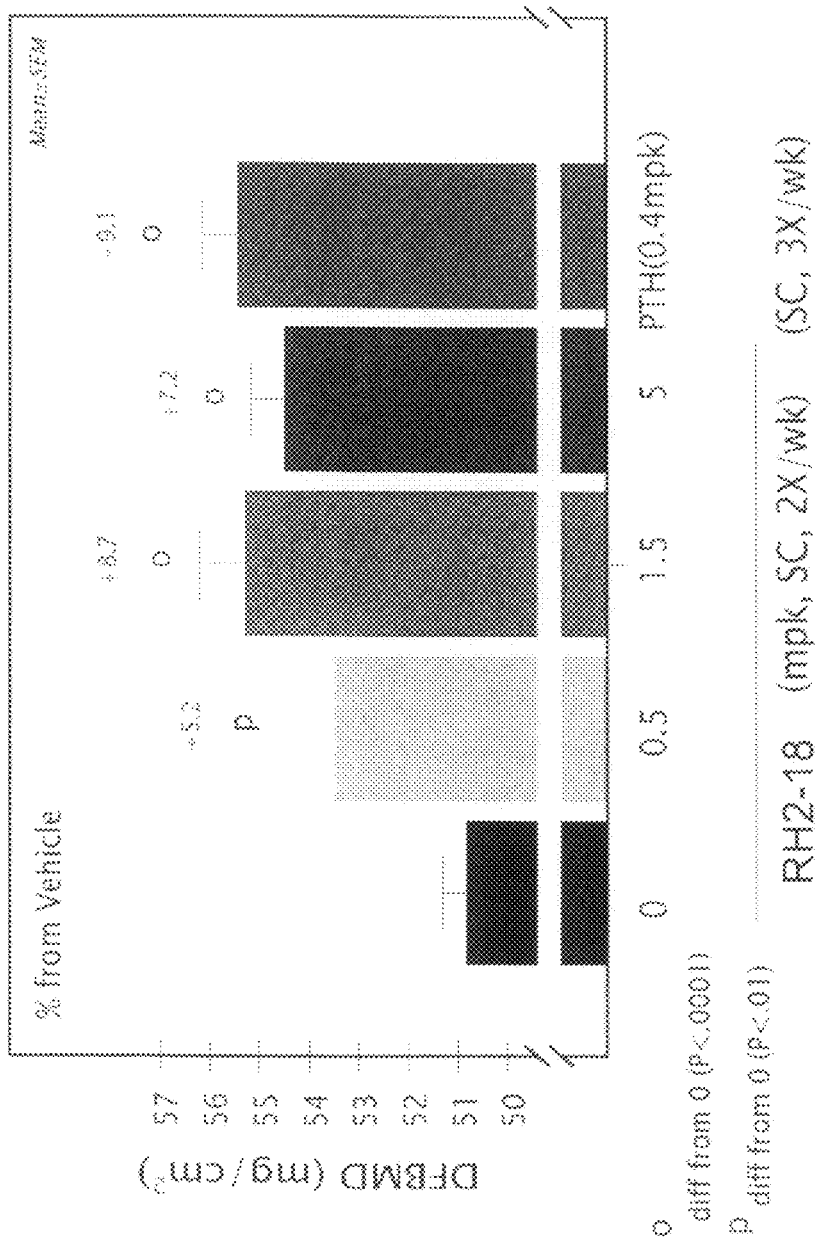

FIG. 7 shows that the distal femur bone mineral density (BMD) was increased 5.2 to 8.7% in a dose effect fashion by RH2-18 antibody, in the dose range 0.5 to 5 mg/kg, This BMD change most likely represents effects on both cancellous and cortical bone. FIG. 8 shows that whole femur BMD was increased 4.7 to 4.8% by RH2-18 antibody, in the dose range 1.5 to 5 mg/kg. This BMD change most likely represents effects on both cancellous and cortical bone. FIG. 9 shows that central femur BMD was increased 3.2 to 3.5% in a dose effect fashion by RH2-18 antibody, in the dose range 1.5 to 5 mg/kg. This BMD change represents effects primarily on cortical bone.

These results indicate that administering RH2-18 antibody to the mice over a four week period caused in a dose dependent manner a significant increase in bone mass in growing female mice.

It can be concluded from the results that administering RH2-18 antibody (which blocks the interaction of Dkk-1 and Wnt) to mice causes high bone density in growing mice. Therefore, it is possible to increase bone mass in the growing skeleton using antibodies such as RH2-18 to neutralize the Dkk-1/Wnt signaling blockade.

EXAMPLE 8

The canonical Wnt signaling cascade regulates intestinal epithelial cell proliferation. Genetic lesions in the genes for cytoplasmic signaling intermediates (β-catenin, APC, axin) cause enhanced transcriptional activity, which is associated with more that 90% of all colorectal cancer. To date, no such tumorigenic mutations have been described for cell surface receptors or secreted intermediates that regulate this pathway, including Dkk-1. Nonetheless, the possible tumorigenic effect of antibody that neutralizes Dkk-1 was evaluated.

Dkk-1 antibody should only exert effects on tissues where Dkk-1 is expressed. Thus, the tissue distribution of Dkk-1 is an important factor in determining safety. In mice, Dkk-1 is mainly expressed in bone (about 64-fold over the next highest expressing tissue) as shown in Table 6 below.

TABLE 6

CT Values for Dkk-1 Expression in Select Tissues of Mouse.

| mouse | Bone | Bladder | Intestine | Liver | Uterus |
|---|---|---|---|---|---|
| CT value | 26 | 32 | 36 | 34 | 35 |

Table 6 shows CT values for Dkk-1 expression in select tissues of mouse. For reference, CT is the threshold cycle. It is the PCR cycle in real-time quantitative PCR assays at which a statistically significant increase in reporter fluorescence can be detected above the background. CT values in the mid-upper 30s represent very low to no expression. The mRNA level is defined as low with 30<CT<40, medium 30<CT<25, high 25<CT<15. As shown above, expression of Dkk-1 was very low or not at all in bladder, intestine, liver, and uterus tissue and moderate in bone.

In human tissues, the expression levels of Dkk-1 in the same tissue were observed to vary depending on the donor. Expression was generally at minimal detection levels in normal intestine, colon or liver (CT values in the high 30s (that is, undetectable), where Wnt signaling abnormality is associated with the tumorigenesis. Dkk-1 CT values on average were in the high 20s for human bladder, cervix, stomach, and uterus (tissues not associated with Wnt/β-catenin-induced tumors), while they were around 30 for several of the bone samples we obtained from patients after knee replacement. In this regard, Dkk-1 expression was highest in tissues not typically associated with Wnt signaling-induced tumors. Conversely, tissues where cytoplasmic mutations can be associated with tumorigenesis showed no substantial Dkk-1 expression.

For human cell lines, Dkk-1 CT values were in the middle 20s for MG-63, Caco-2, MCF-7, SW480 and HCT116 cells, while they were in the 30s range in HEK-293, SW48 and DLD1 cells. The latter two cell lines are derived from colon cancer tissue with cytoplasmic Wnt signaling pathway mutations. In human tissue samples, Dkk-1 tended to be up-regulated in tumors as compared to their paired normal tissues. In these studies, Dkk-1 expression in these cells was measured and compared to that of other proliferative markers (Ki-67, PCNA, E2F1 and IGFBP-3) by real-time quantitative PCR analysis using a TAQMAN system (Applied Biosystems, Foster City, Calif.). All data CT values were converted to fold induction vs. the corresponding normal samples. In summary, Dkk-1 tissue distribution in mice Dkk-1 showed that the mRNA for this gene is mainly expressed in bone, while it is expressed in bone, bladder and cervix in humans. Dkk-1 is highly up-regulated in most human tumors or cancer cell lines, as were several known proliferative markers.

To monitor the effects of anti-Dkk-1 antibodies on proliferation of normal tissues in vivo, the levels of the proliferation markers identified above (Ki-67, PCNA, E2F1) and genes associated with cell hyperplasia (IGFBP-3, Dkk-1) in mice treated for four weeks (proof-of-concept study described in Example 7) were quantified. These markers were chosen as a measure of cell proliferation in selected tissues (intestine, liver, bladder, uterus). Quantitative PCR analysis using a TAQMAN system did not reveal any consistent or substantial difference in the expression of the proliferation markers in anti-Dkk-1 antibody-treated treated vs. control samples after four weeks of treatment.

Based on the higher expression of Dkk-1 in colon cancer cell lines, the effects of anti-Dkk-1 antibody on transcription and proliferation were assessed in vitro. RH2-80 antibody (30 μg/mL) was tested in a proliferation assay using colon cancer cell lines exhibiting constitutively active Wnt signaling—SW480, HCT116, SW48, DLD1, and HEK293. MG-63 osteosarcoma cells and non-specific antibody 8B4 were used as controls. For measuring cell proliferation, the cells were cultured according to American Type Culture Collection (ATCC) protocols. The day before performing the proliferation assay, freshly prepared cells were seeded at 2 to 5×10$^3$ cells/well of 96-well Cytostar scintillating plate in 100 μL of the corresponding cell medium. On the following day, 0.5 μCi/mL of [methyl-$^{14}$C]thymidine was added to each well along with either RH2-80 antibody, 8B4 antibody, or Wnt3A. Cell growth was measured using a 1450 MICROBETA Jet (Wallac Inc., Gaithersburg, Md.) at 1 day, 2 days, 3 days, and 5 days after adding the antibody. Greater integration of [methyl-$^{14}$C]thymidine into cells, correlated with greater light detected within the Cytostar plate on MICROBETA Jet. Cells were replenished with fresh media containing treatment on the third day. Data shown in the FIG. 10B represented day 3 treatment.

RH2-80 antibody (30 μg/mL) was tested in a TOPFlash transcription assay using colon cancer cell lines exhibiting constitutively active Wnt signaling—SW480, HCT116, SW48, DLD1, and HEK293. MG-63 osteosarcoma cells and non-specific antibody 8B4 were used as controls.

For measuring Wnt/DKK1 signaling in the assay, cells were seeded at 25,000 cells/well in 96-well plate in 100 μL of the complete cell medium according to ATCC protocol the day before transfection. On the day of transfection, 60 μL of FuGene6, 375 ng pTopflash, 80 ng pTKrenilla, and 5 μg pcDNA3.1-LEF1 were added to a final volume of 600 μL OPTIMEM. The mixture was incubated for 1 hour at room temperature. Then, 1.4 mL of OPTIMEM was added to the above mixture and mixed well gently. Then, 20 μL of the DNA mixture was added to each well of 96-well plate. The plate was gently tapped and put back to the 37° C. incubator. The day after transfection, cells were treated with the either RH2-80 antibody, 8B4 antibody, or Wnt3A. About 24 hours after treatment, a Dual-luciferase assay was performed according to Promega protocol. Luciferase signal was normalized to renilla signal first before calculating the induction. Fold induction was obtained by comparing to control signal.

Figure 10A:
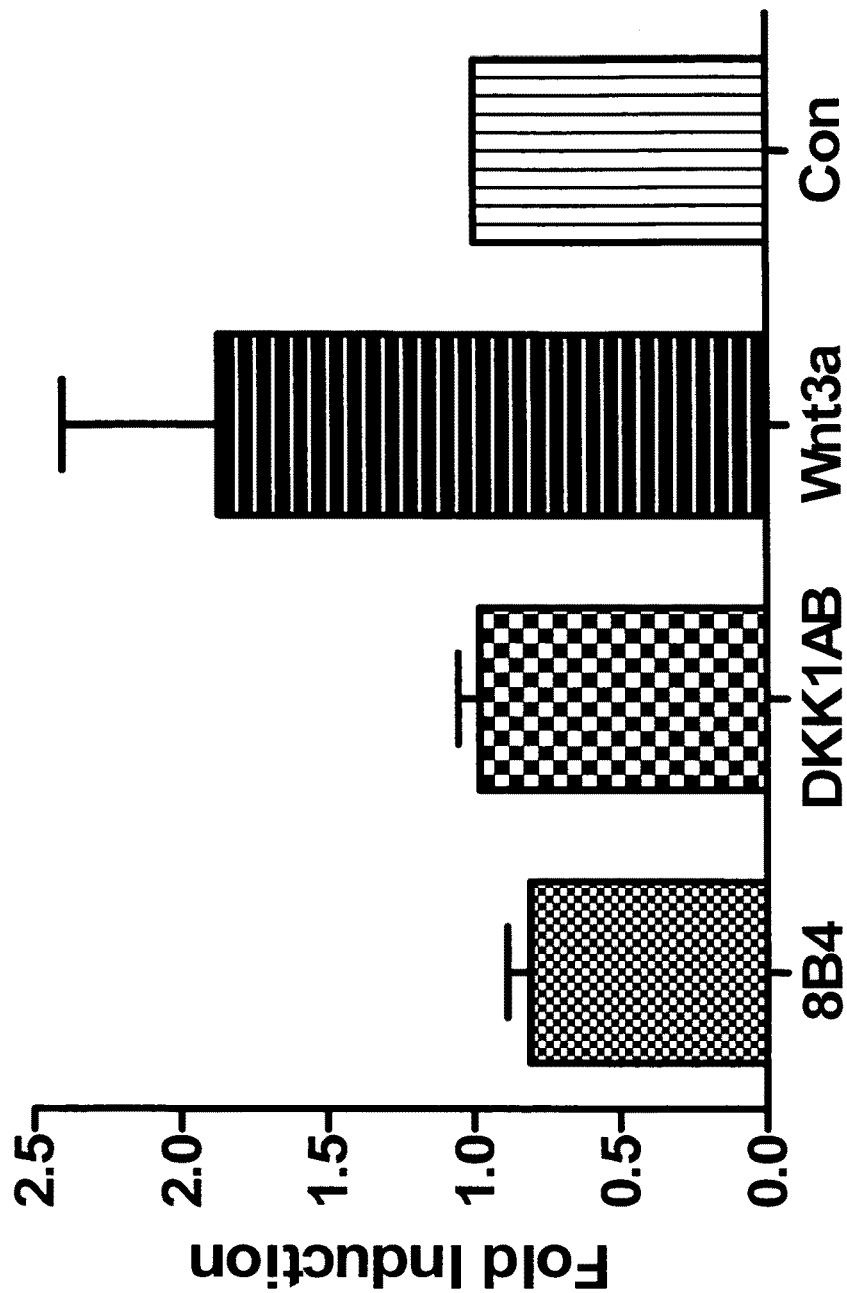
Figure 10B:
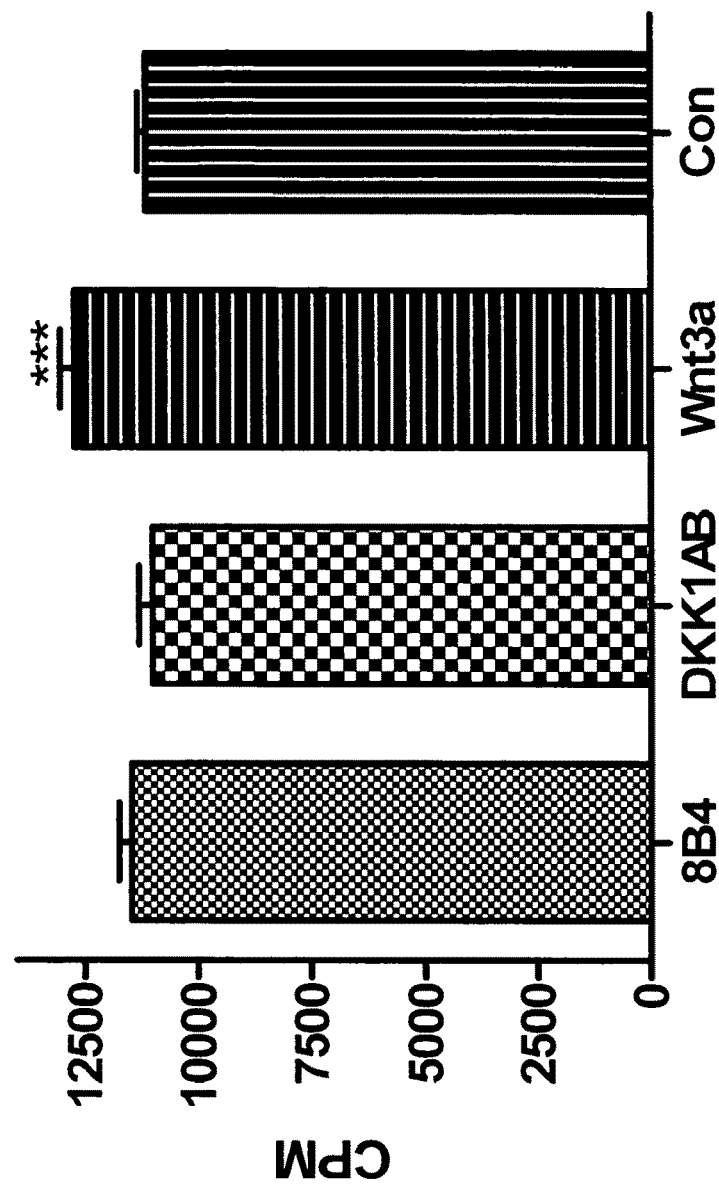

Results of the transcription and proliferation assays using HCT116 cells are shown in FIGS. 10A and 10B. In general, the results indicated that many cells had high baseline transcription levels that could not be further enhanced by Wnt treatment. For all cell lines, RH2-80 alone did not enhance LEF-1/TCF promoter activity. This lack of responsiveness was seen in cells that did respond to Wnt3a treatment, such as HCT116. Separate analyses showed that the anti-Dkk-1 antibody RH2-80 did not alter the expression of endogenous Wnt target genes, including myc, jun, PPARd, FGF18, COX2, IGF-1, and IGF-2. Further, there was no induction of Wnt signaling components such as Dkk-1, Dkk-2, Dkk-4, LRP5, LRP6, Sost, WIF1, and CTGF in any of the six tested cell lines.

In the cell proliferation studies, the results showed that RH2-80 (at 30 μg/mL) did not enhance any cell growth in each of the tested cell lines. Assays were performed in the presence of serum and in the absence or presence of supplemental Wnt3a treatment. The results for effect of RH2-80 antibody on HCT116 cell proliferation are shown in FIG. 11B. Parallel analyses tested RH2-80 and RH2-59 antibodies (both at 16 μg/mL) for an effect on the growth of MG-63, HCT116, and SW480 cells. No growth enhancement was observed in serum-containing medium. No stimulation of cell growth was observed by RH2-80 antibody treatment of MG-63 and HCT116 cells when tested in OPTIMEM serum free medium in comparison to vehicle (N.S.). Significance was observed in comparisons between RH2-80 and RH2-59 (anti-Dkk-1 antibody with similar efficacy) and with 20C2HA (negative control), both of which trended towards slight antiproliferative effects vs. the vehicle control (N.S.). Repeat analyses showed no antibody effects in HCT116 cells (seeded at higher initial density) and in SW480 cells in OPTI-MEM. In this regard, there was no downward trend in grown for cells treated with RH2-59 or 20C2HA, and again, RH2-80 performed identically to the vehicle control.

Figure 11:
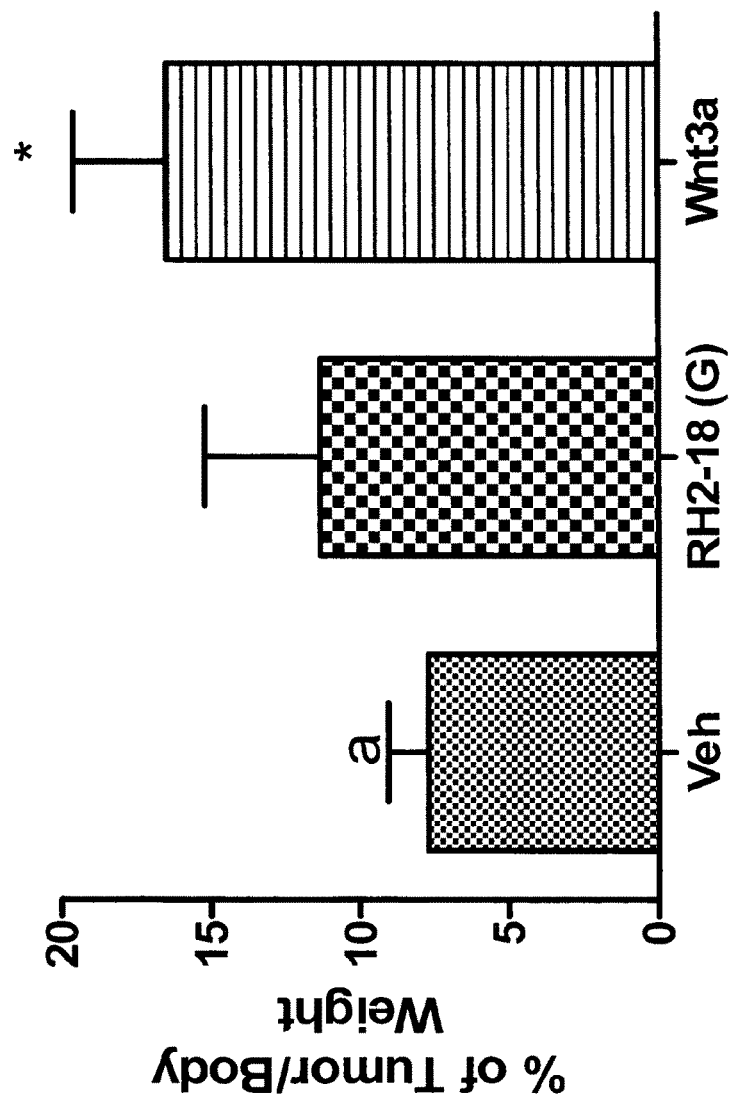

Further study of the anti-Dkk-1 antibodies in SCID mice of human colon cancer xenografts was also performed. In this xenograph model for tumor growth, phosphate-buffered saline (PBS) was used as the vehicle, RH2-18 antibody expressed in a *Pichia* strain at 5 mpk was used as the test group, while Wnt3a at 0.02 mpk was used as a positive control. Subcutaneous injection of $1 \times 10^7$ HCT116 cells in 100 µL PBS into the right and left flank of about six-week-old NOD.CB17-Prkdcscid/J (SCID) mice. Treatments were followed on the second day after injection and continued twice week for a total of seven treatments. Tumors were isolated after about 3.5 weeks. Percent of tumor weight was obtained by combing both tumors from one mouse and dividing by the mouse's total body weight. Statistics were performed using Student's t Test. The results are shown in FIG. 11. Wnt3a significantly increased tumor growth vs. the PBS (Vehicle) treated group by about two-fold. The antibody did not significantly stimulate tumor growth vs. vehicle treatment. Two of four animals in the vehicle group showed some evidence of tumor cells in the abdomen, which was not observed in the other groups. This possible HCT116 cell infiltration into the abdomen may have artificially reduced the apparent tumor size in these mice due to cell loss in the region of interest and thus, could have lowered the tumor size in these groups.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. An isolated monoclonal antibody that specifically binds a mature human Dkk-1 protein consisting of amino acids 32-266 of SEQ ID NO: 35 and having a tertiary structure established by a disulfide bond between cysteine residues 220 and 245, wherein the antibody binds to an epitope within a loop consisting of the amino acids between cysteine residues 201 and 210 of SEQ ID NO: 35.

2. The isolated antibody of claim 1 that is a human or humanized antibody.

3. An isolated monoclonal antibody or that competes with the antibody of claim 1 for specific binding to a Dkk-1 polypeptide.

4. The isolated antibody claim 3 that competes with an antibody that consists of two identical heavy chains and two identical light chains, wherein the heavy chains consist of the amino acid sequence set forth in SEQ ID NO: 3 and the light chains consist of the amino acid sequence set forth in SEQ ID NO: 7.

5. The isolated antibody claim 4 that dissociates from the Dkk-1 polypeptide with a Kd of about 269 pM or less.

6. An isolated antibody that binds to human Dkk-1, wherein
   (a) the heavy chain variable region of said antibody comprises CDR1, CDR2 and CDR3 amino acid sequences as set forth in SEQ ID NO: 9, SEQ ID NO: 10 and SEQ ID NO: 11 respectively; and
   (b) the light chain variable region of said antibody comprises CDR1, CDR2 and CDR3 amino acid sequences as forth in SEQ ID NO: 12, SEQ ID NO: 13 and SEQ ID NO: 14 respectively.

7. The isolated antibody of claim 6, wherein said antibody specifically binds a mature human Dkk-1 protein consisting of amino acids 32-266 of SEQ ID NO: 35 and having a tertiary structure established by a disulfide bond between cysteine residues 220 and 245, wherein the antibody binds to an epitope comprising a loop consisting of the amino acids between cysteine residues 201 and 210 of SEQ ID NO: 35.

8. An isolated antibody that binds to human Dkk-1, wherein
   (a) the heavy chain variable region of said antibody comprises CDR1, CDR2 and CDR3 amino acid sequences as set forth in SEQ ID NO: 67, SEQ ID NO: 68 and SEQ ID NO: 69 respectively; and
   (b) the light chain variable region of said antibody comprises CDR1, CDR2 and CDR3 amino acid sequences as forth in SEQ ID NO: 12, SEQ ID NO: 13 and SEQ ID NO: 61 respectively.

9. An isolated antibody that binds to human Dkk-1, wherein
   (a) the heavy chain variable region of said antibody comprises CDR1, CDR2 and CDR3 amino acid sequences as set forth in SEQ ID NO: 9, SEQ ID NO: 10 and SEQ ID NO: 11 respectively; and
   (b) the light chain variable region of said antibody comprises CDR1, CDR2 and CDR3 amino acid sequences as forth in SEQ ID NO: 12, SEQ ID NO: 62 and SEQ ID NO: 63 respectively.

10. An isolated antibody that binds to human Dkk-1, wherein
    (a) the heavy chain variable region of said antibody comprises CDR1, CDR2 and CDR3 amino acid sequences as set forth in SEQ ID NO: 9, SEQ ID NO: 10 and SEQ ID NO: 11 respectively; and
    (b) the light chain variable region of said antibody comprises CDR1, CDR2 and CDR3 amino acid sequences as forth in SEQ ID NO: 64, SEQ ID NO: 65 and SEQ ID NO: 66 respectively.

11. An isolated antibody that binds to human Dkk-1 comprising
    (a) a heavy chain variable region which comprises CDR1, CDR2, and CDR3 amino acid sequences as set forth in SEQ ID NO: 9, SEQ ID NO: 10 and SEQ ID NO: 11 respectively; and
    (b) a light chain variable region selected from the group consisting of SEQ ID NO: 4, SEQ ID NO: 48 and SEQ ID NO: 49.

12. The isolated antibody of claim 10, wherein the heavy chain variable region comprises the amino acid sequence set forth in SEQ ID NO: 8.

13. An isolated antibody that binds to human Dkk-1 and has a VL and VH pair selected from SEQ ID NO: 47 in combination with SEQ ID NO: 58; SEQ ID NO: 4 in combination with SEQ ID NO: 8; SEQ ID NO: 48 in combination with SEQ ID NO: 59 and SEQ ID NO: 49 in combination with SEQ ID NO: 60.

* * * * *